(12) United States Patent
Miller et al.

(10) Patent No.: US 11,412,980 B2
(45) Date of Patent: Aug. 16, 2022

(54) OPTICAL SENSOR FOR WEARABLE DEVICES

(71) Applicant: Halo Wearables, LLC, Morgan, UT (US)

(72) Inventors: David R. Miller, Morgan, UT (US); Jeffrey M. Lee, Morgan, UT (US); Devin W. Miller, Morgan, UT (US)

( * ) Notice: Subject to any disclaimer, the term of this patent is extended or adjusted under 35 U.S.C. 154(b) by 306 days.

(21) Appl. No.: 16/391,244

(22) Filed: Apr. 22, 2019

(65) Prior Publication Data

US 2019/0246977 A1    Aug. 15, 2019

Related U.S. Application Data

(63) Continuation of application No. 14/985,249, filed on Dec. 30, 2015, now Pat. No. 10,307,101.
(Continued)

(51) Int. Cl.
| | |
|---|---|
| *A61B 5/1455* | (2006.01) |
| *A61B 5/00* | (2006.01) |
| *H04W 52/02* | (2009.01) |
| *A61B 5/11* | (2006.01) |
| *A61B 5/0537* | (2021.01) |
| *A61B 5/145* | (2006.01) |

(Continued)

(52) U.S. Cl.
CPC .......... *A61B 5/4875* (2013.01); *A61B 5/0059* (2013.01); *A61B 5/0537* (2013.01); *A61B 5/1118* (2013.01); *A61B 5/1455* (2013.01); *A61B 5/14546* (2013.01); *A61B 5/6801* (2013.01); *A61B 5/681* (2013.01); *A61B 5/7221* (2013.01); *A61B 5/7278* (2013.01); *A61B 5/742* (2013.01); *H04W 52/0254* (2013.01); *H04W 52/0261* (2013.01); *A61B 5/0075* (2013.01); *A61B 5/02055* (2013.01); *A61B 5/318* (2021.01); *A61B 5/6803* (2013.01); *A61B 2090/064* (2016.02); *A61B 2560/0209* (2013.01); *A61B 2560/0252* (2013.01); *A61B 2560/0257* (2013.01); *A61B 2560/0456* (2013.01); *A61B 2560/0475* (2013.01); *A61B 2562/0219* (2013.01); *A61B 2562/0223* (2013.01); *A61B 2562/0261* (2013.01)

(58) Field of Classification Search
CPC . A61B 5/1455; A61B 5/14546; A61B 5/6801; A61B 5/4875; A61B 5/0537; A61B 5/7278; A61B 5/742
See application file for complete search history.

(56) References Cited

U.S. PATENT DOCUMENTS

| | | |
|---|---|---|
| 5,372,136 A | 12/1994 | Steuer |
| 6,442,408 B1 | 8/2002 | Wenzel |
| (Continued) | | |

*Primary Examiner* — Eric F Winakur
(74) *Attorney, Agent, or Firm* — Miller IP Law LLC

(57) ABSTRACT

Methods, systems, apparatuses, and/or devices for taking optical measurements. The methods, systems, apparatuses, and/or devices may include: emitting a first wavelength of light into the body; receiving light from a depth below a surface of the body corresponding to blood or sub-epidermis tissue of the body; and determining a physiological condition of the body when a current amount of light reflected or backscattered the blood or the sub-epidermis tissue and by the received by the optical sensor is different than a previous amount of light reflected or backscattered the blood or the sub-epidermis tissue and by the received by the optical sensor.

20 Claims, 20 Drawing Sheets

Related U.S. Application Data

(60) Provisional application No. 62/192,932, filed on Jul. 15, 2015, provisional application No. 62/117,282, filed on Feb. 17, 2015.

(51) Int. Cl.
*A61B 5/0205* (2006.01)
*A61B 90/00* (2016.01)
*A61B 5/318* (2021.01)

(56) References Cited

U.S. PATENT DOCUMENTS

| | | |
|---|---|---|
| 6,687,519 B2 | 2/2004 | Steuer |
| 2014/0114151 A1 | 4/2014 | Miller |
| 2014/0213863 A1 | 7/2014 | Loseu |
| 2014/0221792 A1* | 8/2014 | Miller ............... A61B 5/4875 600/309 |
| 2014/0275852 A1 | 9/2014 | Hong |
| 2015/0057515 A1 | 2/2015 | Hagen |

* cited by examiner

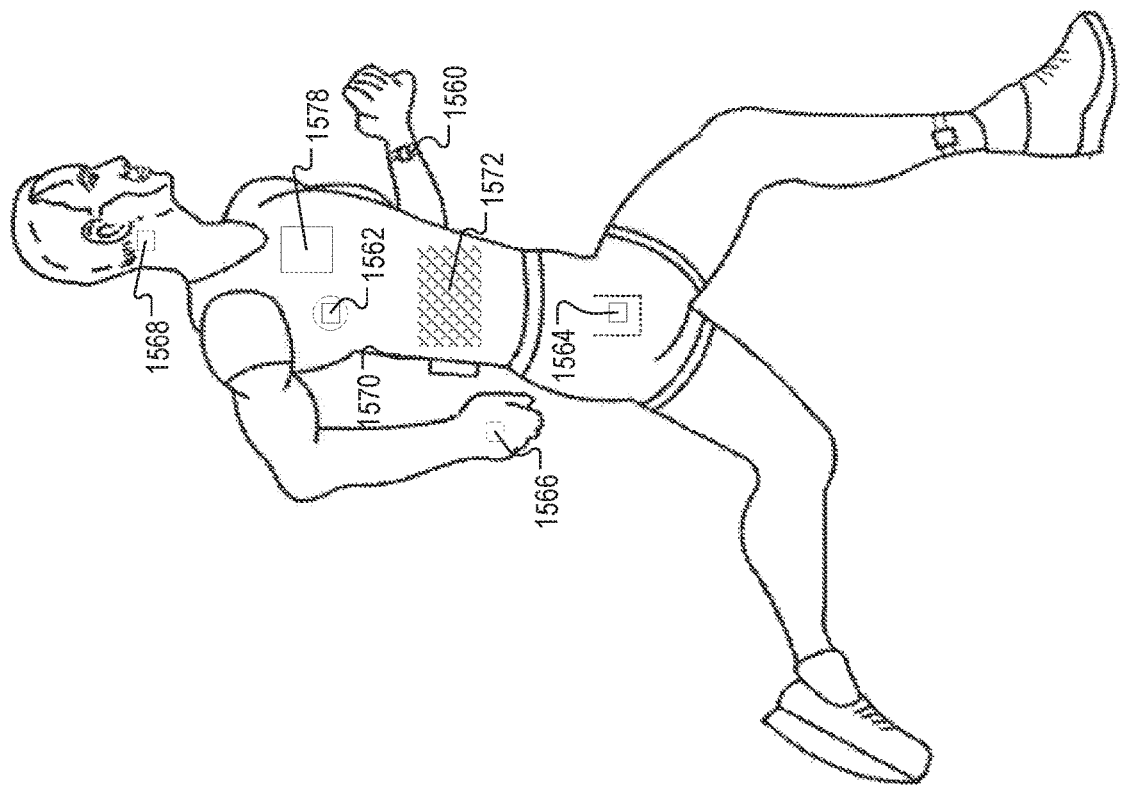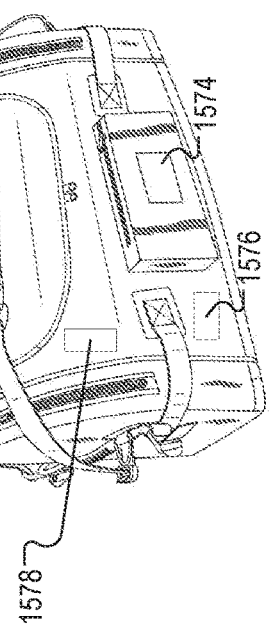
FIG. 15

OPTICAL SENSOR FOR WEARABLE DEVICES

RELATED APPLICATIONS

This application is a continuation of application Ser. No. 14/985,249, filed Dec. 30, 2015, which claims the benefit of U.S. Provisional Application No. 62/117,282, filed Feb. 17, 2015 and U.S. Provisional Application No. 62/192,932, filed Jul. 15, 2015, the entire contents of which are incorporated by reference.

BACKGROUND

Dehydration is a condition in which water in a living body decreases below the individual's normal functioning level. Dehydration often occurs when an individual is exerting energy for extended periods of time, an individual intakes little or no water, or the temperature rises to a point where an individual cannot excrete enough sweat to maintain their normal body temperature. Persons that regularly exert themselves in low humidity and/or high temperature conditions and/or for extended periods of time are prone to experience dehydration or dehydration symptoms. Elderly persons and children are also especially prone to experience dehydration or dehydration symptoms.

When a person experiences a dehydrated condition, the individual's ability to perform tasks may begin to deteriorate. For example, in the case of long distance endurance athletes, an individual that becomes dehydrated by loss of as little as 2% body weight may begin to have their performance impaired. Losses in excess of 5% of body weight can decrease the capacity of an individual to perform a task by as much as 30%.

BRIEF DESCRIPTION OF THE DRAWINGS

The disclosure will be understood more fully from the detailed description given below and from the accompanying drawings of various embodiments of the disclosure. The drawings, however, should not be taken to limit the disclosure to the specific embodiments, but are for explanation and understanding only.

FIG. 15 depicts body area network (BAN) devices communicating using a BAN, according to one embodiment

DESCRIPTION OF EMBODIMENTS

Figure 1:
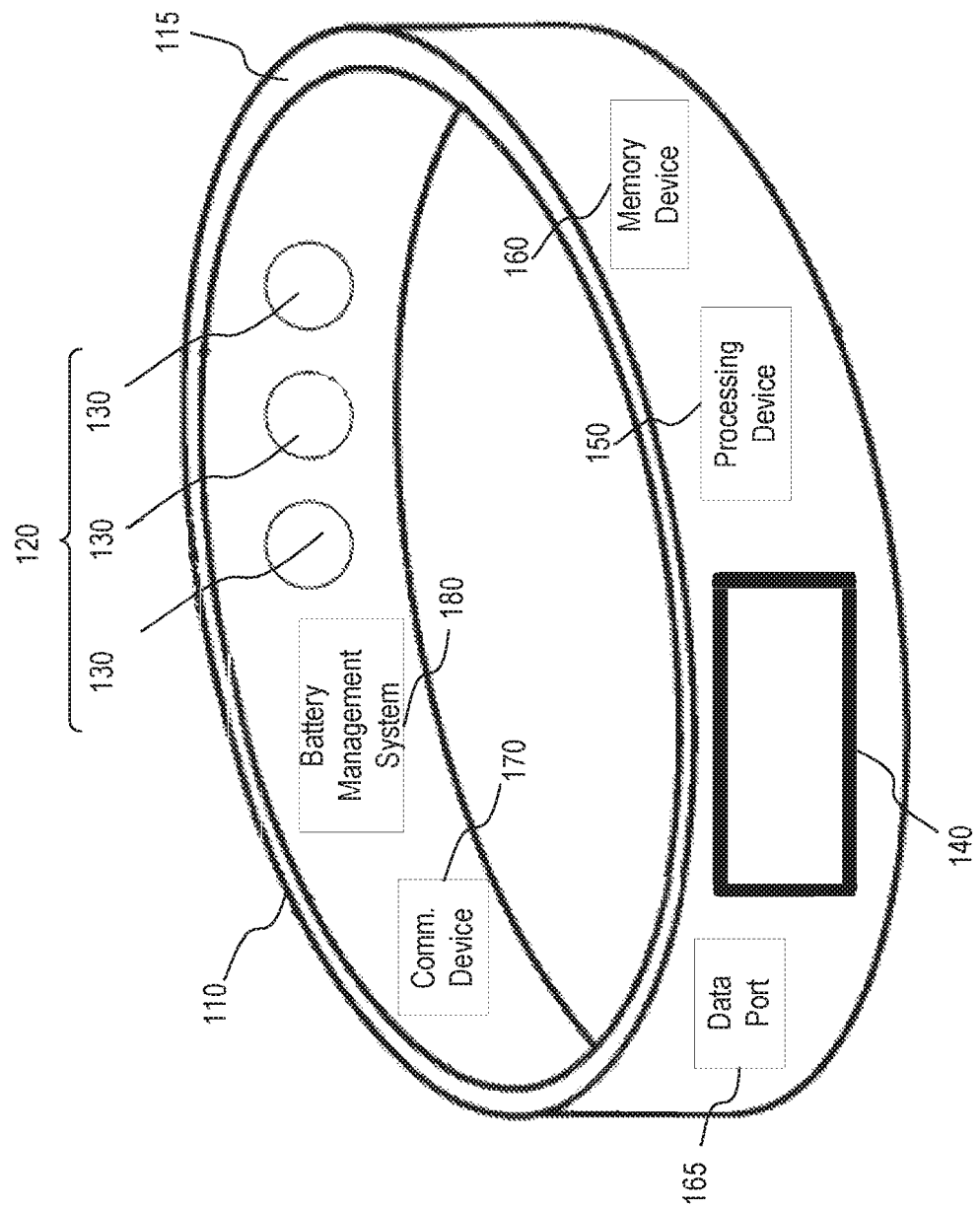
FIG. 1 depicts an electronic device, according to one embodiment.

Contemporary methods of measuring the hydration level of a person include measuring body weight changes over a period of time and urinalysis. One crude way of monitoring a person's fluid balance is to monitor how the body weight of a user changes over a short period of time. In this method, taking a body weight measurement each morning can show a pattern of hydration over time. The same method can be applied to determine how much sweat an athlete excreted while exercising by weighing the athlete before and after exercise.

Urinalysis can also be used to determining moderate changes in a person's fluid balance. A simple approach to urinalysis is to analyze the color of the person's urine to determine their hydration level. More scientific urinalysis tests such as urine specific gravity and urine osmolality can be used for a more accurate measurement of a user's fluid balance.

However, urinalysis and tracking a user's body weight changes over time are invasive procedures that fail to give the user real time information regarding the user's changing hydration condition. Thus, it is desirable that an individual's hydration level is monitored regularly and any dehydration is detected in the early stage before an individual's performance levels are impacted or before they reach a serious dehydration condition.

The embodiments described herein address the above noted deficiencies by determining a hydration condition of a user using spectrophotometry. Spectrophotometry is used to measure how much a compound or substance absorbs light by measuring the intensity of a beam of light after the beam of light passes through a sample of the compound or substance. Light can either be absorbed into a substance or it can be reflected by the substance. The presence of certain salts, minerals, or compounds in a substance determines which wavelengths are reflected and which are absorbed. For example, salts, such as potassium and sodium, absorb wavelengths of light at specific frequencies. For example, sodium may absorb wavelengths between 535 nanometers (nm) and 735 nanometers. In another example, potassium may absorb wavelengths between 680 nanometers and 880 nanometers. Thus, by emitting light with a specific wavelength corresponding to a salt, such as sodium or potassium, and measuring the intensity of the light at the specific wavelength after it has passed through the salt, it is possible to determine how much of the salt exists in a given sample. In another example, the amount of hemoglobin in the blood stream can be another indicator of the body's hydration condition. Hemoglobin absorbs wavelengths of light that are approximately 660 nanometers, 940 nanometers, and 1320 nanometers. Hemoglobin is the protein molecule in red blood cells that carries oxygen from the lungs to the body's tissues and returns carbon dioxide from the tissues back to the lungs. The wavelengths of light as discussed herein are not intended to be limiting. The wavelengths used for measurements (such as sodium, potassium, or hemoglobin) may vary or be within a given range. For example, an electronic device may measure an absorption of hemoglobin at 660 nanometers. In another example, the electronic device may measure an absorption of hemoglobin at wavelengths between 640 nanometers and 680 nanometers.

In one example, measuring the level of various substances in the human body may indicate a hydration condition of the body. Specifically, the level of electrolytes in a living body may operate as an indicator to the hydration condition of the living body. Electrolytes are salts carrying an electric charge that reside in the blood stream and other body fluids. Electrolytes affect the amount of water in the body, acidity of the blood (pH), muscle function, and other important processes. These electrolytes are lost when the body perspires. Specifically, when a person becomes dehydrated, the skin pulls sodium and to some degree potassium from the blood causing the blood to become less concentrated with substances such as sodium and potassium. Two key electrolytes, potassium and sodium, help regulate the water balance in the blood and other bodily tissue. Potassium is a body salt that is important to both cellular and electrical functions in the body. Additionally, potassium is one of the main salt in the blood considered to be an "electrolyte", along with sodium and chloride. Sodium and potassium regulates the water balance in the blood stream and other bodily tissues. Thus, by measuring levels of sodium, potassium and other substances in the bloodstream by an electronic device, a hydration condition of the body can be determined.

In one embodiment, the electronic device may include a housing shaped to be worn by a user. The housing can have an outer surface and an inner cavity to house electronic components, as discussed in greater detail in the proceeding paragraphs. In one embodiment, the housing can have multiple cavities on an outer surface. For example, the housing may have a first cavity, a second cavity, and a third cavity on the underside of the outer surface of the housing. In one embodiment, a cavity can be an indentation or a pit an inner surface or outer surface of the housing. In another embodiment, a cavity is a channel that extends from the outer surface of the housing to the inner cavity of the housing. Components of the electronic device may be disposed in various channels located in the housing. For example, a light source may be embedded into a channel of the housing, connected to one of the electronic components in the inner cavity, and emit light towards a surface of the user's body.

Figure 5:
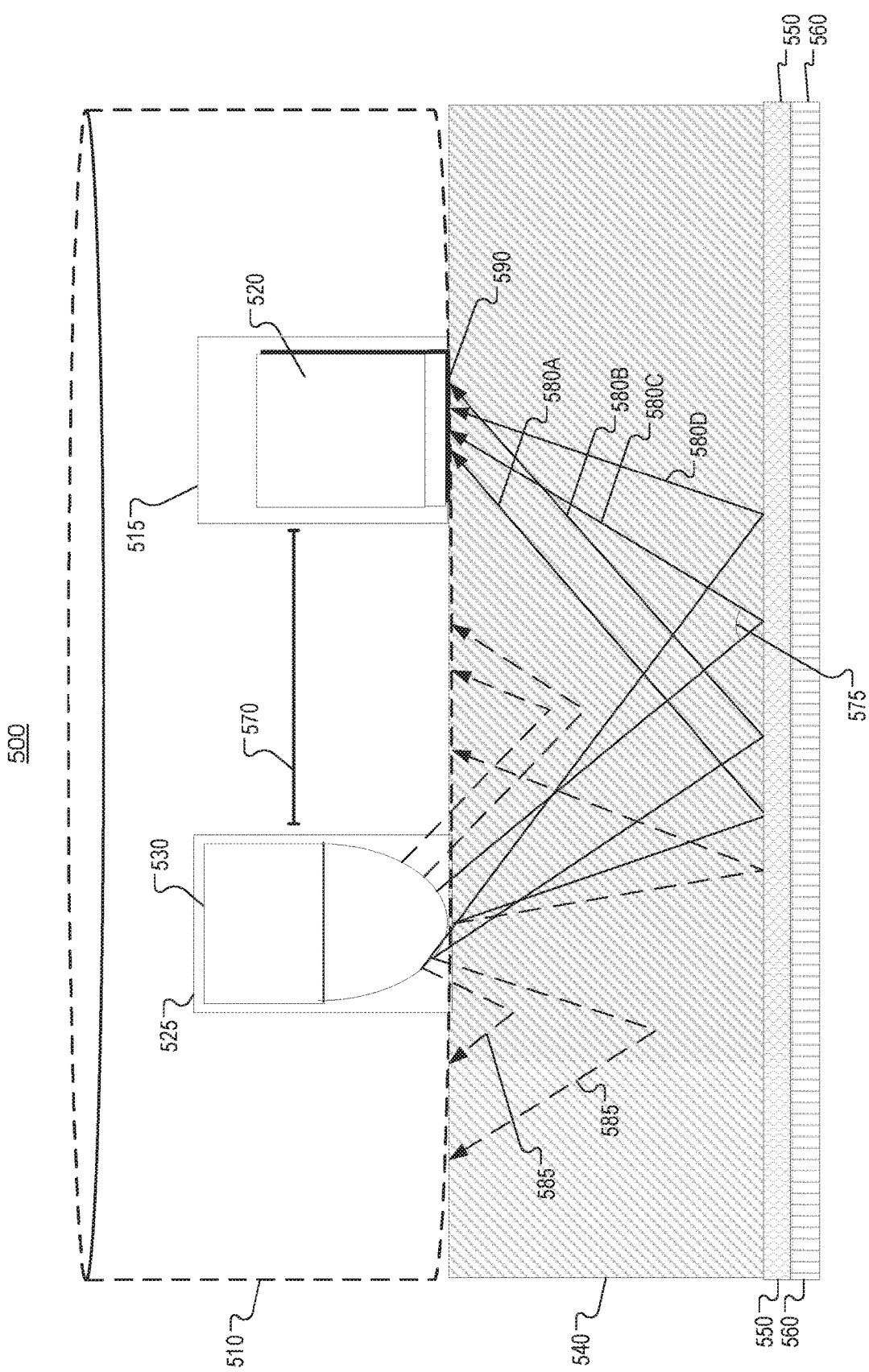
FIG. 5 depicts cross sectional side view of an electronic device interacting with a user, according to one embodiment.

The electronic device may have a first light source disposed into the first cavity of the housing, see for example FIG. 5. In one example, the first light source may not extent beyond the surface of the housing. In this example, the light source may be flush with a first plane defined by a surface of the housing such that both the surface of the housing and the light source contact the skin of the user. In another example, the first light source may be recessed into the housing. In this example, the first light source may be recessed into the housing such that the first light source does not contact the skin of the user when the device is worn by the user. In another example, the first light source may extend beyond the surface of the housing for increased contact with the skin when the device is worn by the user. The first light source may be operable to emit light into the body of the user, where the light includes a first wavelength corresponding to a wavelength absorbed by sodium.

In one embodiment, the first light source may emit light of a full spectrum of wavelengths between 400 nanometers and 1800 nanometers. In another example, the first light source may emit light at a discrete wavelength corresponding to a wavelength absorbed by a particular substance. In another example, the first light source may emit light of a discrete wavelength at 535 nanometers to correspond to a wavelength absorbed by sodium in the body. In another example, the first light source may emit light of one or more discrete wavelengths between 535 nm and 735 nm that correspond to the wavelengths absorbed by sodium in the body. In another example, the first light source may emit light at a discrete wavelength of 780 nanometers to correspond to a wavelength absorbed by potassium in the body. In another example, the first light source may emit light of one or more discrete wavelengths between 680 nanometers and 880 nanometers that correspond to the wavelengths absorbed by potassium in the body.

In one example, the electronic device may measure light of multiple wavelengths to determine a hydration condition of the body. The optical sensor may take measurements of a full spectrum of measurements over the range of 400 nanometers to 1800 nanometers. These measurements can be taken over a continuous amount of time or periodically. In one example, the electronic device may determine if an amount of light (e.g., absorption, reflection, or backscatter) at the discrete wavelengths of the spectrum of wavelengths have changed over one or more measurements. In this example, the first light source may emit a full spectrum of wavelengths between 400 nanometers and 1800 nanometers into the body. The electronic device may take continuous measurements over the entire spectrum of wavelengths to determine if an amount of light (e.g., absorption, reflection, or backscatter) at any discrete waveforms have changed over multiple measurements. In another embodiment, the electronic device may take measurements at n number of discrete wavelengths out of the spectrum of wavelengths emitted from the first light source. In one example, n may be 10. In another example, n may be 50 or 100. In another example, harmonically related frequencies may be used to determine a salt content level in the body. For example, a measurement of light at a wavelength of 645 nanometers may correspond to a measurement of sodium in the body. In some embodiments, a content level of sodium in the body may be determined by measuring an amount of light at a wavelength that is a multiple of a defined wavelength of light. For example, the electronic device may measure the sodium in the body using the optical sensor and a light source that emits light at 645 nanometers or 645 nanometers multiplied by n. In this example, when n is equal to 2, the electronic device may measure the sodium in the body using the optical sensor and a light source that emits light at 1290 nanometers (645×2 nanometers).

In another embodiment, the electronic device includes a second light source disposed into the second cavity of the housing. In one example, the second light source may not extent beyond the surface of the housing. In another example, the second light source may be recessed into the housing. In this example, the second light source may be recessed into the housing such that the first light source does not contact the skin of the user when the device is worn by the user. In another example, the second light source may extend beyond the surface of the housing for increased contact with the skin when the device is worn by the user. The second light source may be operable to emit light into the body of the user, where the second light includes a second wavelength corresponding to a wavelength absorbed by potassium.

In another embodiment, the electronic device includes an optical sensor disposed into the third cavity of the housing. In one example, the optical sensor may not extent beyond the surface of the housing. In another example, the optical sensor may be recessed into the housing or extend beyond the surface of the housing. In one example, the optical sensor may be a fixed distance from the first light source, as described in greater detail in the proceeding paragraphs. In another example, the optical sensor may be a second fixed distance from the second light source, as described in greater detail in the preceding paragraphs. In another example, the optical sensor is to detect a portion of the light reflected by a structure of the body, such as a muscular-walled tube of the body, at a depth below the body surface of the user. The preceding examples are not intended to be limiting. The number of light sources is not limited the first and second light source. In other embodiments, the electronic device can include one or a plurality of light sources. Additionally, the number of optical sensors and the distance between the optical sensors is not intended to be limiting. The electronic device can include a one or a plurality of optical sensors at various distances between the optical sensors and the various light sources.

In another embodiment, the electronic device includes a sensor interface coupled to the optical sensor. In one example, the sensor interface may receive a detected portion of light from the optical sensor and may determine a first measurement of backscatter for the first wavelength of light using the detected portion of the light. In this example, light reflected by bodily tissue is referred to as backscatter. In another example, the sensor interface may determine a second measurement of backscatter for the second wavelength of light using the detected portion of the light. In one example, backscatter is the diffused reflection of light due to the scattering of light off bodily tissue. In another example, backscatter is the specular reflection, or the direct reflection, off bodily. In one embodiment, the sensor interface determines the amount of light which is the diffused reflection of the light due to the light scattering off a muscular-wall tube of the body. In another embodiment, the sensor interface may determine the amount of light received by the optical sensor due to the specular reflection of the light off a portion of bodily tissue.

In another embodiment, the electronic device may include a processing device coupled to the sensor interface. The processing device may compare the first measurement of backscatter of the first wavelength to a previous measurement of backscatter of the first wavelength and determine a change in the sodium level of the body when the amount of backscatter of the first wavelength changes. In one example, the processing device may compare the second amount of backscatter of the second wavelength to a previous measurement of backscatter of the second wavelength and determine a change in the potassium level of the user when the amount of backscatter of the second wavelength changes. In another example, the processing device or sensor interface may provide a hydration condition to the user, as described in greater detail in the proceeding paragraphs.

FIG. 1 illustrates an electronic device 110, according to one embodiment. FIG. 1 illustrates that the electronic device 110 can be a wearable device such as a wristband, a headband, an armband, a chest band, a leg band, an ankle band, a strap, a garment or piece of clothing (such as a hardhat or shirt), an accessory, or other object that can be shaped to attach or couple to an user. The electronic device 110 can also be integrated into other wearable objects such as a hard hat, a safety harness, a safety lock out, shoes, a bag, and so forth. Alternatively, the electronic device may be an implantable device that may be implanted under the skin of the user.

In one example, the electronic device 100 can be located in an area that is practical for the individual to wear the electronic device 110 for an extended period of time, such as a 24-hour period. For example, as many individuals are accustom to wearing wristwatches, a comfortable location for the individual to wear the electronic device 110 for an extended period of time may be at the wrist location. In another example, the electronic device may be located at a location on the individual that will provide a high measurement accuracy level, such as a location on the individual that is the most sensitive to a selected physiological measurement. For example, the chest, wrist, tip of the finger, or ear lobe may be locations that are sensitive to taking physiological measurements and the electronic device 110 can be shaped to attach to the individual at chest, wrist, tip of the finger, or ear lobe locations.

In one embodiment, the electronic device 110 may include a housing 115 with one or more inner cavities. The one or more cavities can include space to house: a sensor array 120, a sensor 130, a display 140, a processing device 150, a memory device 160, a communication device 170, and/or a battery management system (BMS) 180. In one embodiment, the housing 115 can be hermetically sealed. e.g., airtight, water proof, sweat proof, dust proof, and so forth. In another example, the housing can be a unibody (e.g., a single unit), where components such as the sensor 130 can be sealed within the unibody. In another embodiment, the housing 115 can include multiple pieces, such as a first housing piece and a second housing piece, that are sealed together to form a hermetically sealed housing 115.

In one example, the electronic device 110 can be an invasive device attachable to (or implantable within) a body of a user to obtain an invasive physiological measurements from the user. In another example, the electronic device 110 can be a non-invasive device attachable to the body of the user to obtain non-invasive measurements from the user.

The electronic device 110 can include a sensor 130 or sensor array 120 that can be integrated into the electronic device 110. In another example, the sensor 130 or the sensor array 120 can be coupled to the processing device 150 of the hydration monitoring device. 110. In one example, the sensor 130 can be a physiological sensor. The physiological sensor can include an impedance sensor, an optical sensor, an electrocardiography (ECG) sensor, a fluid level sensor, an oxygen saturation sensor, a body temperature sensor (skin temperature or core temperature), a plethysmographic sensor, a respiration sensor, a breath rate sensor, a cardiac sensor, a bio-impedance sensor, a spectrometer, a heart rate sensor, a blood pressure sensor, a pulse oximeter, or other physiological sensors. In another example, the sensor 130 can be a Newtonian sensor. The Newtonian sensor can include: a two dimensional (2D) accelerometer, a three dimensional (3D) accelerometer, a gyroscope, a magnetometer, a vibration sensor, a force sensor, a pedometer, a strain gauge, and so forth. In another example, the sensor 130 can be a location sensor. The location sensor can include: a global positioning system (GPS); a triangulation system; and so forth. In another example, the sensor 130 can be an environmental sensor. The environmental sensor can include: a humidity sensor, an ambient temperature sensor, an altitude sensor, a barometer, a weather sensor, and so forth. In one embodiment, the sensor 130 can be a non-invasive sensor. In one embodiment, one or more of the physiological sensors, the Newtonian sensors, or the environmental sensors can be integrated into the electronic device 110 or physically coupled to the electronic device 110. In another example, one or more of the physiological sensors, the Newtonian sensors, or the environmental sensors can be physically separate from the electronic device 110 and can be communicate data with the electronic device, either directly or indirectly as discussed herein.

In one embodiment, the electronic device 110 can include a display 140 to show information to a user or a third party based on the measurements from the sensor 130 or the sensor array 120. In one embodiment, the display 140 can show the time, e.g., a clock. In another embodiment, the information shown on the display 140 may include measurement information, such as: a light backscatter measurement, a heart rate of an individual, a breathing rate of the individual, a blood pressure of the individual, and so forth. In another example, the information shown on the display 140 may include recommendations, such as: a recommendation to take a break; a recommendation to go home; a recommendation to go to a hospital; or other recommendations. In another example, the information shown on the display 140 may include alerts, such as: an alert that a user may be experiencing a dehydration condition; an alert to take medication; an alert that an environment may not be safe; an alert that the user has fallen down; or other alerts. In another example, the information shown on the display 140 may include: hydration information, health status information, and other information.

In another embodiment, the display 140 can display information to a user or a third party based on information from other devices in communication with the electronic device 110. For example, the electronic device 110 can receive information from an automobile or a smart home device of a user or a third party. In this example, the information from the automobile or the smart home device can include ambient temperatures, humidity information, weather information, and so forth. The electronic device 110 can display the information from the automobile or the smart home device or use it in combination with measurements taken using the sensor 130 or the sensor array 120 to determine and display other information, such as a hydration level of the user.

In another embodiment, the processing logic of the electronic device 110 can determine an error with the sensor 130 or the sensor array 120 and display the error to the user or the third party using the display 140. For example, the processing logic can determine that the sensor 130 or the sensor array 120 is not interfacing with the user properly and the processing logic can use the display 140 to display an error message to the user. In one embodiment, the sensor 130 or the sensor array 120 is not interfacing with the user properly when the sensor 130 or the sensor array 120 is only partially contacting the body of the individual or is not completely contacting the body of the individual. In another embodiment, the sensor 130 or the sensor array 120 is not interfacing with the user properly when an object or particle is interfering with processing logic using the sensor 130 or the sensor array 120 to take physiological measurements of the user, environmental measurements, or other measurements. In one example, processing logic can determine that object or particle is interfering with taking measurements when measurement information is outside a defined measurement range or there is a discontinuity in the measurement information that exceeds a threshold level for the discontinuity. For example, when dirt comes between the sensor 130 or the sensor array 120 and the body of the user, the dirt can cause a discontinuity in the measurement information. When the processing logic determines the discontinuity in the measurement information, the processing logic can use the display 140 to display an error message associated with the discontinuity.

In another embodiment, the sensor 130 or the sensor array 120 is not interfacing with the user properly when the electronic device 110, the sensor 130, or the sensor array 120 has become dislocated or displaced. For example, measurements taken using the sensor 130 or the sensor array 120 with a first orientation can have a higher accuracy level than measurements taken using the sensor 130 or the sensor array 120 with a second orientation. In one example, the first orientation is an orientation where the user is wearing the electronic device 110 in a correct orientation and the second orientation is an orientation when the electronic device 110 has slipped or shifted to a different orientation. When the electronic device 110 has slipped or shifted the second orientation, the processing logic identifies that a measurement is outside a defined measurement range or there is a discontinuity in measurement information and uses the display 140 to display an error message associated with slippage or shifting.

In one example, the display 140 can be a touch screen display, such as a capacitive touch screen or a resistive touch screen. In another example, the display 140 can display a graphical user interface (GUI) to receive information. In another example, the electronic device 110 can include a data port 165, such as a universal serial bus (USB) port, a mini-USB port, a micro-USB port, a LIGHTNING® port, and so forth. In another example, the electronic device 110 can include a wireless communications device 170 (as discussed in the proceeding paragraphs) to send or receive information. The electronic device 110 can include a processor or processing device 150 to analyze or process measurements, received information, user input data, and/or other types of data.

In one example, the electronic device 110 can monitor stress on a respiratory system of the individual. For example, the electronic device 110 can use the sensor 130, such as an oxygen saturation sensor, to monitor the stress on a respiratory system of the individual.

In another example, the electronic device 110 can use one or more sensors 130 in the sensor array 120 to monitor stress on a plurality of systems of an individual, such as a biological system or a body system. The biological system may include a respiratory system, a cardiovascular system, a nervous system, an integumentary system, a urinary system, an excretory system, a digestive system, an immune system, an endocrine system, a lymphatic system, a muscular system, a skeletal system, a reproductive system, and other systems. The body system may include two or more organs working together in the execution of a specific bodily function, e.g., a neuroendocrine system, a musculoskeletal system, etc. For example, the electronic device 110 can monitor stress on the cardiac system of an individual using a blood pressure sensor of the sensor array 120 and can monitor the stress on the respiratory system of the individual using an oxygen saturation sensor of the sensor array 120.

In another example, the electronic device 110 can monitor biological systems, organs, body parts, body system, or other areas of an individual. In another example, the electronic device 110 can monitor or aggregate stress measurements from the sensors of the sensor array with other measurements, such as a lung capacity of an individual, a hematocrit (HCT), an oxygen saturation level, and/or or other medical measurements. In another example, the electronic device 110 can analyze the aggregated measurements to determine stress on one or more biological systems, organs, body parts, and/or body system and use the aggregated measurements to determine medical, health, and/or safety conditions.

In one example, the electronic device 110 can use the sensor array 120 to monitor a medical condition of an individual, such as a cardiac condition, under various environments or conditions for continuous, semi-continuous, or a periodic period of time on a long-term or protracted basis. In one example, sensor measurements can be collected using the sensor 130 in the sensor array 120 of the electronic device 110. In another example, the sensor measurements can be stored on a non-tangible computer readable medium device 160 (e.g., a memory device) coupled to the electronic device 110 or in communication with the electronic device 110.

In one embodiment, the battery management system (BMS) 180 can include: one or more batteries (such as a rechargeable battery), a charger, and a management device. The management device can manage and control power, e.g., power to and from the one or more batteries or regulate power of the electronic device 110. For example, the management device can direct power received from an external power source, such as wall outlet, via the data port 165 (e.g., a USB port) and can recharge the one or more batteries. In another example, the BMS 180 can include a wireless power system with a wireless power coil to receive power. In this example, the management device can direct power received via the wireless power system to the one or more batteries. In another example, the management device can direct power to components or systems of the electronic device 110, such as the sensor array 120, the sensor 130, the display 140, the processing device 150, the memory device 160, and/or the communication device 170. In one example, the management device can be a processor or another processing device, independent of the processing device 150, that can manage and control the power. In another example, the management device can be software executed by the processing device 150 or processing logic to manage the power.

In one embodiment, the BMS 180 can determine when a charge level the one or more batteries is below a threshold amount and can send a notification to the user indicating that the electronic device 110 needs to be charged. In one example, the electronic device can send the notification to the user using a sensory device such as a vibrator, a speaker, a display, and so forth.

Figure 2B:
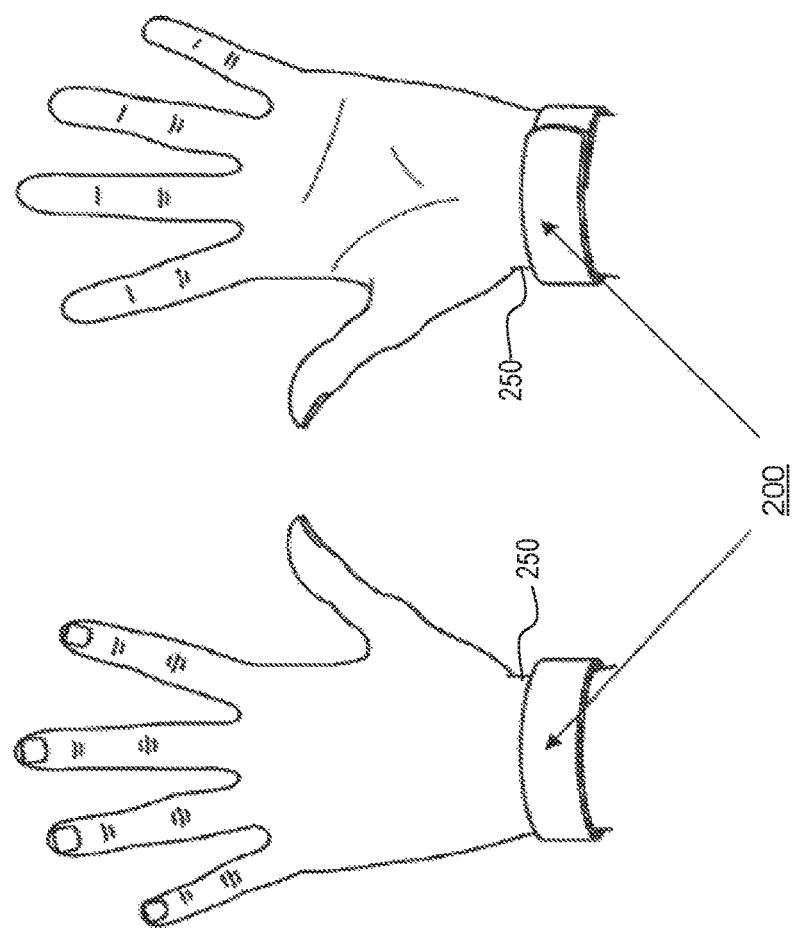
FIG. 2B depicts a top and a bottom perspective of an electronic device attached to a wrist of an individual, according to one embodiment.
Figure 2A:
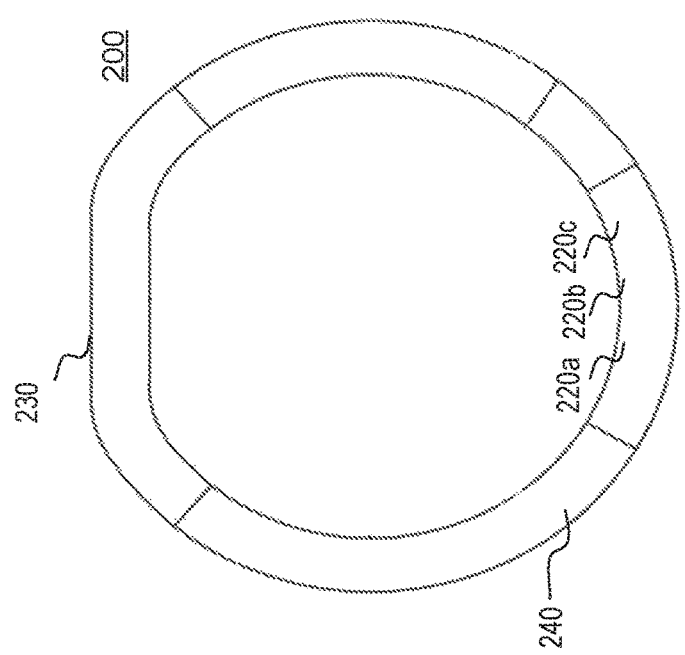
FIG. 2A depicts a side view of an electronic device, according to one embodiment.

FIG. 2A illustrates a side view of an electronic device 200, according to one embodiment. The electronic device 200 can include one or more integrated sensors 220. In one exemplary embodiment, the electronic device 200 can have a flat top portion 230 and a circular remaining portion 240 to fit to the contour or shape of a wrist on a user. An advantage of the electronic device 200 fitting to contours of the wrist can be to align the sensors 220 of the electronic device 200 with a specific location on the wrist of the individual (such as a bottom, side, or top of the wrist). The electronic device 200 may be fit to the contours of the wrist to provide and/or maintain proper contact between the sensor 220 of the electronic device 200 and a body of the user. The location of the sensors 220 is not intended to be limiting. The sensor 220 can be located at different locations on the electronic device 200. Additionally, a shape of the electronic device 200 is not intended to be limiting. The electronic device 200 can be a variety of different shapes, such as oval, circular, rectangular, and so forth.

FIG. 2B illustrates a top and a bottom perspective of an electronic device 200 attached to a wrist 250 of an individual, according to one embodiment. The electronic device 200 may be located on the wrist of an individual and may take one or more measurements at the wrist location. In one example, the electronic device 200 can cover or wrap around the circumference of the wrist 250 of the individual.

Figure 3:
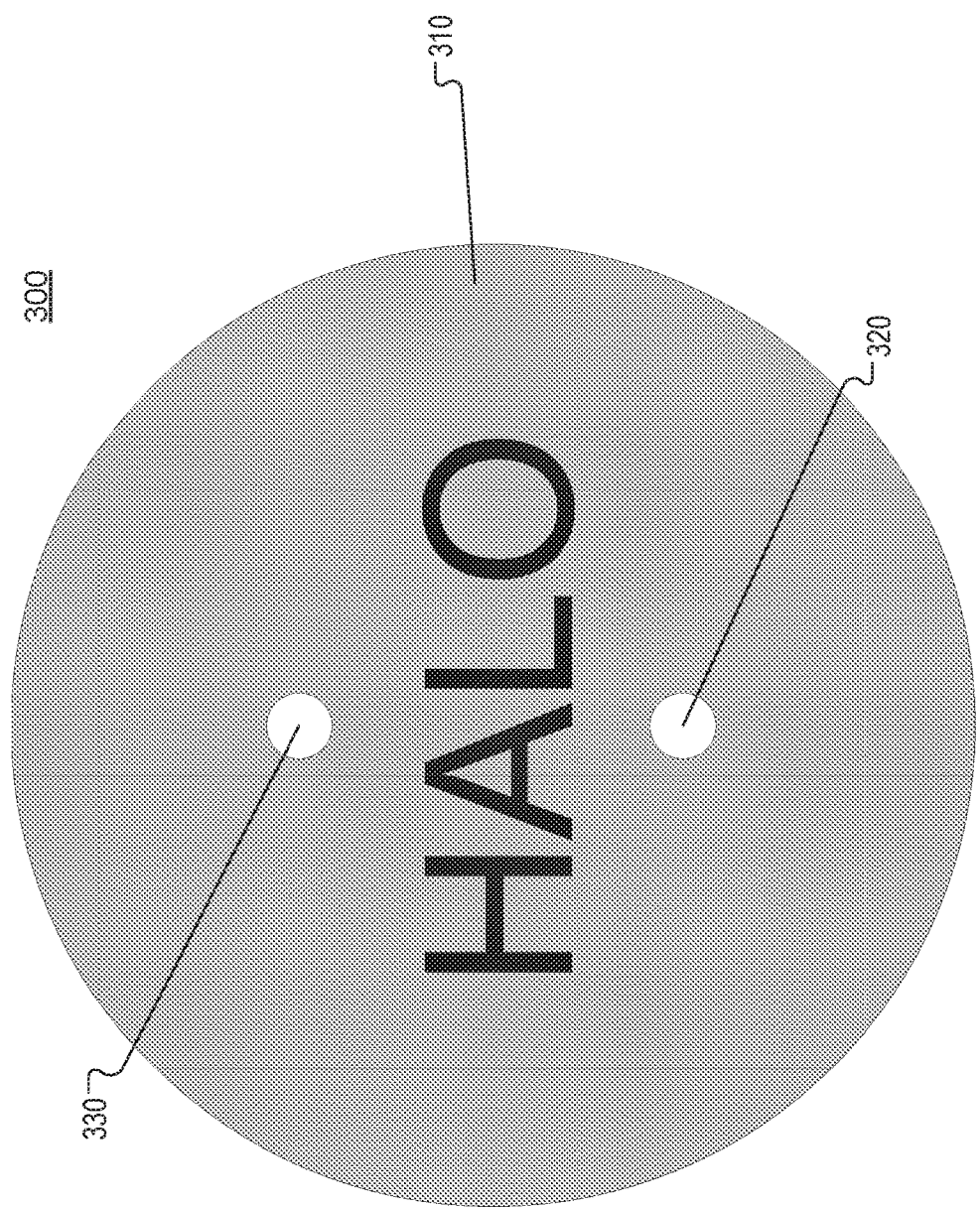
FIG. 3 depicts a top view of the electronic device, according to one embodiment.

FIG. 3 illustrates a top view of the electronic device 300, according to one embodiment. The electronic device 300 may have a display 310. The display 310 may provide information to a user such as indicating the user's hydration condition, temporal information such as the user's hydration condition over time, a time and date, and any information relevant to a user's physiological state. In one embodiment, the display 310 may be a graphical user interface (GUI) that allows a user to interact with the device. In another embodiment, the display may be located on an external device, such as a cellular telephone, a personal computer, or other mobile device. The electronic device 300 may further include a power indicator 320 to indicate a state of the electronic device 300. In another embodiment, the electronic device 300 may comprise one or more sensors such as a humidity and/or temperature sensor 330. In one embodiment, a humidity sensor may detect the humidity level of the user's environment or a sweat rate of a user. A temperature sensor may detect the temperature of the user's environment or a surface temperature of a user.

Figure 4:
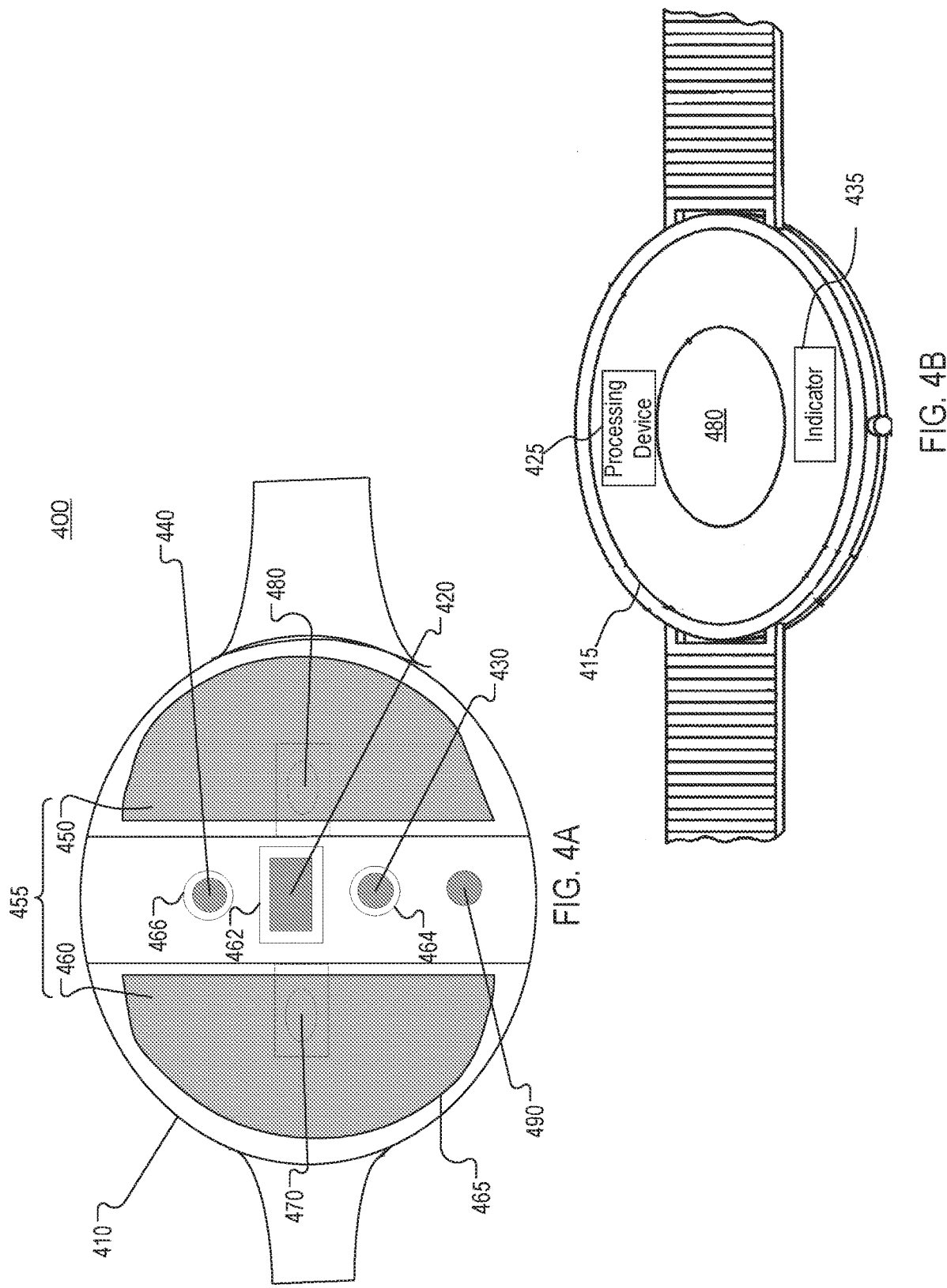
FIG. 4A depicts the underside of an electronic device, according to one embodiment.
FIG. 4B depicts an underside view or interior view of the electronic device, according to one embodiment.

FIG. 4A illustrates the underside of an electronic device 400 is depicted, according to one embodiment. The electronic device 400 includes a housing 410, an optical sensor 420, light sources 430 and 440, an impedance sensor 455 including impedance pads 450 and 460, contact wings 470 and 480, and a humidity and/or temperature sensor 490. The housing 410 of the electronic device 400 may be shaped to affix to the wrist, head, arm, chest, leg, ankle, ear lobe, fingertip, or other surface of the body. The housing 410 may have one or more cavities to house components of the electronic device 400. In one example, electronic device has a cavity 465 to house the second impedance pad 460. As previously discussed, the cavity 465 may be disposed on a location on an outer surface of the housing 410. In this example, the underside of the housing 410 can be along a portion of the outer surface of the housing 410. In one example, the underside of the housing 410 may be the surface of the device that contacts the user when worn. In this example, the cavity 465 may be a channel extending from the underside of the outer surface of the housing 410 to an inner cavity of the housing 410. The contact terminal may be disposed in the channel such that the contact terminal is flush with the plane defined by the outer surface of the housing 410 and is coupled to another component of the electronic device that is disposed in the inner cavity of the housing 410. In other examples, the impedance pad 450, optical sensor 420, humidity and/or temperature port 490, and light sources 430 and 440 are disposed in the cavity 465 or other similar cavities.

The sensor components such as the optical sensor 420, light sources 430 and 440, impedance pads 450, 460, and humidity and/or temperature sensor 490 may be embedded into the one or more cavities of the underside of the housing 410 of the electronic device 400. In some cases, one or more sensor components may sit flush with a plane defined by an underside of the housing 410. When affixed to a user, the sensor components contact the skin of the user without extending beyond the plane defined by the underside of the housing 410. Alternatively, the sensor components may be recessed into the housing 410. In this example, the sensor components may be recessed into the housing 410 such that the sensor components do not contact the skin of the user when the device is worn by the user. In another example, the sensor components may extend beyond the surface of the housing 410 for increased contact with the skin when the device is worn by the user.

The optical sensor 420 may be embedded into cavity 462 and the light sources 430 and 440 may be embedding into cavities 464 and 466, respectively. Moreover, optical sensor 420 and light sources 430 and 440 may be located between impedance pads 450 and 460. In one embodiment, the light sources 430 and 440 are light emitting diodes (LEDs). In another embodiment, the light sources 430 and 440 may be incandescent light sources, halogen light sources, or the like. Light sources 430 and 440 may emit a full spectrum wavelength of light. In this example, a full spectrum wavelength describes the electromagnetic spectrum from infrared to near-ultraviolet. In another example, the light sources 430 and 440 may emit a discrete wavelength of light into a body. A discrete wavelength of light may be a range of wavelengths taken from the electromagnetic spectrum. In one example, a discrete wavelength of light can be between 535 nanometers and 735 nanometers. In another example, the discrete wavelength of light can be between 680 nanometers and 880 nanometers. Further, the discrete wavelengths may correspond to measurements of potassium, sodium, or other substances in the blood stream or other bodily tissue.

In one embodiment, optical sensor 420 is to detect an intensity of light at one or more wavelengths reflected by bodily tissue of a user. The optical sensor 420 is coupled to a processing device and a sensor interface. The sensor interface may receive the detected light from the optical sensor and measure the intensities, or the amount of light, received at a specific wavelength. In one embodiment, the optical sensor 420 is used in concert with other components of the electronic device 400 to determine a hydration condition of the body of a user. For example, the sensor interface unit 806 of the electronic device 400 may use the optical sensor 420 to detect the backscatter of a wavelength corresponding to a salt in the body. In another example, the sensor interface unit 806 may, through use of the impedance sensor 455, take an impedance measurement of the body. In one embodiment, the electronic device 400 may determine a hydration condition of the body using the impedance measurement or the backscatter measurement. In another embodiment, the electronic device 400 may determine a hydration condition of the body using the impedance measurement and the backscatter measurement in parallel or concurrently.

The sensor interface may determine a backscatter measurement by measuring the concentration levels of substances, such as electrolytes, in the body. For example, when the sensor interface unit 806 measures a decrease in backscatter from the baseline or previous backscatter measurement of the user of a wavelength corresponding to sodium in a muscular walled-tube of the body, the sensor interface may determine that the user's sodium level in the blood stream is increasing and the hydration condition of a user is declining. In one embodiment, the GUI or display may inform the user that they are becoming dehydrated. In the exemplary embodiment, the measurement is taken from a muscular-walled tube of the body such as a vein, artery, or the like. However, the measurement can be taken from other bodily tissues as well.

In one embodiment, the electronic device 400 includes impedance sensor 455 having impedance pads 450 and 460. Impedance sensor 455 may cause impedance pad 450 to send an electrical signal into a body. The impedance pad 460 may detect at least a portion of the electrical signal in the body. In one embodiment, the impedance sensor 455 can detect a change in the impedance of the body. The change in the impedance of the body can indicate a change in a hydration condition of the body. For example, as a level of the impedance increases, the hydration condition of body may be an increase in dehydration. In another example, as a level of the impedance decrease, the hydration condition of body may be an increase in hydration. The impedance sensor 455 may be coupled to a processing device and a sensor interface through contact wings 470 and 480.

In another embodiment, the electronic device 400 includes a humidity and/or temperature sensor 490. In one example, the humidity and/or temperature sensor 490 may perform a sweat rate measurement to determine an amount the body is perspiring. In another example, the humidity and/or temperature sensor 490 may perform a surface temperature measurement of the skin. In another embodiment, the electronic device 400 may also include a pulse oximeter to measure a user's blood oxygen level.

FIG. 4B illustrates a bottom view of the electronic device 400, according to one embodiment. The electronic device 400 may include a processing device 425 coupled to the sensors 420, 455, and 490 to take selected measurements. The processing device 425 may receive measurement information from the one or more sensors 420, 455, and 490 and analyze the measurement information to determine selected information, such as a hydration condition, physiological information, medical information, and so forth. In one example, the selected information can be hydration condition information, cardiac information (e.g., blood pressure or heart rate), blood oxygen level information, skin luminosity information, or other user information.

The electronic device 400 may also include one or more indicators 435 used to alert the user of the electronic device 400 of a hydration condition change. The indicator 435 may be on the top or the bottom of the electronic device 400 based on a type of the indicator 435. For example, the indicator 435 can be a display or light may be on the top of the electronic device 400. In another example, the indicator 435 can be a vibrator on the bottom of the electronic device 400. In another example, the indicator 435 can be a speaker.

FIG. 5 illustrates a cross sectional side view of an electronic device 500 interacting with a user, according to one embodiment. The electronic device 500 includes a housing 510 with cavities 515 and 525. The electronic device 500 may further include a light source 530 embedded in cavity 525. In one example, the light source 530 may emit a full spectrum of wavelengths between 400 nanometers and 1800 nanometers. In another example, the light source 530 is an LED emitting light of a discrete wavelength corresponding to a wavelength absorbed by a particular substance. In another example, the LED may emit light of a discrete wavelength between 535 nanometer and 735 nanometers to correspond to the wavelengths absorbed by sodium in the body. In another example, the LED may emit light of a discrete wavelength between 680 nanometers and 880 nanometers to correspond to the wavelengths absorbed by potassium in the body.

The electronic device 500 further includes an optical sensor 520. The optical sensor 520 may receive backscatter 580A-D that has been reflected by tissue in the body. The optical sensor may be equipped with a lens 590. The lens 590 may be any shape or thickness, and may focus, narrow, or direct the emitted light. Backscatter may be discrete or full spectrum waveforms that have been reflected off bodily tissue. In some examples, when the wavelengths hit body tissue or a substance in the body, the wavelengths are scattered by the tissue or substance. The sensor interface unit 806 may measure the amount of light that has scattered by causing the optical sensor 520 to detect the amount of light that is scattered off body tissue. The processing device may determine the sodium or potassium level by comparing the amount of light emitted with the amount of light that is received at the optical sensor 520. The amount of light received by the optical sensor can be compared to a previous amount of backscatter to determine if the level of the substance in the body is increasing or decreasing.

The optical sensor 520 is separated from light source 530 by a fixed distance 570. Due to the angle of reflection 575 of light waves entering the body, the fixed distance 570 is fixed at a distance that allows the optical sensor 520 to detect backscatter of light that has been reflected by a desired depth of body tissue. If, for example, the optical sensor 520 is separated from the light source 530 by 1 millimeter (mm) to 3 mm, the optical sensor 520 may detect backscatter that has reflected off body tissue close to the surface, such as the epidermis and dermis layers 540, of the skin (e.g shallow backscatter 585). As the optical sensor 520 is increasingly separated from light source 530, the optical sensor may detect light that has penetrated and been reflected off deeper parts of bodily tissue. However, if the optical sensor 520 is separated from light source 530 by too great of a fixed distance, the optical sensor 520 will fail to detect enough light to take a measurement.

In one embodiment, optical sensor 520 and the light source 530 may be separated by a fixed distance 570 for measuring waveforms that have reflected off a muscular-walled tube of the body such as an artery 550 or vein 560. Veins and arteries of the body contain concentrations of substances such as potassium and sodium that correlate with the hydration condition of a body. When a person becomes dehydrated, the skin pulls potassium and sodium from the blood causing the blood to become less concentrated with salts such as sodium and potassium. When a person has a lower than normal sodium content in the blood stream, it may be an indicator that the person is becoming dehydrated. In some cases, as a person becomes dehydrated the potassium content in the blood stream may decrease or stay the same. In one example, the electronic device 500 will determine the hydration condition of the user by determining potassium to sodium ratio. When a person has a higher than normal potassium to sodium ratio in the blood stream, it may be an indicator that the person is dehydrated. In one example, the electronic device may determine the hydration condition of the user be comparing measurements of light at various wavelengths corresponding to more than one salt or substance in the body. In this example, the hydration condition may be determined by looking at ratios of the various minerals or substances in the body as determined by the electronic device. Thus, by measuring backscatter of wavelengths of light that are absorbed by sodium and potassium, the concentration of these substances in the blood stream can be determined. In another embodiment, when taking a measurement at the wrist, it may be desirable to separate the optical sensor 520 from the light source 530 by between 6 millimeters and 8 millimeters to measure the backscatter from vein 550 or artery 560. In one embodiment, to prevent light that has been emitted from light source 530 but that has not entered the body from reaching the optical sensor 520 and biasing a measurement, light piping or a barrier may be placed between the light source 530 and optical sensor 520.

Figure 6:
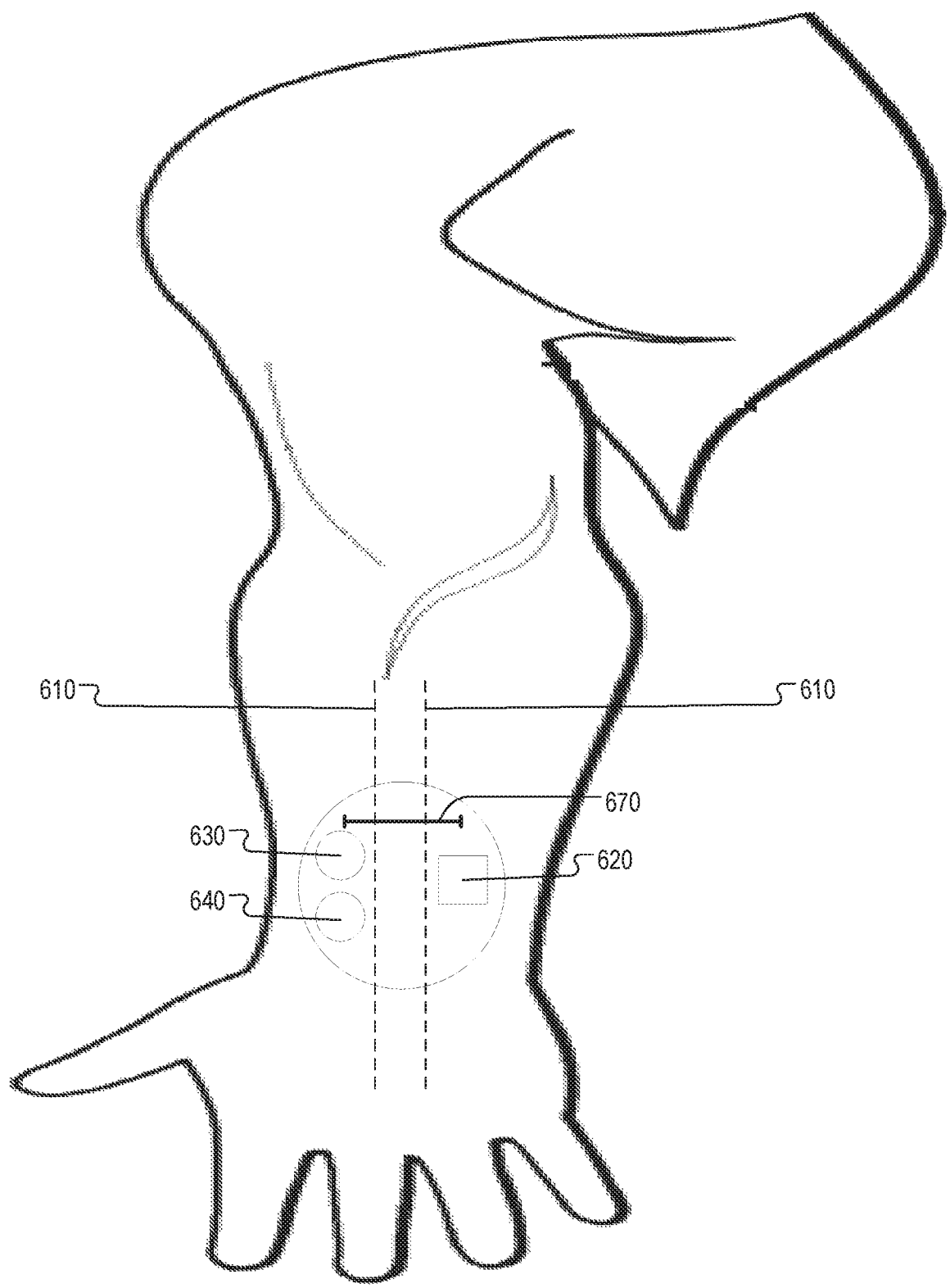
FIG. 6 depicts an electronic device oriented above the radial artery of a user, according to one embodiment.

FIG. 6 illustrates, an electronic device 600 oriented above the radial artery 610 of a user, according to one embodiment. The electronic device 600, as depicted, is oriented above the radial artery 610 of a user's arm to measure physiological data, such as a hydration condition. The electronic device may be oriented above the radial artery 610 to determine a concentration of substances such as potassium and sodium in a user's blood stream through a vein or artery. In one example, the electronic device is oriented above the radial artery 610 because the radial artery 610 is near the surface of the user's body. Measuring at a location that is near the surface of the skin minimizes the amount of backscatter that the optical sensor 620 detects from light that has been scattered by structures or substances in the body other than the intended artery or vein. To measure waveforms that have reflected off the radial artery 610, it may be desirable to position light sources 630 and 640 on one side of the radial artery 610 and the optical sensor 620 on the other side of the radial artery. This orientation allows the optical sensor 620 to measure backscatter off the radial artery 610. For example, when optical sensor 620 is positioned on one side of the radial artery 610 and light sources 630 and 640 are positioned on the other side of the radial artery 610, light that is emitted from the light sources 630 and 640 is scattered off the blood or blood constituents in radial artery 610 and detected by optical sensor 620. However, if the electronic device was not positioned over an artery or vein, such as the radial artery 610, there would not be a main conduit of blood between the light sources 630 and 640 and the optical sensor 620 for the optical sensor 620 to measure backscatter from. Moreover, optical sensor 620 and light sources 630, 640 are spaced at fixed distance 670 such that the optical sensor 620 detects backscatter that has penetrated bodily deep enough to have reflected off the radial artery 610. The radial artery 610 is an example of a muscular-walled tube of the body.

In one embodiment, the electronic device 600 measures the level of potassium, sodium, or another substance in the radial artery 610 to determine a hydration condition of the body. Sodium and potassium, individually or in combination, regulate the water balance in the blood and tissues of a user. Potassium best absorbs light wavelengths between 680 nanometers and 880 nanometers. In one example, optical sensor 620 detects light of a wavelength of 780 nanometers that has been reflected by potassium in the radial artery or other muscular-walled tube of the body to determine a potassium concentration in the blood stream. An increasing in the potassium to sodium ratio in the blood stream may indicate that the body is becoming dehydrated.

In another embodiment, the electronic device 600 measures the level of sodium in the body. In one example, excess sodium in the blood stream can cause an increase in the blood pressure of a user. In another example, a lack of sodium can cause a user to suffer nausea, vomiting, exhaustion, and dizziness. Additionally, sodium, along with potassium, is an electrolyte that when measured can be an indicator as to the hydration condition of the body. In one embodiment, sodium may absorb wavelengths between 535 nanometers and 735 nanometers. In one example, optical sensor 620 may detect light of a wavelength of 620 nanometers that has been reflected by sodium in the radial artery 610 or other muscular-walled tube of the body to determine a sodium concentration in the blood stream.

Figure 7:
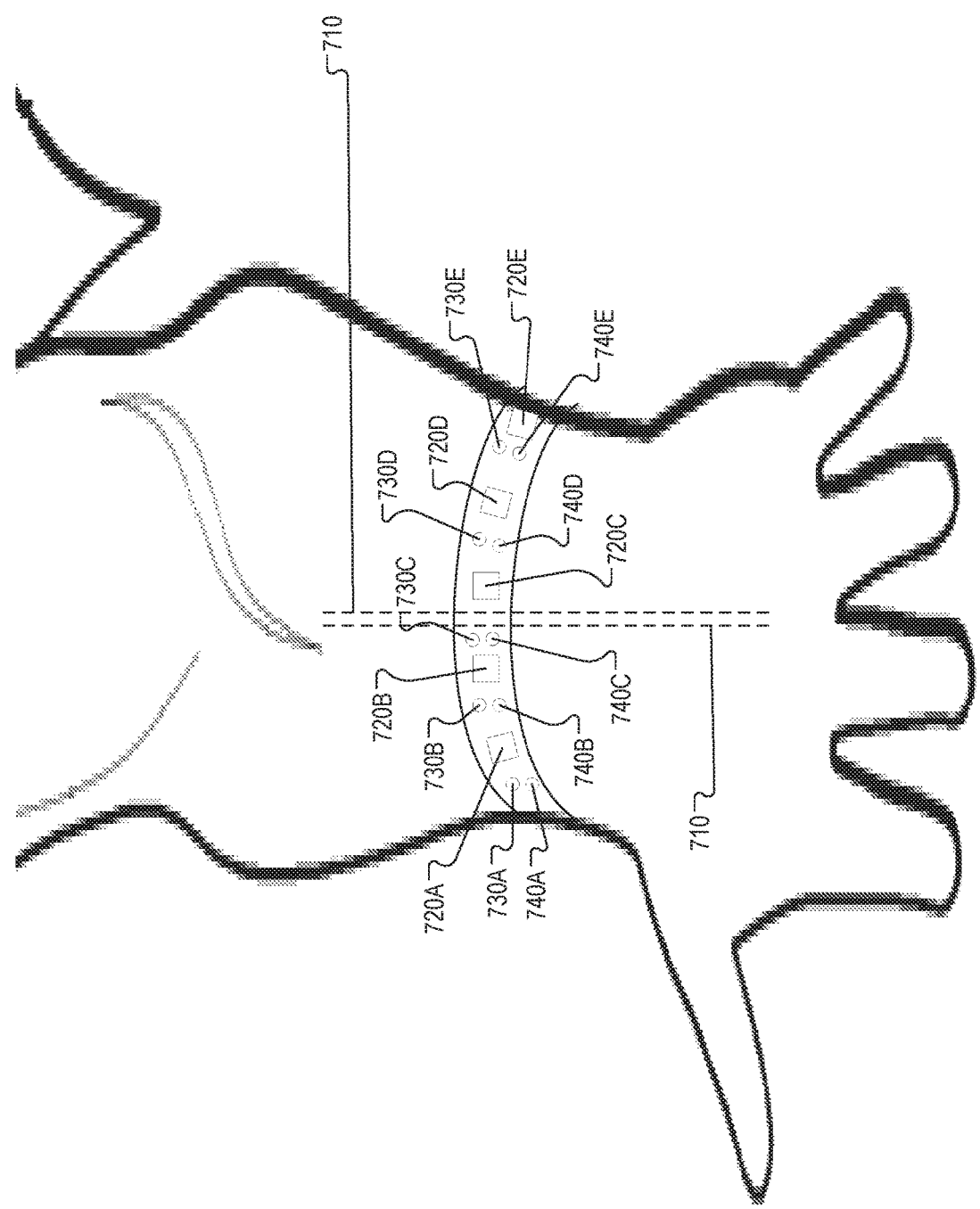
FIG. 7 depicts an electronic device having multiple optical sensors and light sources affixed to a user, according to one embodiment.

FIG. 7 illustrates, an electronic device 700 having multiple optical sensors 720A-E and light sources 730A-E and 740A-E affixed to a user, according to one embodiment. Electronic device 700 may have multiple light source 730A-E and 740A-E and optical sensor 720A-E configurations spaced around a wrist band, head band, torso band, or the like. In one embodiment, having multiple light source 730A-E and 740A-E and optical sensor 720A-E configurations may improve measurement accuracy if the electronic device 700 shifts on the body. For example, a user exercising may cause the electrical device 700 to shift around on the user's wrist. In this example, each set of optical sensor 720A-E and light sources 730A-E and 740A-E may be taking measurements of different locations around the wrist. The sensor interface may analyze the data from each set (e.g. optical sensor 720C and light sources 730C and 740C) to determine which optical sensor and light source set is over the radial artery 710 at any given time, and utilize that set's measurements to determine a hydration condition of the user. In one example, each optical sensor and light source set is concurrently taking measurements. When a set (e.g. optical sensor 720C and light sources 730C and 740C) is reading measurement data within a specific range known to be within the measurement range of a user's baseline hydration level or within the range of previous measurement taken from the user's radial artery, that specific set is used to determine a hydration condition. Further, optical sensor and light source sets that are detecting measurements outside of the user's known range may be presumed to not be measuring from the radial artery and these measurements may be discarded. In another example, if multiple optical sensor and light source sets are within the range known to be within the range of previous measurements taken from the user's radial artery, each of these measurements will be aggregated and used to determine the hydration condition of the user.

Figure 8:
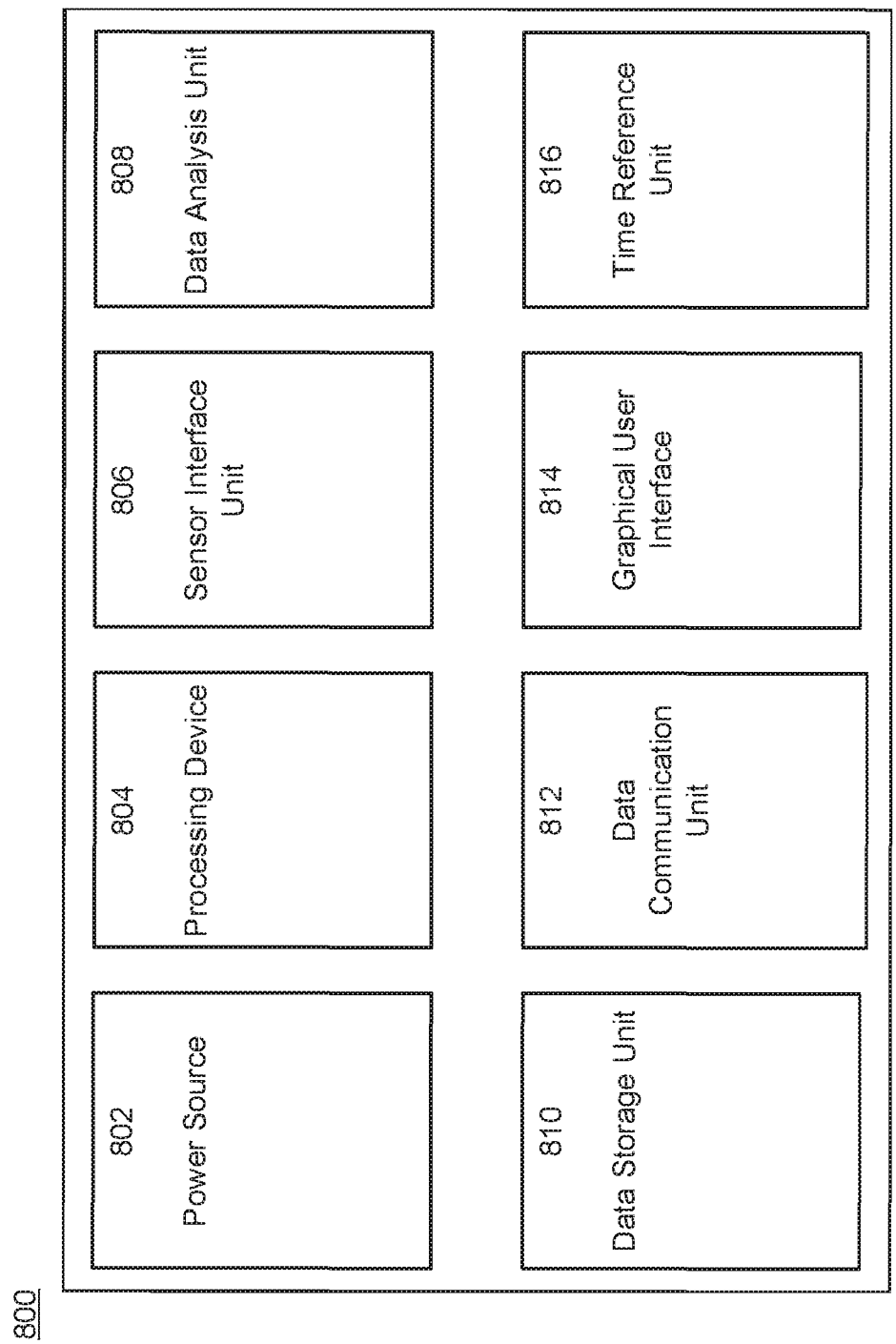
FIG. 8 depicts a block diagram of the electronic device, according to one embodiment.

FIG. 8 illustrates a block diagram of the electronic device 800, according to one embodiment. The electronic device 800 may include a power source 802, a processing device 804, a sensor interface unit 806, an analysis unit 808, a data storage unit 810, a data communication unit 812, a graphical user interface 814, and a time reference unit 816.

In one embodiment, the electronic device 800 includes a power source 802 that supplies power to components of the electronic device 800. The power unit 802 may include a battery to supply power and a charging unit that charges the battery. Alternatively, electronic device 800 is connectable to an energy source that powers the electronic device 800. In one embodiment, a charger may be used to recharge a battery or other energy source of the power source 802.

In another embodiment, the electronic device 800 includes a processing device 804. The processing device 804 may include a central processor to process the data and/or information of the other components that make up the electronic device 800 or other units, interfaces, and/or devices attached to or in communication with the electronic device 800.

In another embodiment, the electronic device 800 may include a sensor interface unit 806. The sensor interface unit 806 may be coupled to one or more sensors, such as the optical sensor, the impedance sensor, or the humidity and/or temperature sensor, and may perform one or more measurements relating to a physiological condition of a body using the one or more of the sensors. In another embodiment, the sensor interface 806 may be coupled to the processing device 804. The sensor interface 806 can use the one or more sensors to take measurements relating to a hydration condition of a body, an impedance measurement, a temperature of a body or of an environment, a humidity measurement of a body or of an environment, or another physiological state or environment condition. In one example, the sensor interface 806 may be coupled to the processing device 804 and the optical sensor. In this example, the sensor interface unit 806 may receive data from the optical sensor relating to a portion of light that was reflected off an artery or other muscular-walled tube. Alternatively, the sensor interface 806 and the processing device 804 may be the same component. The sensor interface unit 806 may measure the backscatter of one or more wavelengths that have been reflected off a vein, artery, or other muscular-walled tube using the portion of light.

In one embodiment, the electronic device 800 may include a time reference unit 816 that generates time reference data usable to control the time at which data is collected from the sensor interface unit 806. The time reference unit 816 may also be used to calculate spatial and/or temporal derivatives between information received from the sensor interface unit 806. In one embodiment of the disclosure, the time reference unit 816 may keep track of the calendar time, such as a clock. Alternatively, the time reference unit 816 may act as a timer, keeping track of a lapsed time or decrementing from a defined time to zero. The timer of the time reference unit 816 may be used to collect information or data from the sensor interface 806 for a defined period of time or to record how long the sensor interface 806 collects data.

In one embodiment, the electronic device 800 includes a data analysis unit 808. The data analysis unit 808 may be communicatively coupled to the processing device 804, sensor interface unit 806, time reference unit 816, and other components of the electronic device 800. The data analysis unit 808 may determine that a hydration condition has changed for a user by comparing temporal data from the time reference unit 816 to measurement data from the sensor interface unit 806. The data analysis unit 808 may communicate the hydration condition to a user through the graphical user interface (GUI) 814.

In one embodiment, the electronic device 800 includes a graphical user interface 814. The graphical user interface may be a monitor screen, liquid crystal display (LCD), LED display, or the like. In aspect, the GUI may present information such as a hydration condition to the user. In another aspect, the user may be able to interact with the electronic device though inputs or icons on the GUI.

Figure 9A:
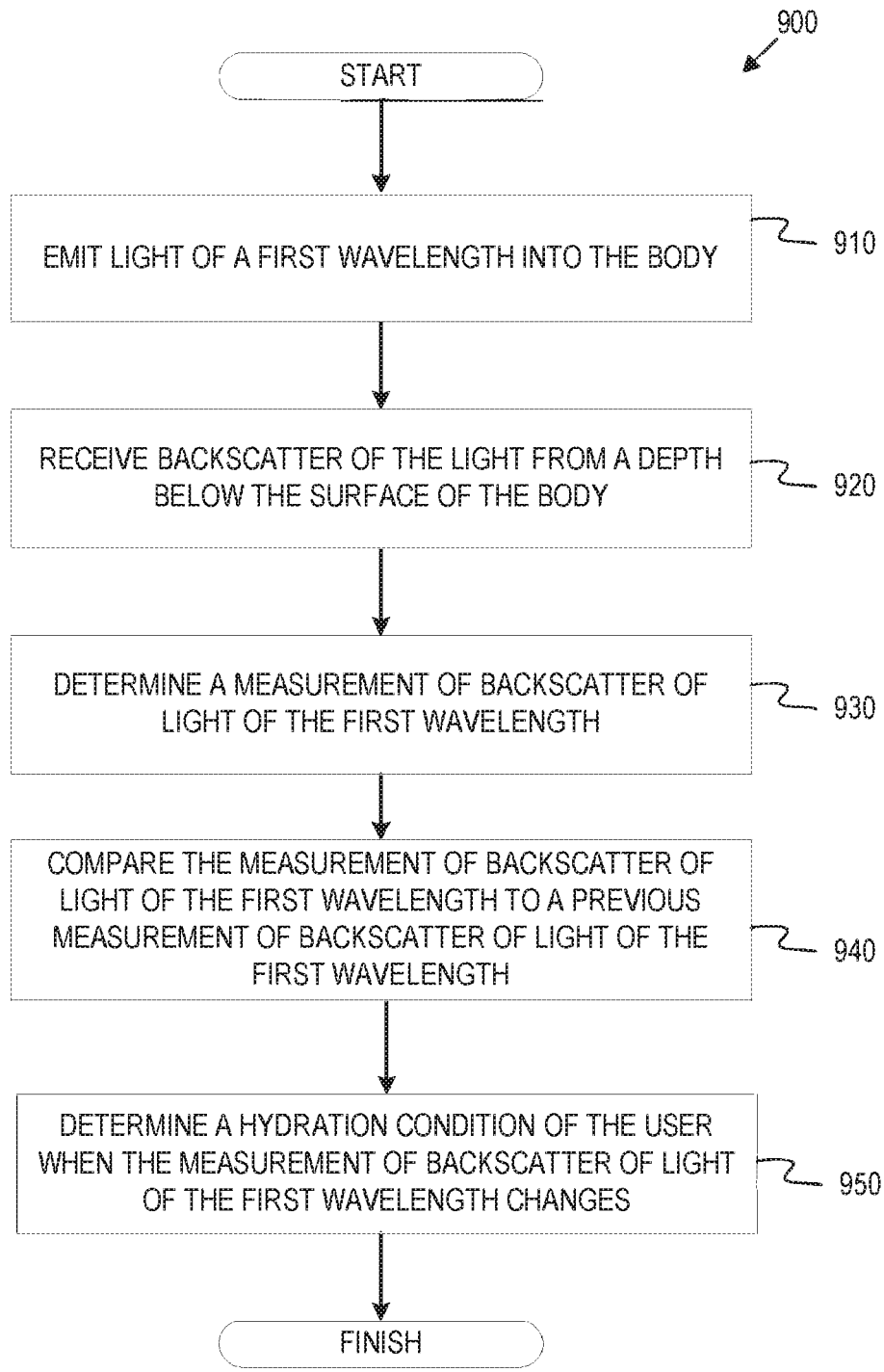
FIG. 9A depicts a flow diagram of a method of determining a hydration condition, according to one embodiment.

FIG. 9A illustrates a flow diagram of a method 900 of determining a hydration condition, according to one embodiment. The method 900 may be performed by processing logic that may include hardware (e.g., circuitry, dedicated logic, programmable logic, microcode, etc.), software (such as instruction run on a processing device, a general purpose computer system, or a dedicated machine, firmware, or a combination thereof. In one embodiment, the method 900 may be performed, in part, by processing logic of processing device 804.

For simplicity of explanation, the method 900 is depicted and described as a series of acts. However, acts in accordance with this disclosure can occur in various orders and/or concurrently and with other acts not presented as described herein. Furthermore, not all illustrated acts may be performed to implement the method 900 in accordance with the disclosed subject matter. In addition, those skilled in the art will understand and appreciate that the method 900 could alternatively be represented as a series of interrelated states via a state diagram or events.

The method can include, emitting light, from a first light source (910). In one embodiment, the first light source can be coupled to a sensor interface, where the sensor interface can turn the first light source on to emit light at a first location into the user. In another embodiment, the first light source can emit the light at a first wavelength. In another embodiment, the light source can be affixed to a body of a user to emit into a body of the user. The first wavelength may be a discrete wavelength or a full spectrum of wavelengths. In one embodiment, the discrete wavelength may be between 535 nanometers and 735 nanometers. The discrete wavelength 535 nanometers and 735 nanometers may correspond to a wavelength that is absorbed by sodium. In another embodiment, a discrete wavelength may be between 680 nanometers and 880 nanometers. The discrete wavelength 680 nanometers and 880 nanometers may correspond to a wavelength that is absorbed by potassium. In another embodiment, the electronic device can include multiple light sources that emit light at different wavelengths. For example, the electronic device can be include a first light source to emit light at a wavelength between 535 nanometers and 735 nanometers and a second light source to emit light at a wavelength between 680 nanometers and 880 nanometers.

The method can include receiving, by the optical sensor, backscatter of the light from a depth below the surface of the body (920). In one embodiment, the optical sensor may be positioned at a fixed distance from the light source to detect backscatter from a muscular-walled tube of the body. A muscular-walled tube may be an artery or vein of the body. The backscatter may be emitted from one or more light sources in block 920 emitting one or more wavelengths.

The method can include, determining, by the processing device, an amount of backscatter of the light at the first wavelength (930). In one embodiment, the processing device or sensor interface may receive the detected backscatter from the optical sensor to perform the determination. In one embodiment, the processing device or optical sensor may measure light of one or more wavelengths corresponding to one or more substances in the blood stream or other tissue from one or more light sources. In one embodiment, the processing device or sensor interface will measure the amount of received backscatter of light of a wavelength between 535 nanometers and 735 nanometers corresponding to a measurement of a wavelength that is absorbed by sodium in the body. In another embodiment, the processing device or sensor interface will measure the amount of received backscatter of light of a wavelength between 680 nanometers and 880 nanometers corresponding to a measurement of a wavelength that is absorbed by potassium in the body.

The method can include comparing, by the processing device or sensor interface, the amount of backscatter of light of the first wavelength to a previous amount of backscatter of light of the first wavelength (940). In one embodiment, if the backscatter measurement of light of the first wavelength is greater than a previous measurement of backscatter of light of the first wavelength, it may indicate that that a concentration of a substance in the body that corresponds to the light of the first wavelength, such as sodium or potassium, has increased. In one example, an increase in the backscatter of light of the first wavelength may indicate that the level of potassium or sodium in the bloodstream or other tissue has decreased.

The method can include, determining, by the processing device or sensor interface, a hydration condition of the user when the amount of light that has backscattered changes (950). The hydration condition of a user is affected by the concentration of electrolytes in the body including potassium and sodium. For example, the processing device may determine that the hydration condition of the user is a dehydration condition when the amount of sodium backscatter decreases from one measurement to the next. In another example, the processing device may determine that the hydration condition of the user is a hydrated condition when the amount of sodium backscatter increases. Alternatively, the processing device may determine that the hydration condition of a user is stable if there has not been a change in backscatter.

Figure 9B:
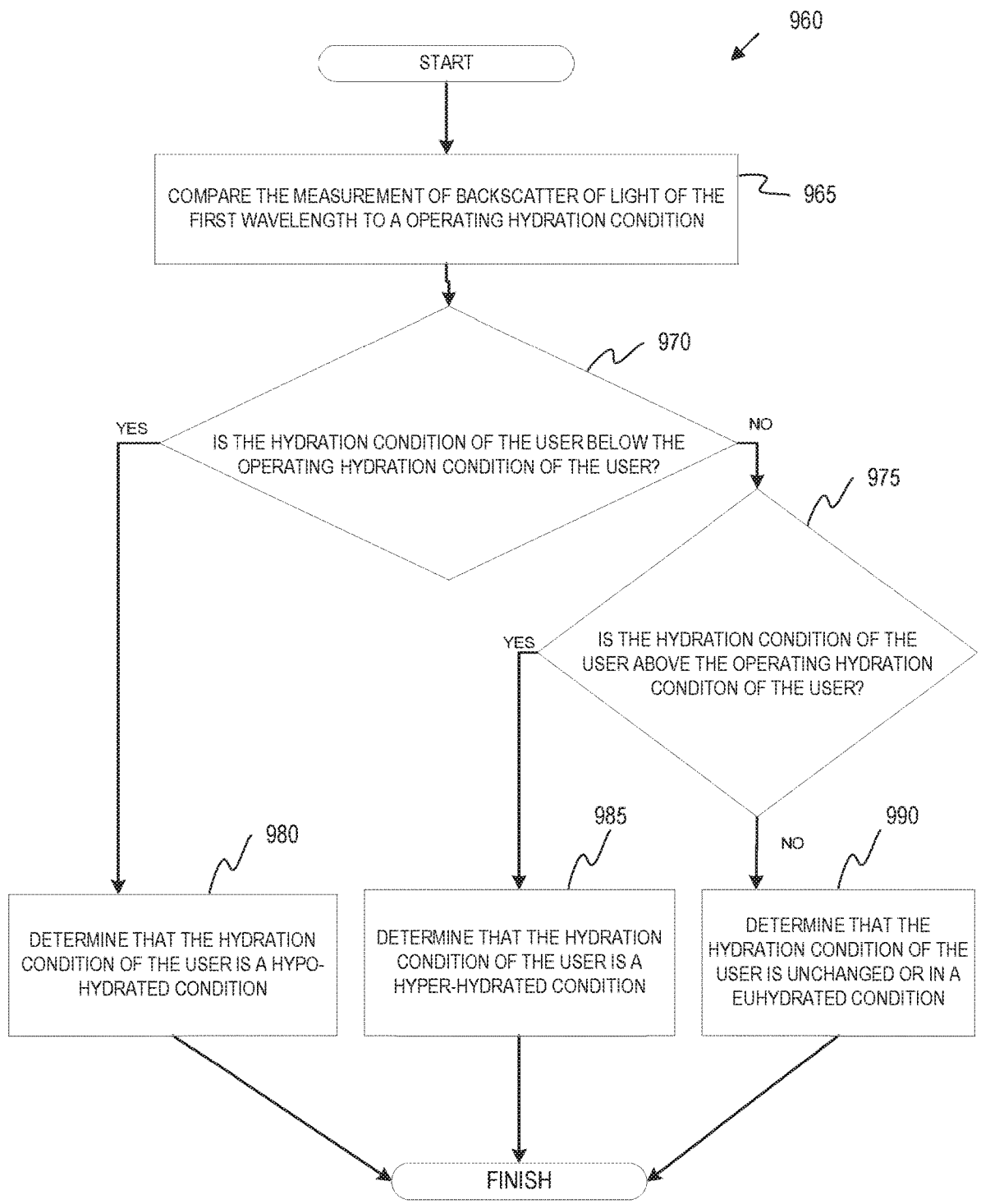
FIG. 9B illustrates a flow diagram of a method of determining a change in hydration condition of a user, according to one embodiment.

FIG. 9B illustrates a flow diagram of a method of determining a change in hydration condition of a user, according to one embodiment. The method 960 may be performed by processing logic that may include hardware (e.g., circuitry, dedicated logic, programmable logic, microcode, etc.), software (such as instruction run on a processing device, a general purpose computer system, or a dedicated machine, firmware, or a combination thereof. In one embodiment, the method 960 may be performed, in part, by processing logic of processing device 804.

For simplicity of explanation, the method 960 is depicted and described as a series of acts. However, acts in accordance with this disclosure can occur in various orders and/or concurrently and with other acts not presented as described herein. Furthermore, not all illustrated acts may be performed to implement the method 960 in accordance with the disclosed subject matter. In addition, those skilled in the art will understand and appreciate that the method 960 could alternatively be represented as a series of interrelated states via a state diagram or events.

The method begins by comparing the measurement of backscatter of light of the first wavelength to an operating hydration condition of a user to determine a hydration condition of a user (965). The first wavelength of light may correlate to a wavelength of light absorbed by a substance, such as sodium, in the blood stream or in other tissue of the body of the user. A hydration condition of the user can include a dehydrated (hypo-hydrated), normal hydration level (euhydrated), or over-hydrated (hyper-hydrated) conditions. The backscatter measurement of the first wavelength can be determined by the sensor interface as discussed in the preceding paragraphs.

The method includes, determining, by the processing device, when the hydration condition of the user is below the operating hydration condition of the user by comparing the measurement of backscatter of the first wavelength to the operating hydration condition of the user (970). In one embodiment, the operating hydration condition of the user can be determined by taking multiple measurements over a period of time and determining a range in which the user is within the user's operating hydration condition (e.g., euhydration condition).

In one embodiment, when the measurement of backscatter of light of the first wavelength is above the operating hydration condition, the processing device or sensor interface may determine that the user is in dehydrated (hypohydrated) condition (980). If the measurement of backscatter of light of the first wavelength is not below the operating hydration condition of the user, the processor may determine that the user is not in a hypo-hydrated condition. The processor may determine when the hydration condition of the user is above the operating hydration condition of the user (975). If the measurement of backscatter of light of the first wavelength above the normal operating hydration condition of the user, it may be an indicator that the user is in an over-hydrated (hyper-hydrated) condition (985). Alternatively, if the processing device or sensor interface determines that the user is neither above nor below the operating hydration condition of the user, that the user is maintaining their operating hydration condition and that the user is in a healthy hydration (euhydrated) condition (990).

Figure 10:
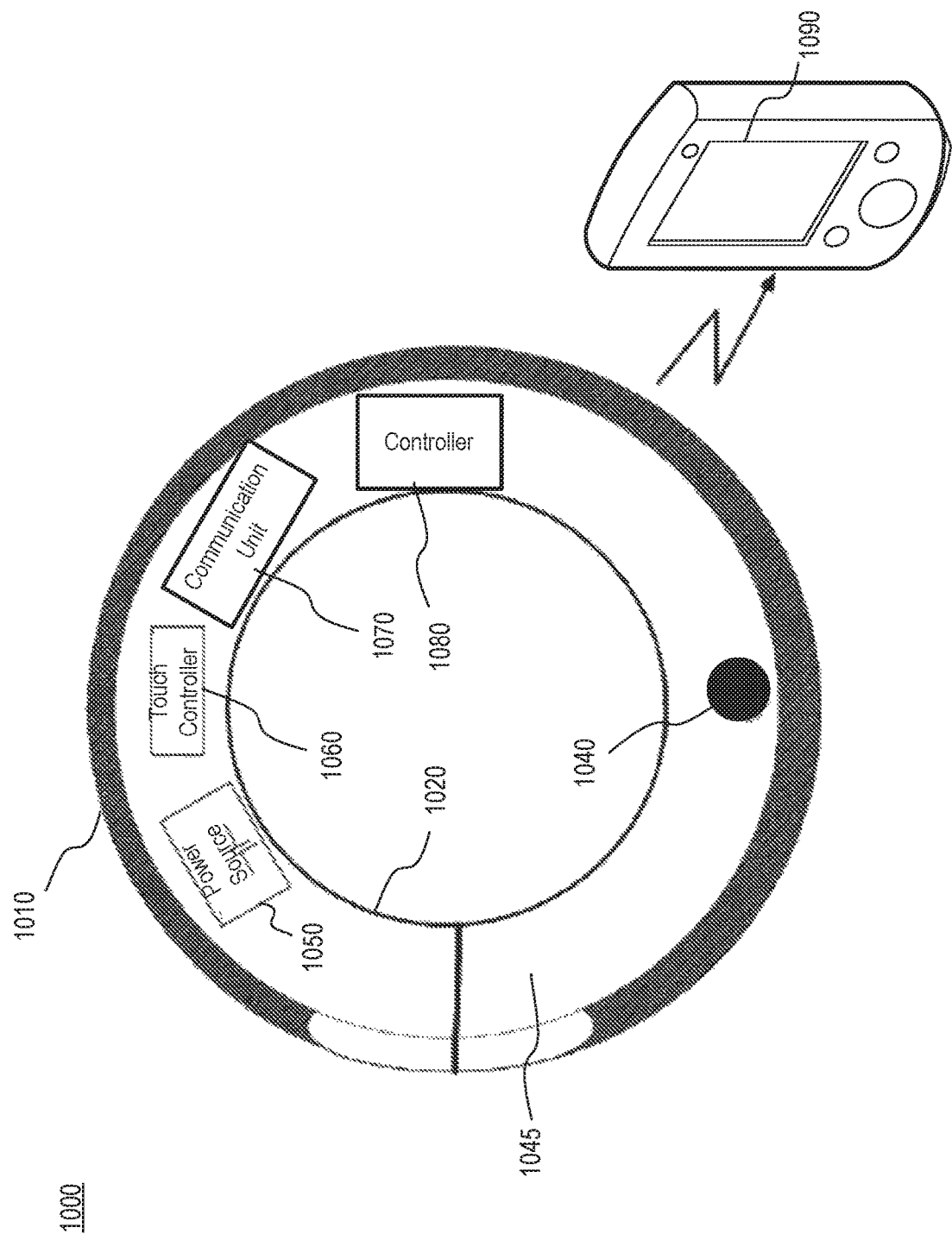
FIG. 10 depicts an electronic device communicating with an external electronic device, according to one embodiment.

FIG. 10 illustrates an electronic device 1000 communicating with an external electronic device 1090, according to one embodiment. The electronic device 1000 can be a substantially circular band with an outer surface 1010 and an inner surface 1020. In one example, the outer surface 1010 or the inner surface 1020 can be made of flexible or non-rigid material, such as rubber, polyurethane, and so forth. In another example, the outer surface 1010 or the inner surface 1020 can be made of semi-rigid or rigid material, such as plastic, metal, and so forth. In another example, a portion of the outer surface 1010 or the inner surface 1020 can be the flexible or non-rigid material and a portion of the outer surface 1010 or the inner surface 1020 can be the semi-rigid or rigid material. In another example, a portion of the inner surface 1020 that contacts a body of the user is a conductive material. For example, one or more sensors 1040 are bio-impedance sensors that are conductive rubber pads that contact the body of the user and are used by processing logic to make bio-impedance measurements.

In one example, a cavity or chamber 1045 can be between the outer surface 1010 and an inner surface 1020. The cavity or chamber 1045 can include modules, units, systems, subsystems, or devices of the electronic device 1000. For example, the cavity or chamber 1045 can house a power source 1050, a graphical user interface or touch controller 1060, a communication unit 1070, a controller 1080, one or more sensors 1040, and/or other units. In one example, the communication unit 1070 can wirelessly communicate with an external electronic device 1090. In another example, the power source 1050 can provide power to other units or modules of the electronic device 1000. In one example the touch controller 1060 can receive user input from an input device. In one example, the input device can be a graphical user interface (GUI) or a touch display and be operable to receive input via the GUI or the touch display. In another example, the input device can receive communications from other devices via a communication network (e.g., a wireless network) or a communication connection (such as a universal serial bus). In another example, the controller 1060 can control systems and subsystems of the electronic device 1000.

In another example, the power source 1050 can be a battery, such as a rechargeable battery. The power source 1050 can receive power from another power source such as via a cord plugged into a power source or using wireless power such as inductive wireless charging or resonant wireless charging. In another example, the electronic device 1000 can have one or multiple sensors 1040 (e.g., a sensor array). In one example, the multiple sensors 1040 can be different types of sensors.

In one example, the electronic device 1000 can receive physiological information such as a hydration condition and/or an environmental condition of a user of the electronic device 1000 from another device. In another example, the electronic device 1000 can have a touch controller 1060 to receive user input physiological information and/or environmental information. In one example, a power source 1050, a touch controller 1060, a communication unit 1070, a controller 1080, one or more sensors 1040 can be in direct or indirect communication with each other. For example, the touch controller 1060 receives user input information from the input device and communicates the user input information to the controller 1080. In this example, the controller 1080 can include a processor or processing device to analyze or process the user input information. In another example, the sensor 1040 can take a physiological measurement and communicate physiological information to the external electronic device 1090 via the communication unit 1070. In one embodiment, the external electronic device 1090 is an electronic device with a processor, such as a smartphone, electronic tablet, or personal computer. In another embodiment, the external electronic device 1090 is a cloud computing system or a server. The external electronic device 1090 can analyze or process data or information received from the electronic device 1000. In one example, the external electronic device 1090 can store the processed data or information. In another example, the external electronic device 1090 can send the processed data or information back to the electronic device 1000.

Figure 11:
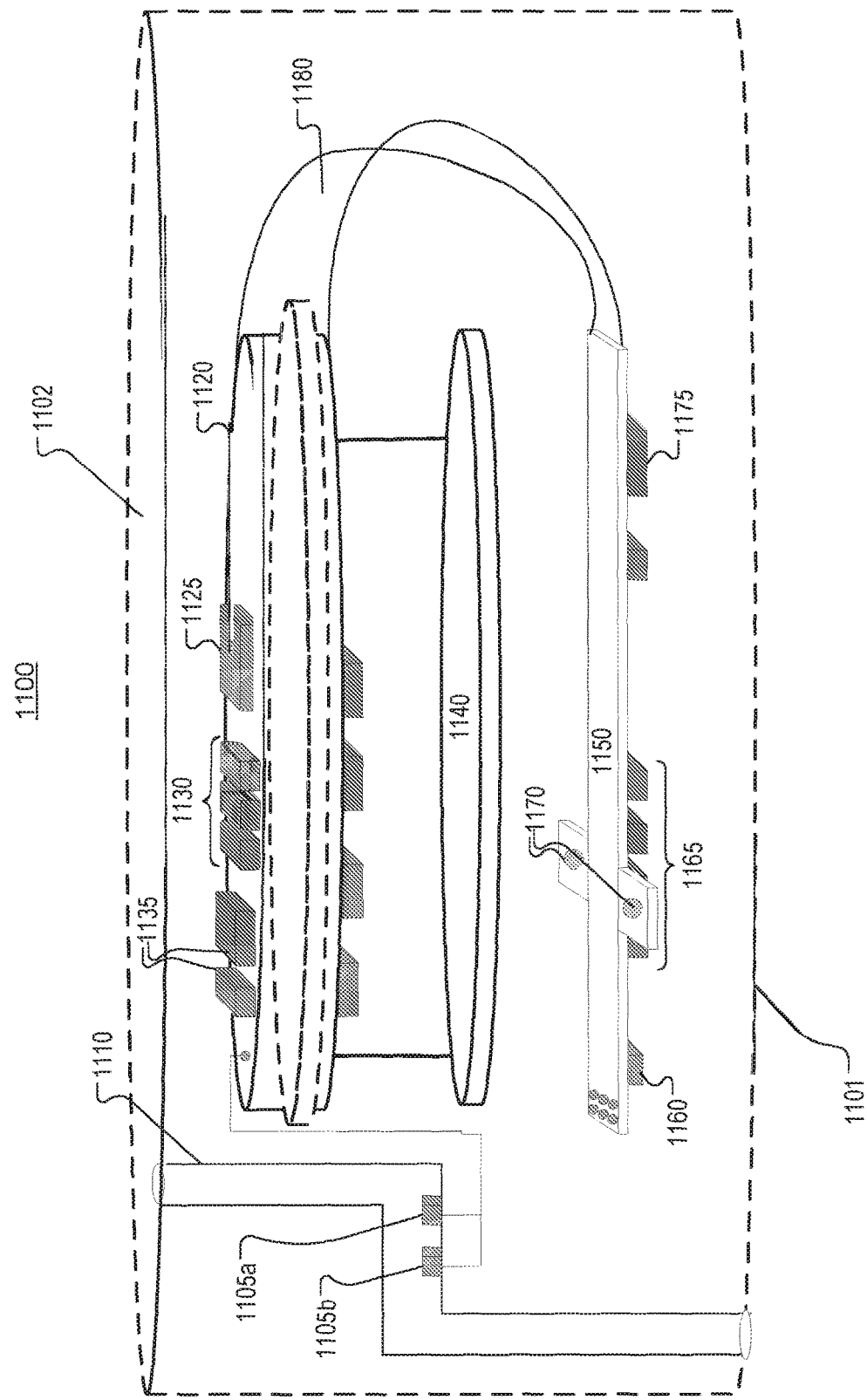
FIG. 11 depicts an interior view of the electronic device, according to one embodiment.

FIG. 11 illustrates an interior view of the electronic device 1100, according to one embodiment. The electronic device 1100 may include a bottom side 1101 and a top side 1102. In one embodiment, the electronic device 1100 may have a flume extending from the bottom side 1101 to the top side 1102. The fluke may allow humidity and/or temperature sensors 1105 to detect the humidity and temperature of both the air and the skin of the user.

In one embodiment, the electronic device 1100 may include a flexible circuit board 1180 with an upper section 1120 and a lower section 1150. The upper section 1120 of the flexible circuit board 1180 may include a motion processing unit (MPU) 1125, display LEDs or a graphical user interface 1130, and one or more communication components 1135, such as a Bluetooth Low Energy (BLE) component. In one embodiment, the MPU may detect movement of electronic device and relay motion information to the sensor interface unit 806. Additionally, display LEDs or GUI 1130 may be used to inform the user of a hydration condition. The lower section 1150 of the electronic device 1100 may include a thermistor 1175, optical components 1165 including an optical sensor and one or more light sources, impedance sensor contacts 1170, and a vibrator 1160. In one embodiment, the vibrator 1160 may be utilized to inform the user when a hydration condition has changed or to provide additional relevant information to the user.

Figure 12A:
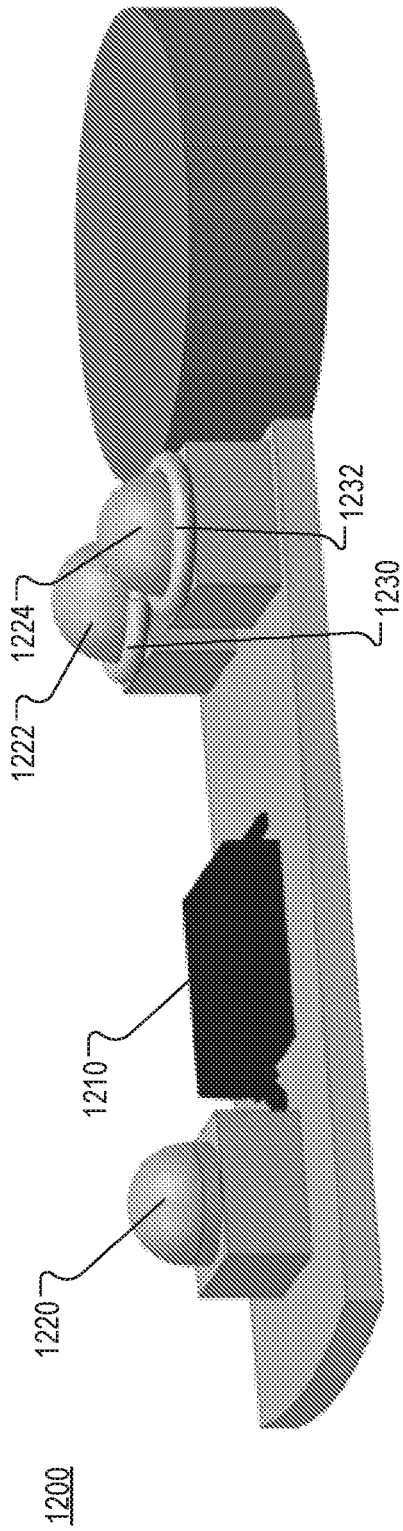
FIG. 12A depicts an optical sensor and multiple light sources embedded into the electronic device, according to one embodiment.

FIG. 12A illustrates an optical sensor 1210 and multiple light sources 1220, 1222, and 1224 embedded into the electronic device 1200, according to one embodiment. In one embodiment, the electronic device 1200 may include light sources 1220 on one side of the optical sensor 1210 and light sources 1222 and 1224 on the other side of the optical sensor 1210. In some embodiments, the light sources 1220, 1222, and 1224 may be hermetically seals, e.g. airtight, water proof, sweat proof, dust proof, and so forth. Waterproofing rings 1230 and 1232 or other sealants may be used to hermetically seal the interior of the electronic device 1200. In some embodiments, other components such as the optical sensor 1210 may be hermetically sealed using waterproofing rings or other sealants to prevent water, sweat, dust, and other debris from entering the interior of the electronic device 1200.

Figure 12B:
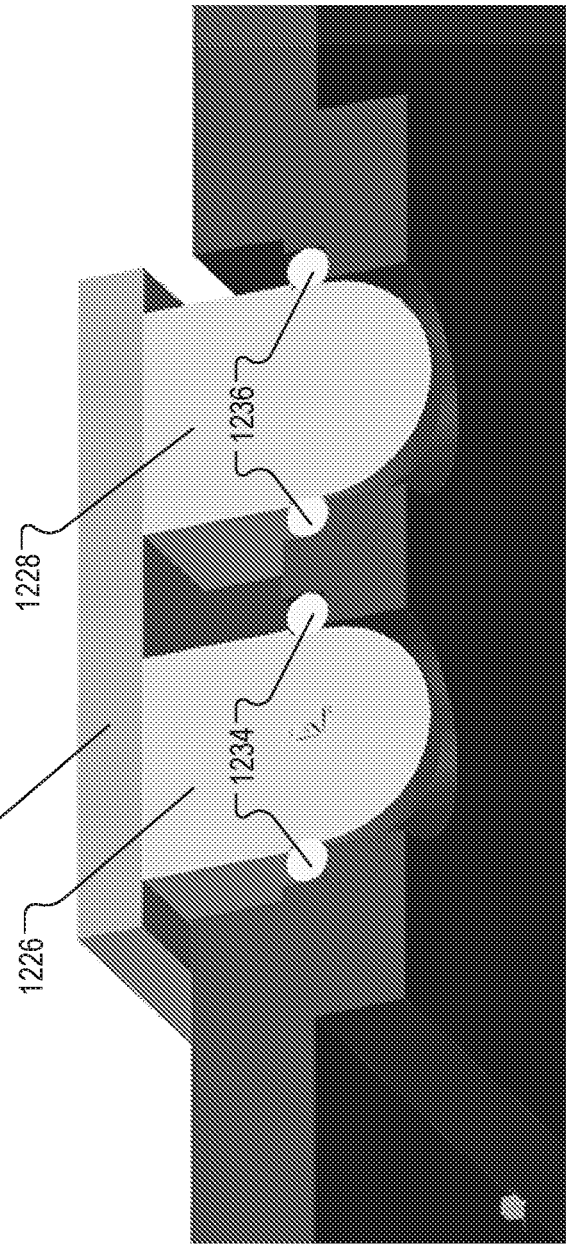
FIG. 12B illustrates a cross sectional view of multiple light sources and embedded into an electrical device, according to one embodiment.

FIG. 12B illustrates a cross sectional view of multiple light sources 1226 and 1228 embedded into an electrical device 1200, according to one embodiment. In one embodiment, light sources 1226 and 1228 may be positioned on one side of an artery or vein and may emit light of a wavelength corresponding to a wavelength absorbed by a substance of the body into the body of a user. In this example, light sources 1226 and 1228 may be hermetically sealed using waterproofing rings 1234 and 1236. Waterproofing ring 1234 and 1236 may prevent moisture from entering into the electrical device and reaching a circuit board 1240.

Figure 13:
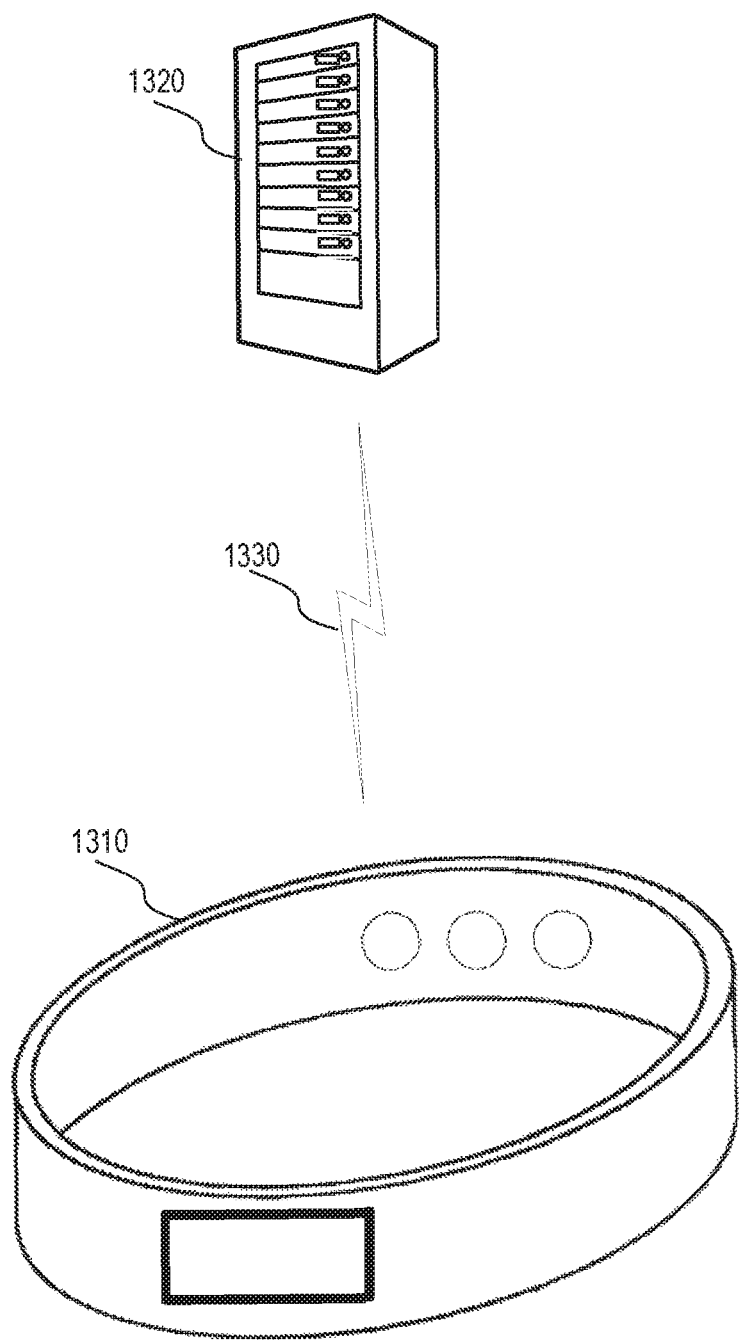
FIG. 13 depicts an electronic device in direct communications with a computing device, according to one embodiment.

FIG. 13 illustrates an electronic device 1300 in direct communications with a computing device 1320, according to one embodiment. In one example, sensor measurements collected and/or stored by the electronic device 1310 can be processed or analyzed by a processor or processing device of the electronic device 1300 and/or by a computing device 1320 in communication with the electronic device 1300. The electronic device 1300 can be in direct communication 1330 with the computing device 1320. In one example, the direct communication 1330 can be a Bluetooth® communication link, a Zigbee® communication link, radio signal, or other direct communication systems. In another example, the other computing device 1320 can be a server that stores information, such as sensor measurements or hydration condition information previously taken by the electronic device 1310 or sensor measurements or hydration condition information taken from a group of individuals, as discussed herein. In another example, the computing device 1320 can be a mobile computer device, such as a laptop computer, tablet, or a smartphone. The electronic device 1300 can communicate information, such as sensor measurements or hydration condition information, to the computing device 1320. In one example, the computing device 1320 can process and/or analyze the sensor measurements and/or information received from the electronic device 1300. In another example, the computing device 1320 can send processed data, analyzed data, measurement results, and/or other information to the electronic device 1300. In another example, the computing device 1320 can communicate calibration information to the electronic device 1310.

Figure 14:
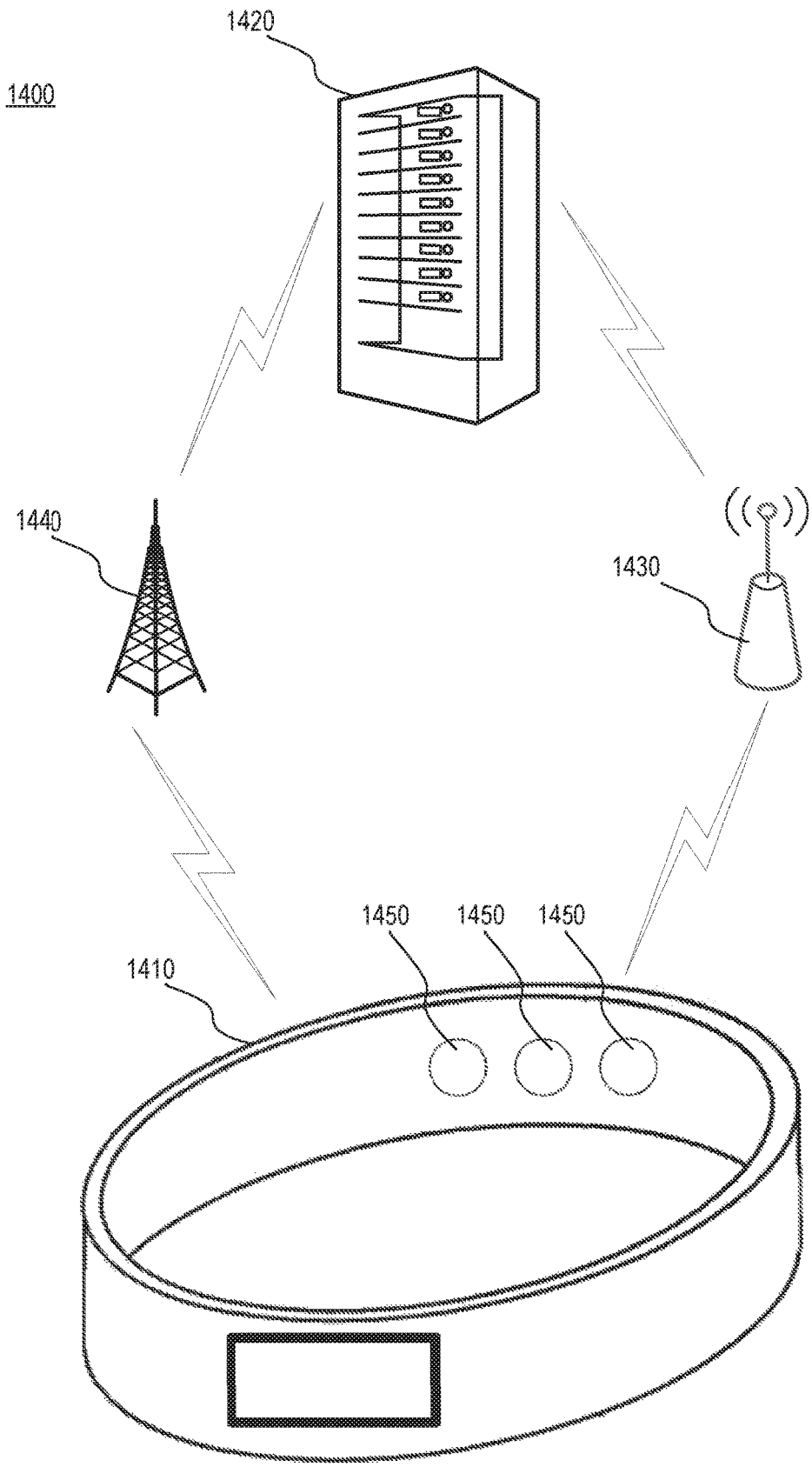
FIG. 14 depicts an electronic device and a computing device in indirect communication using a communications network, according to one embodiment.

FIG. 14 illustrates an electronic device 1400 and a computing device 1420 in indirect communication using a communications network according to one embodiment. In one embodiment, the electronic device 1400 can be a standalone device with a processing device to analyze or process: information taken from one or more sensors 1450 of the electronic device 1400; information received from other devices; and/or information stored in a memory of the electronic device 1400.

In another embodiment, the electronic device 1400 communicates locally with the computing device 1420 use a wireless communication network 1430 or a cellular communication network 1440. The local computing device 1420 can be a smartphone, tablet device, personal computer, laptop, a local server, and so forth. In another embodiment, the electronic device 1400 communicates with a non-local or remote computing device 1420 using a wireless communication network 1430 or a cellular communication network 1440. The non-local or remote computing device 1420 can be a remote server, a cloud-based server, a back-end server, or other remote electronic devices.

In one example, the wireless communication network 1430 is a cellular network employing a third generation partnership project (3GPP) release 8, 9, 10, 11, or 12 or Institute of Electronics and Electrical Engineers (IEEE) 802.16p. 802.16n, 802.16m-2011, 802.16h-2010, 802.16j-2009, 802.16-2009. In another example, the electronic device 1400 may provide a secure wireless area network (WLAN), secure PAN, or wireless fidelity (Wi-Fi) Private Wireless Wide Area Network (PWAN) to communicate with the computing device 1420. The electronic device 1400 in the WLAN may use the Wi-Fi® technology and IEEE 802.11 standards defined by the Wi-Fi Alliance® such as the IEEE 802.11-2012, IEEE 802.11 ac, or IEEE 802.11 ad standards. Alternatively, the electronic device 1400 and the computing device 1420 in the WLAN may use other technologies and standards. Similarly, the electronic device 1400 in the PAN or WPAN may use a Bluetooth® technology and IEEE 802.15 standards defined by the Bluetooth Special Interest Group, such as Bluetooth v1.0, Bluetooth v2.0, Bluetooth v3.0, or Bluetooth v4.0 (including Bluetooth low energy). Alternatively, the electronic device 1400 in the secure PAN may use other technologies and standards. In another embodiment, the communications network may be a Zigbee® connection developed by the ZigBee Alliance such as IEEE 802.15.4-2003 (Zigbee 2003), IEEE 802.15.4-2006 (Zigbee 2006), IEEE 802.15.4-2007 (Zigbee Pro). The WAN or PWAN can be used to transmit data over long distances and between different LANs, WLANs, metropolitan area networks (MANs), or other localized computer networking architectures.

The electronic device 1400 and the computing device 1420 can be in indirect communication using a communications network such as wireless communication network 1430 (such as a Wi-Fi® network) and/or using a cellular communication network 1440 (such as a 3rd Generation Partnership Project (3GPP®) network) to communicate data or measurement information. In one example, the electronic device 1400 can take sensor measurements using a sensors 1450 and communicate the sensor measurements to the computing device 1420 via the wireless communication network 1430 and/or the cellular communication network 1440. In another example, the computing device 1420 can receive sensor measurements from the electronic device 1400 via the wireless communication network 1430 and/or the cellular communication network 1440 and process the sensor measurements and/or analyze the sensor measurements. When the computing device 1420 has processed the sensor measurements and/or analyzed the sensor measurements, the computing device 1420 can communicate the processed sensor measurements, analyzed sensor measurements, sensor measurement results, or other information to the electronic device 1400 via the wireless communication network 1430 and/or the cellular communication network 1440.

FIG. 15 depicts a body area network (BAN) devices 1562-1576 communicating using a BAN, according to one embodiment. In one embodiment, the BAN can include a wired body area network, a wireless body area network (WBAN), and/or a body sensor network (BSN). The BAN can include multiple wearable computing devices or wearable sensor devices 1562-1576 that are in communication with each other to send and receive data and information. In one example, the BAN devices can include: a BAN device 1560 that is attached or coupled to the body of the user, an BAN device 1562 that is implanted into the body of the user; a BAN device 1568 that is embedded into the body of a user, a BAN device 1570 that is mounted on a surface of the body, and so forth. In another example, the BAN devices can include devices adjacent the user including: a BAN device 1564 shaped to fit in a clothes pockets of the user, a BAN device 1566 that a user can carry, such as a handheld device; a BAN device 1572 that is integrated into clothes of the user, a BAN device 1576 located in a user's bag, a BAN device 1574 integrated into a user's bag, and so forth. In one embodiment, an electronic device is a BAN device. In another embodiment, the BAN devices 1562-1576 can be body sensor units (BSUs) that include a processing device, a sensor, and a communication device. The BSUs can communicate with a body central unit (BCU) 1578 that is a hub for the BAN devices. The BCU 1578 can be located at any of the locations discussed above for the BAN devices 1562-1576. The BCU 1578 can include a processing device, memory, a communication device, and a display. The BCU 1578 can receive data from a BAN device 1562-1576 and analyze the data. In one example, the BCU 1578 can display the analyzed data using the display of the BCU 1578. In another example, the BCU 1578 can send the analyzed data to a BAN device 1562-1576 or another device. One advantage of the BCU 1578 communicating with the BAN devices 1562-1578 is that the BAN devices 1562-1578 can be configured to be minimal sensor devices with low power consumption and a compact design where the BCU 1578 performs the processing of the data.

In another embodiment, the BCU 1578 can be a data hub or data gateway to manage the BAN devices 1562-1576. In another embodiment, the BCU 1578 can provide a user interface to control the BAN devices 1562-1576. In another embodiment, the BAN devices 1562-1576 and/or the BCU 1578 can use wireless private area networks (WPAN) technology as a gateway or relay to reach longer ranges. In one example, the BCU 1578 can us a WPAN to connect the BAN device 1562-1576 on the body to the internet. For example, medical professionals can access patient data from the BAN devices 1562-1576 online using the internet independent of a location of a patient.

Figure 16:
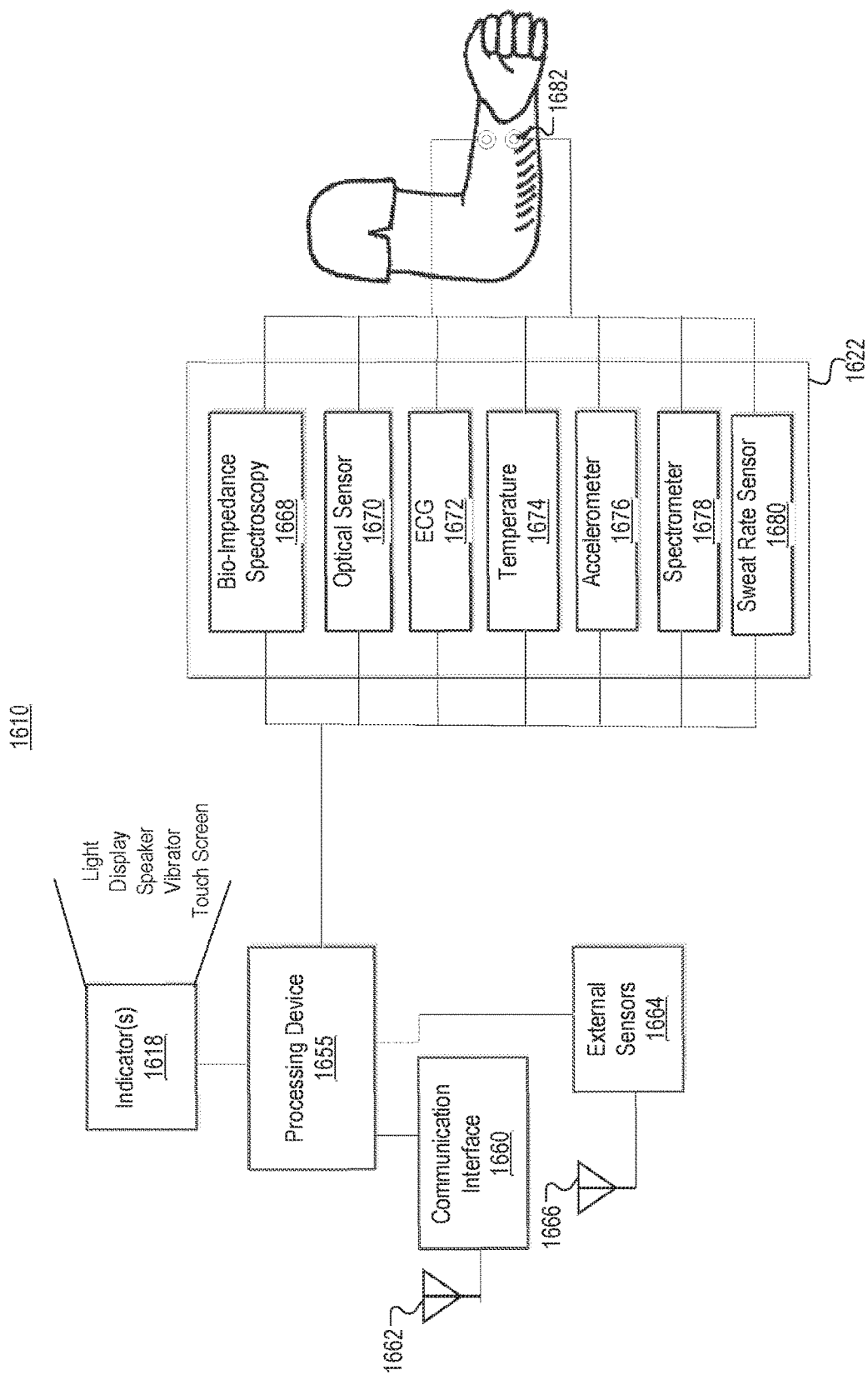
FIG. 16 depicts a schematic view of an electronic device, according to one embodiment

FIG. 16 depicts a schematic view of an electronic device 1610, according to one embodiment. The electronic device 1610 may include the indicators 1618, a sensor array 1622 (to include at least one of the sensors in FIG. 1, 2, 4, 5, or 7), a processing device 1655, a communications interface 1660, an antenna 1662 coupled with the communications interface 1660, external sensors 1664, and accompanying antenna(s) 1666. In one example, the sensor array 1622 may include one or more physiological sensors to take physiological measurements (e.g., measurements related to the body of the individual or animal). The sensor array 1622 may include one or more sensors to engage a user of the electronic device to take measurements. In various examples, the sensor array 1622 may include, without limitation: a bio-impedance spectroscopy sensor 1668 (or simply impedance sensor 1668), an optical sensor 1670, an electrocardiogram (ECG) sensor 1672, a temperature sensor 1674 (such as a thermometer or thermistor), an accelerometer 1676, a spectrometer 1678, a sweat rate sensor 1680, and so forth. In one example, the sensor array 1622 can contact or engage the body of the user at a location 1682.

Figure 17:
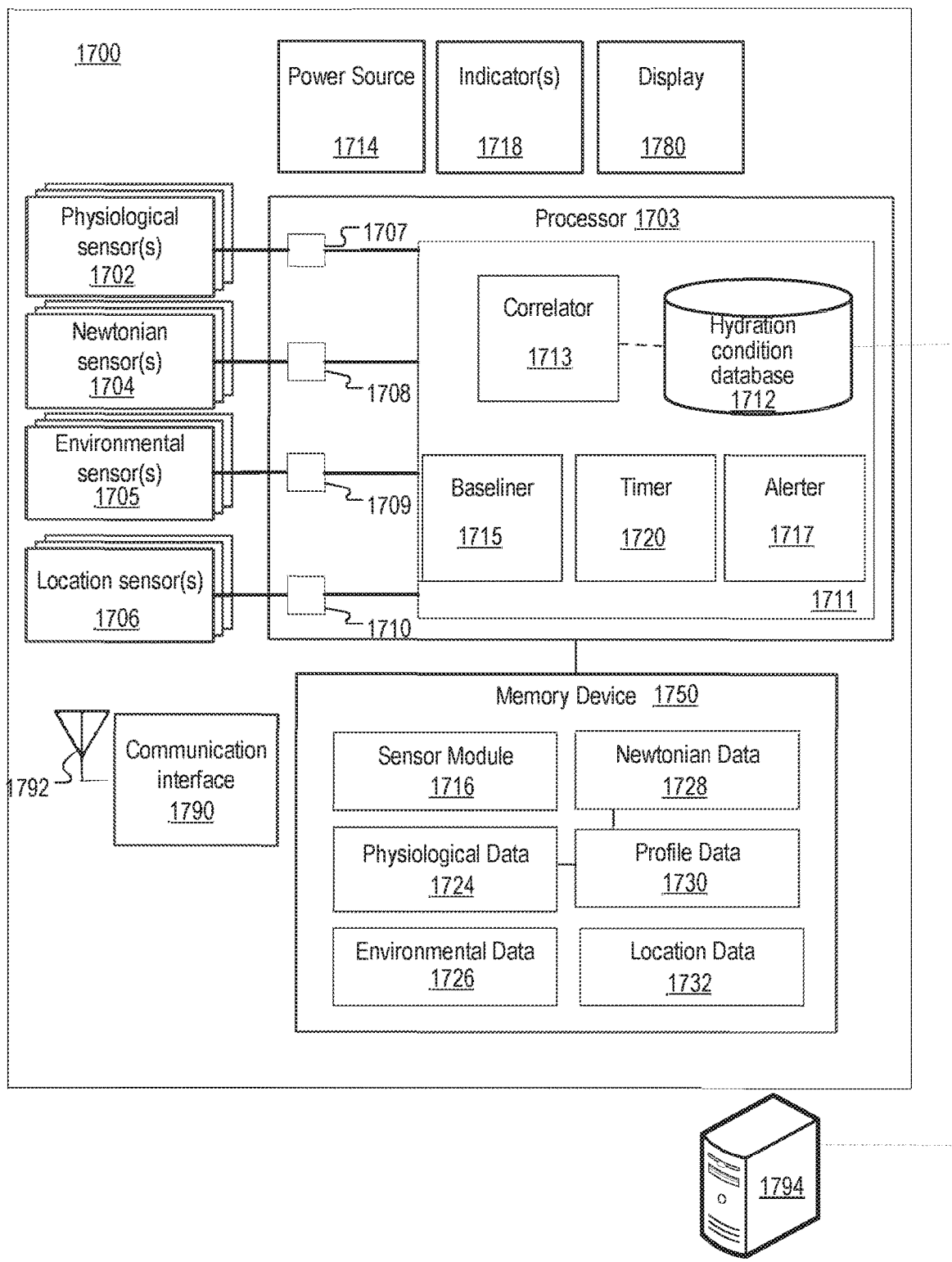
FIG. 17 is a block diagram of the electronic device with a correlator, a baseliner, and an alerter, according to one embodiment.

FIG. 17 is a block diagram of the electronic device 1700 with a correlator 1713, a baseliner 1715, and an alerter 1717, according to one embodiment. The electronic device 1700 may include, without limitation, one or more physiological sensor(s) 1702, one or more Newtonian sensor(s) 1704, one or more environmental sensor(s) 1705, one or more location sensor(s) 1704, a processor 1003, a memory device 1708, a display 1780, a communication interface 1790 (such as a radio frequency (RF) circuit), and an antenna 1792 coupled to the communication interface 1790.

In one embodiment, the communication interface 1790 may communicate, via the antenna 1792, with an external electronic device 1090 (illustrated in FIG. 10), a computing device 1320 or 1420 (illustrated in FIGS. 13 and 14), and with other wireless devices. In one example, the communication interface 1790 may communicate the information using a cellular network, a wireless network, or a combination thereof. In one example, the communications network can be a cellular network employing a third generation partnership project (3GPP) release 8, 9, 10, 11, or 12 or Institute of Electronics and Electrical Engineers (IEEE) 802.16p, 802.16n, 802.16m-2011, 802.16h-2010, 802.16j-2009, 802.16-2009. In another example, the electronic device 1700 may provide a secure wireless area network (WLAN), secure PAN, or wireless fidelity (Wi-Fi) Private Wireless Wide Area Network (PWAN) to communicate with a device. The electronic device 1700 in the WLAN may use the Wi-Fi® technology and IEEE 802.11 standards defined by the Wi-Fi Alliance® such as the IEEE 802.11-2012, IEEE 802.11 ac, or IEEE 802.11 ad standards. Alternatively, the devices in the WLAN may use other technologies and standards. Similarly, the electronic device 1700 in the PAN or WPAN may use the Bluetooth® technology and IEEE 802.15 standards defined by the Bluetooth Special Interest Group, such as Bluetooth v1.0, Bluetooth v2.0, Bluetooth v3.0, or Bluetooth v4.0. Alternatively, the electronic device 1700 in the secure PAN may use other technologies and standards. In another embodiment, the communications network may be a Zigbee® connection developed by the ZigBee Alliance such as IEEE 802.15.4-2003 (Zigbee 2003), IEEE 802.15.4-2006 (Zigbee 2006), IEEE 802.15.4-2007 (Zigbee Pro). The WAN or PWAN can be used to transmit data over long distances and between different LANs, WLANs, metropolitan area networks (MANs), or other localized computer networking architectures.

In one embodiment, the electronic device 1700 can communicate data with the other devices via another device, such as a smartphone or tablet computing device. For example, the communication interface 1790 can pair with a smartphone via the wireless network. The smartphone can receive data using the wireless network and can communicate the data to the other device. In another embodiment, the electronic device 1700 may communicate information with the other device via repeaters or a relay system. For example, a user of the electronic device 1700 can be outside a coverage area for the cellular network or the wireless network, e.g., a farm worker out in the field. In this example, the electronic device 1700 can determine that it is outside the coverage area and switch to communicating via the repeaters or the relay system.

In one embodiment, the electronic device 1700 can determine it is outside a coverage area when it does not receive a signal from the cellular network or the wireless network. In another embodiment, the electronic device 1700 can ping the cellular network or the wireless network (such as a tower within the cellular network or the wireless network) and determine that it is outside the coverage area when the electronic device 1700 does not receive a reply to the ping. In another embodiment, multiple electronic devices 1710 can communicate with each other to form a piconet. In this embodiment, a first electronic device can determine it is outside the coverage area and can scan for a second electronic device, where the second electronic device is in the coverage area or in communication with another electronic device in the coverage area. When the first wearable safety finds the second electronic device, the electronic device can communicate information to an end device or to the cellular network or the wireless network via the second electronic device.

The processor 1703 may include a first sensor interface 1707 for receiving sensor data from the physiological sensor(s) 1702, a second sensor interface 1708 for receiving sensor data from the Newtonian sensor(s) 1704, a third sensor interface 1709 for receiving sensor data from the environmental sensor(s) 1705, a fourth sensor interface 1710 for receiving sensor data from the location sensor(s) 1706, and a processing element 1711. The processing element 1711 in turn may include a correlator 1713, a baseliner 1715 and/or an alerter 1717. The memory device 1708 may also include, without limitation, a sensor module 1716, physiological data 1724, environmental data 1726, Newtonian data 1728, and profile data 1730, location data 1732.

The electronic device 1700 may include the sensor array 120 (FIG. 1) with two or more sensors. In the depicted embodiment, the electronic device 1700 may include one or more physiological sensors 1702, one or more Newtonian sensors 1704, one or more environmental sensors 1705, one or more location sensors 1706, or a combination thereof. In some instances, the Newtonian sensors 1704 may be physiological sensors. That is, in some embodiment, the activity level may be determined from one or more physiological measurements.

A physiological measurement may be any measurement related to a living body, such as a human's body or an animal's body. The physiological measurement is a measurement made to assess body functions. Physiological measurements may be simple, such as the measurement of body or skin temperature, or they may be more complicated, for example measuring how well the heart is functioning by taking an ECG (electrocardiograph), or determining a hydration condition of the body. Physiological measurements may also include motion and/or movement of the body. In some cases, these physiological measurements may be taken as an aggregate. e.g., as physiological data, with which to correlate to other physiological measurements, a physiological parameter, and/or an environmental parameter.

A parameter may be considered a measurable quantity (such as heart rate, temperature, altitude, and oxygen level, as just a few examples). When measurements of parameters are taken in the aggregate, the measurements may form data which may be analyzed and correlated to other data or parameters, to identify trends or to identify when meeting (or exceeding) certain thresholds that trigger alerts or other actions and the like.

The physiological sensors 1702 may include a pulse oximeter sensor, an electrocardiography (ECG) sensor, a fluid level sensor, an oxygen saturation sensor, a body core temperature sensor, a skin temperature sensor, a plethysmograph sensor, a respiration sensor, a breath rate sensor, a cardiac sensor (e.g., a blood pressure sensor, a heart rate sensor, a cardiac stress sensor, or the like), an impedance sensor (e.g., bio-impedance spectroscopy sensor), an optical sensor, a spectrographic sensor, an oxygen saturation sensor, or a sweat rate sensor. Alternatively, other types of sensors may be used to measure physiological measurements, including measurements to determine activity levels of a person wearing the electronic device.

The Newtonian sensors 1704 may be any of the physiological sensors described above, but in some cases, the Newtonian sensors 1704 are activity or motion sensors, such as, for example, a gyroscope sensor, a vibration sensor, an accelerometer sensor (e.g., a sensor that measures acceleration and de-acceleration), a three dimensional (3D) accelerometer sensor (e.g., sensors that measure the acceleration and de-acceleration and the direction of such acceleration and de-acceleration), a force sensor, a pedometer, a strain gauge, a magnetometer, and a geomagnetic field sensor that may be used for activity level measurements; whereas the physiological sensors 1702 may be used for specific physiological measurements.

In one embodiment, an environmental measurement may be any measurement of an area approximate or adjacent a user. The environmental sensors 1705 may be a humidity sensor, an ambient temperature sensor, an altitude sensor, a barometer, and so forth. A location measurement may be any measurement of a location of the user or a movement of the user. The location sensor 1706 may be a global positioning system (GPS), a triangulation system, or a location sensor. One or a combination of the physiological data 1724, the environmental data 1726, the Newtonian data 1728, the profile data 1730, and the location data 1732 may be obtained from other sources such as through network from sources reachable in the cloud or online.

In another embodiment, the environmental measurement can be any measurement of a local or central location measurement of where a user is located. For example, one or more environmental sensors 1705 may be located at a location within a threshold radius of the user, such as a threshold radius from the user location. In this example, the environmental sensors 1705 can take environmental measurements and relay the information to the electronic device 1700 or to a communication hub that has a communication channel established with the electronic device 1700. Alternatively, the environmental sensors 1705 can take environmental measurements and relay the information to a processing hub that can analyze the environmental measurements to determine selected environmental factors (such as a humidity level, a heat index, and so forth) and can communicate the environmental factors to the electronic device 1700 or to another electronic device. In another embodiment, the processing hub can receive the environmental measurements from the environmental sensors 1705 and other measurements (such as physiological measurements) from the electronic device 1700. The processing hub can analyze the environmental measurements and the other measurements to determine selected result data, such as a hydration level of a user or a health level of the user. In another embodiment, the electronic device 1700 can take a first set of environmental measurements and the local environmental sensors 1705 can take a second set of environmental measurements. The first set of environmental measurements and the set of environmental measurements can be combined or aggregated and the processing hub and/or the electronic device 1700 can analyze the aggregated environmental measurements.

In another embodiment, the environmental measurements can be from an environmental information outlet or provider. For example, the environmental information outlet or provider is a weather station, a news station, a television station, an online website, and so forth. The electronic device 1700 or the processing hub can receive the environmental information from the environmental information outlet or provider can use the environmental information to determine selected physiological and/or environmental data or factors.

The first sensor interface 1707 may be coupled with the one or more physiological sensors 1702, a second sensor interface 1708 may be coupled with the one or more Newtonian sensors 1704, a third sensor interface 1709 may be coupled with the one or more environmental sensors 1705, and a fourth sensor interface 1710 may be coupled with the one or more location sensors 1706. The processing element 1711 may be operable to execute one or more instructions stored in the memory device 1708, which may be coupled with the processor 1703. In some cases the processing element 1711 and memory device 1708 may be located on a common substrate or on a same integrated circuit die. Alternatively, the components described herein may be integrated in one or more integrated circuits as would be appreciated by one having the benefit of this disclosure. The memory device 1708 may be any type of memory device, including non-volatile memory, volatile memory, or the like. Although not separately illustrated the memory device may be one or more types of memory configured in various types of memory hierarchies.

The memory device 1708 may store physiological data 1724, such as current and past physiological measurements, as well as profile data 1730, including user profile data, bibliographic data, demographic data, and the like. The physiological data 1724, and in some cases the profile data 1730, may also include processed data regarding the measurements, such as statistical information regarding the measurements, as well as data derived from the measurements, such as predictive indicators, results, and/or recommendations.

In one example, the profile data 1730 may also include information connected to user profiles of the users that wear the electronic device 1700, such as a gender of the user, an age of the user, a body weight or mass of the user, a health status of the user, a fitness level of the user, or a family health history of the user. In another example, the profile data 1730 can include occupational information of the users that wear the electronic device 1700, such as a job type, a job title, whether the job is performed indoors or outdoors, a danger level of the job, and so forth. For example, the job types can include an elderly live-at-home job, an oil driller, a construction worker, a railroad worker, a coal mine worker, a job in confined spaces, a fireman, a construction worker, an outdoor worker, an office worker, a truck driver, a child, or a disabled individual.

In one example, the electronic device 1700 can receive the profile data 1730 via a touch screen device integrated into the electronic device 1700 or coupled to the electronic device 1700. In another example, the electronic device 1700 can receive the profile data 1730 via a communication port of the electronic device 1700. For example, the electronic device 1700 can receive profile data 1730 from another device via a wired communication connection (e.g., a universal serial bus) or via a wireless communication connection (e.g., a Bluetooth® communication technology).

The profile data 1730 may also be linked to various physiological data 1724 and Newtonian data 1728 and be tracked over time for the users. The profile data 1730 may also include baselines of physiological parameters for respective users. In one example, the baselines are of a heart rate, a blood pressure, bio-impedance, skin temperature, oxygen levels, hydration levels, electrolyte levels and so forth. When the baselines are included with the user profiles, the user profiles may be referred to as baseline profiles for the respective users.

The memory device 1708 may also store one or a combination of the environmental data 1726, the Newtonian data 1728, the profile data 1730, and the location data 1732. The Newtonian data 1728, environmental data 1726, or location data 1732 may be current and past measurements, as well predictive data for predictive modeling of activity levels, environmental levels, or locations. The memory device 1708 may store instructions of the sensor module 1716 and instructions and data related to the correlator 1713, the baseliner 1715 and the alerter 1717, which perform various operations described below.

In particular, the sensor module 1716 may perform operations to control the physiological sensors 1702, Newtonian sensors 1704, environmental sensors 1705, and location sensors 1706, such as when to turn them on and off, when to take a measurement, how many measurements to take, how often to perform measurements, etc. For example, the sensor module 1716 may be programmed to measure a set of physiological measurements according to a default pattern or other adaptive patterns to adjust when and how often to take certain types of measurements. The measurements may be stored as the physiological data 1724, the environment data 1726, and the Newtonian data 1728, location data 1732, and some of them may also be integrated as a part of the profile data 1730, as discussed.

In the depicted embodiment, the processing element 1703 (e.g., one or more processor cores, a digital signal processor, or the like) executes the instructions of the sensor module 1716 and those related to the correlator 1713, the baseliner 1715, the alerter 1717 and possibly other modules or routines. Alternatively, the operations of the sensor module 1716 and the correlator 1713, the baseliner 1715, and the alerter 1717 may be integrated into an operating system that is executed by the processor 1703. In one embodiment, the processing element 1711 measures a physiological measurement via the first sensor interface 1707. The processing element 1711 may measure an amount of activity of the electronic device 1700 via the second sensor interface 1709. The amount of activity could be movement or motion of the electronic device 1700 (e.g., by tracking location), as well as other measurements indicative of the activity level of a user, such as heart rate, body temperature, skin luminosity, or the like. The processing element 1711 measures an environmental measurement via the third sensor interface 1709. The processing element 1711 measures a location measurement via the fourth sensor interface 1710.

In one embodiment, the Newtonian sensors 1704 may include a hardware motion sensor to measure at least one of movement or motion of the electronic device 1700. The processing element 1711 may determine the amount of activity based the movement or motion of the electronic device 1700. The hardware motion sensor may be an accelerometer sensor, a gyroscope sensor, a magnetometer, a GPS sensor, a location sensor, a vibration sensor, a 3D accelerometer sensor, a force sensor, a pedometer, a strain gauge, a magnetometer, and a geomagnetic field sensor.

The processor 1703 may further execute instructions to facilitate operations of the electronic device 1700 that receive, store and analyze measurement data, environmental data, location data, and profile data. The indicator(s) 1718 may include one or more of a light, a display, a speaker, a vibrator, and a touch display, useable to alert the user to take actions in response to trending levels of: physiological parameters during or after physical activity and/or prepare for undertaking anticipated physical activity; environmental parameters; activity parameters, or location parameters.

In some embodiments, for example, the correlator 1713 may analyze measurement data to correlate physiological data, environmental data, activity data, location data, or user experienced feedback with a physiological parameter, environmental parameter, activity parameter, a location parameter, or user experienced feedback to predict a change in a level of the physiological parameter, environmental parameter, activity parameter, or a location parameter. In one embodiment, the user experienced feedback can be physiological or psychological symptoms experienced by the user. For example the physiological or psychological symptoms can include: headaches, dizziness, tiredness, mental fatigue, increased thirst, dry mouth, swollen tongue, physical weakness, confusion, sluggishness, and so forth.

Such prediction may enable timely and accurate recommendations to a user in terms of hydrating, adjusting effort levels or other specific actions to address a trend or a change in the physiological parameter, the environmental parameter, the activity parameter, or the location parameter. The recommendations may be displayed in the display 1780, sent via an alert through one of the indictor(s) 1718 or displayed in another device such as a smart phone or tablet or other computing device.

In another embodiment, the correlator 1713 may also track and analyze Newtonian data of the user related to physiological or determined parameters (such as heart rate, oxygenation, skin luminosity, hydration, and the like), related to location and type of activity (such as activity levels associated with being at the gym, riding a bike, attending class, working at a desk, sleeping, or driving in traffic, and the like) and/or related to scheduling information (such as appointments on a calendar, invites received from friends, or messages related to travel and/or activity plans, and the like). Through this analysis, the electronic device 1700 may track activity data over time, intelligently and continuously (or periodically) analyze all of this information, and alert the user through the indicator(s) 1718 to take a specific action at a proper time before a start of a dehydration condition. The specific action may include to hydrate extra hours before physical activity and to eat at least two hours before any physical activity, or other such timing that may be general to most users, or customized to a training or nutrition routine of a specific user.

In another embodiment, the correlator 1713 can build an individualized profile for the user. The correlator 1713 can receive the individualized profile information from an input device of the electronic device 1700. For example, the correlator 1713 can receive the individualized profile information from a touch screen of the electronic device 1700. In another example, the correlator 1713 can receive the individualized profile information from a device in communication with the electronic device (such as via a USB port or using a Bluetooth® technology). In another embodiment, the electronic device 1700 can include a memory that stores the individualized profile information for the user.

The individualized profile can include physiological information associated with the user. For example, the physiological information can include a hydration condition, an average heart rate of the user, an age of the user, a health level of the user, and so forth. The individualized profile can also include information associated with a location or environment that the user is located. For example, the individualized profile can include: humidity level information, such as when the user is located in a dry climate or in a humid climate; altitude level information, such as when the user is located at a relatively high altitude or a relatively low altitude; seasonal information, such as if it is winter where the user is located or summer. The correlator 1713 can also determine an environmental effect on the user for the location where the user is located at. For example, if the user is located at their home that is at a high altitude with a dry climate and it is a winter season, the correlator 1713 can determine that the user is acclimated to high altitudes, dry climates, and the winter season. The correlator 1713 can also update the user profile when the user changes location. For example, when the user leaves their home location and goes on a vacation to a location that is at a low altitude, a humid climate, and it is a summer season, the correlator 1713 can determine that the user is not acclimated to the low altitude, humid climate, and summer season.

In one embodiment, the electronic device 1700 can alert the user of the changes to the individualized profile. In another embodiment, the electronic device 1700 can alert the user of the changes to effects associated with the changes to the individualized profile. For example, the electronic device 1700 can access a table of predetermine effects of the user changing their user profile. In one example, the table can indicate that when the user switches from a low altitude to a high altitude location, the user may experience altitude sickness. In another example, the table can indicate that when the user switches from a dry climate to a humid climate location, an ability of the user's body to cool itself down when an ambient temperature is relatively high. In another embodiment, the table can indicate when the current user profile indicates safety risks or physiological performance changes.

In another embodiment, the individualized profile can also include information associated with clothing or apparel worn by the user of the electronic device 1700. For example, the individualized profile can indicate that a user may wear different types of apparel for different environments including: a thickness of fabric; a type of a fabric, such as wool or cotton; a number of clothes layers worn by the client; accessories worn by the client, such as hard hats, steeled toed shoes, safety goggles, safety belts, and so forth; and gender types of apparel, such as women and men's apparel. In one example, the correlator can adjust measurement information or measurement results based on the different types of clothing or apparel. For example, the correlator 1713 can determine that the user is a firefighter and is wearing multiple layers of clothing to protect against fire. In this example, the correlator 1713 can determine that a cause of a hydration level of the user decreasing is the multiple layers of clothing cause the firefighter to sweat more and loss more fluid than a typical number of layers of clothing worn by the user.

In one embodiment, the alerter 1717 may decide the most appropriate timing and mode of alert, whether through one of the indicator(s) 1718, the display 1780 or another device such as a smart phone, tablet or the like. The type of indicator used to alert the user may also be customized to or by the user.

In one embodiment, the correlator 1713 may determine a correlation between different data points or data sets of the input data (such as data collected from different sensors, devices, or obtained from the cloud or online). The correlator 1713 may determine different types of correlations of the data points or data sets. In one example, the correlator 1713 may execute a Pearson product moment correlation coefficient algorithm to measure the extent to which two variables of input data may be related. In another example, the correlator 1713 may determine relations between variables of input data based on a similarity of rankings of different data points. In another example, the correlator 1713 may use a multiple regression algorithm to determine a correlation between a data set or a data point that may be defined as a dependent variable and one or more other data sets or other data points defined as independent variables. In another example, the correlator 1713 may determine a correlation between different categories or information types in the input data.

In further examples, when the correlator 1713 determines a correlation between the different data points or data sets, the correlator 1713 may use the correlation information to predict when a first event or condition may occur based on a second event or condition occurring. In another example, when the correlator 1713 determines a correlation between the different data points or data sets, the correlator 1713 may use the correlation information to determine a hydration condition. As discussed in the preceding paragraphs, a hydration can be an event that negatively impacts a user's safety or health. In another example, when the correlator 1713 determines a correlation between the different data points or data sets, the correlator 1713 may use the correlation information to determine a cause of a condition and/or event, such as a hydration condition.

Additionally, or alternatively, the correlator 1713 may determine a correlation between physiological data 1724, environmental data 1726, Newtonian data 1728, profile data 1730, and location data 1732. For example, the input data may include hydration level data (physiological data) and ambient temperature data (environmental data). In this example, the correlator 1713 may identify a correlation between an increase in the ambient temperature, a decrease in a hydration level of a user, and a heat stroke. The correlator 1713 may identify the correlation between the ambient temperature, the hydration level, and the heat stroke by using a regression algorithm with the heat stroke as an independent variable and the ambient temperature and the hydration level as dependent variables. When the correlator 1713 has identified the correlation between the heat stroke, the ambient temperature, and the hydration level, the correlator 1713 may predict a heat stroke based on a change in a hydration level of a user or a rate of change of a hydration level of a user and a change in the ambient temperature or a rate of change in the ambient temperature.

Additionally, or alternatively, the correlator 1713 may determine a correlation between a fatigue event, an altitude level, and an oxygenation level of a user. For example, the correlator 1713 may determine a correlation between an increase in the altitude level, a decrease in the oxygenation level of the user, and an increase in a fatigue event. When the correlator 1713 determines the correlation between the altitude level, the oxygenation level, and the fatigue event, the correlator 1713 may predict an increase or decrease in a probability of a hydration condition change based on a change in the oxygenation level of user and the altitude level at which the user is currently at. In one example, the correlator 1713 can use the individualized profile information (as discussed in the preceding paragraphs) of the user to determine the predicted increase or decrease in the probability of a hydration condition change. For example, the correlator 1713 can determine a change in altitude level of the user from a relatively low altitude to a relatively high altitude. The correlator 1713 can use the individualized profile information to determine that the user is acclimated to the relatively high altitude (such as if they live at a high altitude) and adjust the predicted increase or decrease in the probability of a hydration condition change for the change in altitude in view of the individualized profile information. For example, the correlator 1713 can predict that the change from the low altitude to the high altitude will not increase or decrease the probability of a user becoming dehydrated.

In a further example, the correlator 1713 may identify a correlation between location information and physiological data of a user. For example, the correlator 1713 may determine a location of a user for at a period of time, such as by using GPS sensor data or triangulation sensor data. In this example, the correlator 1713 may receive physiological measurement data (such as heart rate measurement data, optical spectroscopy data, hydration level measurement data, blood pressure measurement data, and so forth). The correlator 1713 may correlate the location of the user with the physiological measurement data to increase an accuracy of data analysis, a diagnosis, or result data and/or provide additional details regarding a cause of a change in a hydration condition.

In one example, the correlator 1713 may determine that a user is at work in an office location. When the correlator 1713 detects an increase in a heart rate or a blood pressure of a user, the correlator 1713 may correlate heart rate or blood pressure data and the location information to determine a cause of the cognitive ability reduction event. For example, when a heart rate or blood pressure of an individual increases while at a work in an office, the correlator 1713 may determine that the heart rate or blood pressure increase may be due to psychological causes (such as stress) rather than physiological causes (such as exercising or working out) because the user is at a location where an individual is not likely to physically exert himself or herself.

In another example, the correlator 1713 may determine an occupation of the user, such as by using the profile data 1730. In one embodiment, the correlator 1713 can determinate that the occupation of the user is a higher risk occupation (e.g., a statistically more dangerous occupation). For example, the correlator 1713 can access a database or list (stored at the memory device 1708 or externally) that includes information associated with an occupation, such as environmental exposure. When the correlator 1713 detects that the occupation of the user is a higher risk occupation (e.g., an occupation with a risk level that exceeds a threshold value), the correlator 1713 may correlate heart rate data, blood pressure data, hydration level data, with the occupational information to determine a cause of a hydration condition change. For example, when a heart rate and blood pressure of an individual increases and a hydration level of the individual decreases while the individual is working at an oil refinery or on a farm, the correlator 1713 may determine that the heart rate or blood pressure increase may be due to physiological influences of the occupation (such as strenuous labor or no breaks) rather than psychological causes (such as stress) because the occupation where the individual is working at is likely to include physical exertion.

In a further example, the correlator 1713 may use a multiple regression algorithm to determine a correlation between multiple data points or data sets and a hydration condition. For example, the correlator 1713 may receive heart rate data, skin temperature, bio-impedance data, skin luminosity and hydration level data of a user. In this example, the correlator 1713 may determine a correlation between these types of physiological data and a dehydration event of the individual. For example, the physiological data could be from optical spectroscopy (skin luminosity) and/or bio-impedance data. The correlator 1713 may then determine that as the bio-impedance of an individual increases and skin luminosity decreases, a probability of a dehydration event occurring increases.

Additionally. or alternatively, the correlator 1713 may filter out a correlation determination (e.g., a determination that data points or data sets and a hydration condition may be correlated) when a correlation level is below a threshold level. For example, when the correlator 1713 determines that there may be a 30 percent correlation between a skin temperature or a bio-impedance level of an individual and a fall event, the correlator 1713 may filter out or disregard the correlation information when determining a cause of the fall event. In another example, the correlator 1713 can use a learning algorithm or machine learning to determine when to filter out a correlation determination. For example, at a first instance of a fall, there may be a 30 percent correlation between a skin temperature or a bio-impedance level of an individual and a fall event The correlator 1713 can monitor multiple fall events and use machine learning to determine that the initial 30 percent correlation is actually a 60 percent correlation and adjust the filter to not filter out the correlation between the skin temperature or the bio-impedance level of an individual and a fall event or assign the correlation of the skin temperature or the bio-impedance level of an individual and a fall event a different weight.

Additionally, or alternatively, the correlator 1713 may filter out the correlation determination based on a schedule of an individual. For example, when the correlator 1713 determines that an individual is taking a lunch break, off of work, or sleeping, the correlator 1713 may filter out environmental conditions that are associated with the occupation of the user, e.g., the correlator 1713 can filter out false positives.

Additionally, or alternatively, the correlator 1713 may discount or weight a correlation determination based on the correlation level of the correlation determination. For example, when the correlator 1713 determines that there may only be a 30 percent correlation between an occupation of an individual and a hydration level of an individual, the correlator 1713 may discount or assign a lower weight to the correlation determination (relative to a higher correlation percentage such as 90 percent) when determining a change in hydration condition.

Additionally, or alternatively, the correlator 1713 may assign weights to different factors, such as: physiological data 1724 (e.g., different types or qualities of physiological parameters), environmental data 1726 (e.g., different types or quality of environmental parameters), Newtonian data 1728 (e.g., different types or quality of Newtonian parameters), profile data 1730, location data 1732 (e.g., different types or quality of location parameters), a time of day, and so forth. In one example, the correlator 1713 may assign a first weight to hydration level data of an individual and a second weight to profile data of an individual when determining a probability of a change in hydration condition for an individual. In this example, when determining the probability of a change in a hydration condition, the correlator 1713 may assign a higher weight to the hydration level data relative to the profile data, for example.

The correlator 1713 may additionally, or alternatively, use predetermined weights for the physiological data 1724, environmental data 1726, Newtonian data 1728, profile data 1730, and location data 1732. In another example, the correlator 1713 may receive user defined or predefined weights from an input device indicating the weights for the different physiological and/or environmental data. In another example, the correlator 1713 may determine the weights to assign to the physiological data 1724, environmental data 1726, Newtonian data 1728, profile data 1730, and location data 1732 based on correlation levels of the physiological data 1024, environmental data 1726, Newtonian data 1728, profile data 1730, and location data 1732. For example, when a correlation level between a hydration condition and a heart rate of an individual may be relatively low over a threshold period of time and/or under a threshold number of different conditions, the correlator 1713 may assign a low weight to heart rate data when determining a cause of a change in hydration condition.

In one example, the correlator 1713 may assign different weights to one or more of the physiological data 1724, environmental data 1726, Newtonian data 1728, profile data 1730, and location data 1732 based on other physiological data 1724, environmental data 1726, Newtonian data 1728, profile data 1730, and location data 1732. For example, based on a location of an individual, the correlator 1713 may assign a first weight to environmental data 1726 and a second weight to profile data 1730. In another example, the correlator 1713 may assign weights to different hydration conditions.

Additionally, or alternatively, the correlator 1713 may use environmental data 1726 or location data 1732 to determine a cause of a change in hydration condition. For example, when a user is located at a fitness facility working out, the correlator 1713 may increase a weight for a physical exertion related a change in a hydration condition occurring because of in physical exertion of a user (such as an increase in a heart rate or decrease in a hydration level of a user). In another example, when a user is located at home in bed resting or sleeping, the correlator 1713 may correlate a location of the user with the hydration condition of the user. In this example, the correlator 1713 may determine that a decrease in probability of a change in a hydration condition occurring due to an individual being is located in their bedroom for a threshold period of time (e.g., a safer environment).

In one embodiment, the correlator 1713 can determine a weighting of measurement information or physiological information using medical evaluation information. In one example, the medical evaluation information includes medical evaluation information of the user, such as a medical physical. The medical evaluation information can include: medical history and health history information, such as whether the user is a smoker or a non-smoker; a user's blood pressure information; hereditary diseases information; a user's sexual health information; a user's dietary information, a user's exercise routine information, such as how often the user exercises; a user's heart or lung examine information; and so forth. In one example, the correlator 1713 can use the medical evaluation information to set initial weight for different data types. The correlator can update or adjust the weights for the different data types using machine learning. For example, the physiological data 1724, environmental data 1726, and Newtonian data 1728 is assigned a first set of weights based on the medical evaluation information. As the electronic device 1700 uses the sensors to collect the physiological data 1724, environmental data 1726, and the Newtonian data 1728, the correlator 1713 can use the physiological data 1724, the environmental data 1726, and the Newtonian data 1728 to customize the weighting of the measurement information or physiological information to the individual. For example, the correlator 1713 can receive medical evaluation information for the user input device of the electronic device 1700 using an input device of the electronic device 1700.

The correlator 1713 may track, sort and/or filter input data. The input data may include: user schedule information, such as a daily schedule of the user; survey information, such as information received from surveys of individuals; research information, such as clinical research information or academic research information associated with one or more hydration conditions of the electronic device; and so forth.

The correlator 1713 may use location-based tracking and/or scheduling information of the user in determining an expected or probable change in a hydration condition. For example, when a user is a member of a sports team, the user's schedule may include practice schedule information and/or game schedule information. In this example, the correlator 1713 may use the schedule information to anticipate that the user may be participating in physical activity and increase a probability that a change in hydration condition may occur.

The correlator 1713 may use timer information determining an expected or probable occurrence of a change in a hydration condition. For example, the correlator can monitor how long it may have been since a user took a break or consumed water. In this example, as the length of time increase between a break or water consumption, the probability that a change in hydration condition may occur increases. In another example, the correlator can use the timer information to periodically request a response from the user. For example, when a change in hydration condition has not occur within a threshold amount of time that would trigger a user response, the electronic device can request a user response from the user when the threshold amount of time has been exceeded.

In another example, the correlator 1713 can have a work mode (the user is at work) and a home mode (the user is at home), where a type of environmental condition that the electronic device monitors for and/or a probability of a change in a hydration condition occurring can increase or decrease when switching between the work mode and the home mode. For example, when the user has a high risk occupation, the correlator 1713 can monitor for change in hydration condition related to the high risk occupation when the correlator is in a work mode and switch to monitoring for changes in a hydration condition related to low risk activities when the correlator is in a home mode.

In another example, the correlator 1713 may use the scheduling information in correlation with a location of the user to determine an expected or probable change in a hydration condition. For example, the scheduling information may indicate that the user may be scheduled to attend a lecture at a physical fitness facility and the correlator 1713 may adjust the types or probabilities of a change in a hydration condition occurring in view of the scheduling information. In this example, while the correlator 1713 may typically increasing a probability of a change in hydration condition occurring for the user in anticipation of physical activity based on the location information (e.g., the physical fitness facility), the correlator 1713 may adjust the adjust the types or probabilities of a change in a hydration condition occurring in view of the scheduling information that the user may be attending a lecture rather than working out.

Additionally, or alternatively, the correlator 1713 may track and update activity levels of users and correlate these levels with hydration conditions over time. For example, the GPS sensor of the electronic device 1700 may indicate that the user usually works out at the gym on Monday, Wednesday and Friday at 7 a.m. and goes on a long bike ride on Saturday, usually starting about 8:30 a.m. Although these activities may not be available within the scheduling information or data of the electronic device 1700 (or other tethered device), the correlator 1713 may execute machine learning to add to a user's activity data these events that normally occur.

The electronic device 1700 may store historical or previous hydration condition information of the user. In one example, the correlator 1013 may store the historical information on the memory device 1708 of the electronic device 1700. In another example, the correlator 1713 may use the communication device 170 (illustrated in FIG. 1), the communication unit 1070 (illustrated in FIG. 10), or the communication interface 1790 to store the hydration condition information on a memory device coupled to or in communication with the electronic device, such as a cloud-based storage device or a memory device of another computing device. In another example, the correlator 1713 may be part of a cloud-based system or the other computing device, as will be discussed in more detail with reference to FIGS. 13 and 14.

The correlator 1713 may filter and/or sort hydration condition information. In one example, the correlator 1718 may receive a filter or sort command from the electronic device or an input device to filter and/or sort the hydration information. In another example, the filter or sort command may include filter parameters and/or sort parameters.

In another example, the correlator 1713 may sort and/or filter the input data based on a trending of hydration conditions. For example, the correlator 1713 may sort hydration conditions that may be trending in an increasing direction or a decreasing direction and may sort the hydration conditions based on the trending. In this example, different hydration conditions for a user may be trending in different directions, such as a dehydration events of a user may be increasing in trending and fall events may be stable or stagnant.

In another embodiment, the baseliner 1715 may receive profile information from a new user to include any or a combination of gender, age, weight, health, fitness level, and family health histories. The health and fitness levels of the user may be based at least in part on physiological measurements received from the physiological sensor(s) 1702 and the activity data received from the Newtonian sensors 1704. The baseliner 1715 may then identify, from a plurality of baseline profiles of other users (e.g., a group of users), a baseline profile that is most-similar to the user profile based on a correlation between the user profile information and baseline profile information. The baseline profiles can include baseline information of a probability of a change in hydration conditions occurring for a user. The user profiles can include information of the types of hydration conditions that may be probable to occur for user.

The baseliner 1715 may then be able to set a baseline against which to judge a hydration condition. In an alternate embodiment, the baseline profile that is most-similar to the user profile is identified from an aggregated baseline profile for a plurality of individuals corresponding to the plurality of baseline profiles. Alternatively, or additionally, the most-similar profiles may look at a hydration condition that occurs for the individual as compared to a group. For example, the user may be most similar to another individual because they both react physiologically similarly to hot temperatures outside. In another example, the user may have a similar dehydration profile to the most-similar profile, meaning, when the user works out the user may reach a dehydration level at a certain point in time that substantially matches the timing of the most-similar profile.

The electronic device 1700 may further receive survey information and/or research information from an input device with which to build or add to the user and/or baseline profiles. For example, the electronic device 1700 may receive survey information that includes: gender information, age information, physical weight information, general health information, family information, fitness level information, and so forth. In one example, the correlator 1713 may determine a correlation between the survey information and user input data. For example, the correlator 1713 may correlate the age, weight, fitness level, and general health level of a user with survey information from other individuals to determine a correlation between the survey information for the individual and the other individuals. In this example, the baseliner 1715 may set a baseline for a measurement of the electronic device 1700 for the individual based on baselines for the other individuals with the same or similar survey information.

In another example, the correlator 1713 may correlate the user information with research information (such as research papers, clinical studies, and so forth). For example, the electronic device may retrieve research information related to a physiological parameter, the correlator 1713 may then correlate the research information with hydration conditions for the user to generate a research correlation. The baseliner 1715 may then adjust the baseline set for the user related to the hydration conditions in response to the research correlation.

The correlator 1713 can store hydration condition information in a hydration condition database 1712. In one embodiment, the correlator 1713 can determine parameters associated with hydration conditions. The parameters can include threshold values for measurements or data values, such as physiological sensor measurements, environmental sensor measurements, Newtonian sensor measurements, location sensor measurements, or profile data 1730. The correlator 1713 can store the hydration condition and the associated hydration parameters in the hydration condition database 1712. For example, the correlator 1713 can determine that parameters for a heat stroke event can be a skin temperature above a 100 degree temperature, blood pressure above 150 systolic, and a bio-impedance level above 15000 ohms (e.g., a dehydration level threshold). In this example, the correlator 1713 can determine these parameters and can store the hydration condition with the associated parameters in the hydration condition database 1712. In another example, the store predetermined hydration conditions with the associated parameters. In another example, the hydration condition database 1712 can receive the hydration conditions and the associated parameters from another device or server 1794.

The preceding examples are intended for purposes of illustration and are not intended to be limiting. The correlator 1713 may identify a correlation between various data points, data sets, data types, and/or hydration conditions. After having a correlation that informs, for example, a heat stroke event, the hydration level, and/or oxygenation level of the user, and further in consideration of a present activity level of the user, the alerter 1717 may alert the user at the proper time when to hydrate or how to moderate activity levels to avoid or minimize a dehydrated condition.

Figure 18:
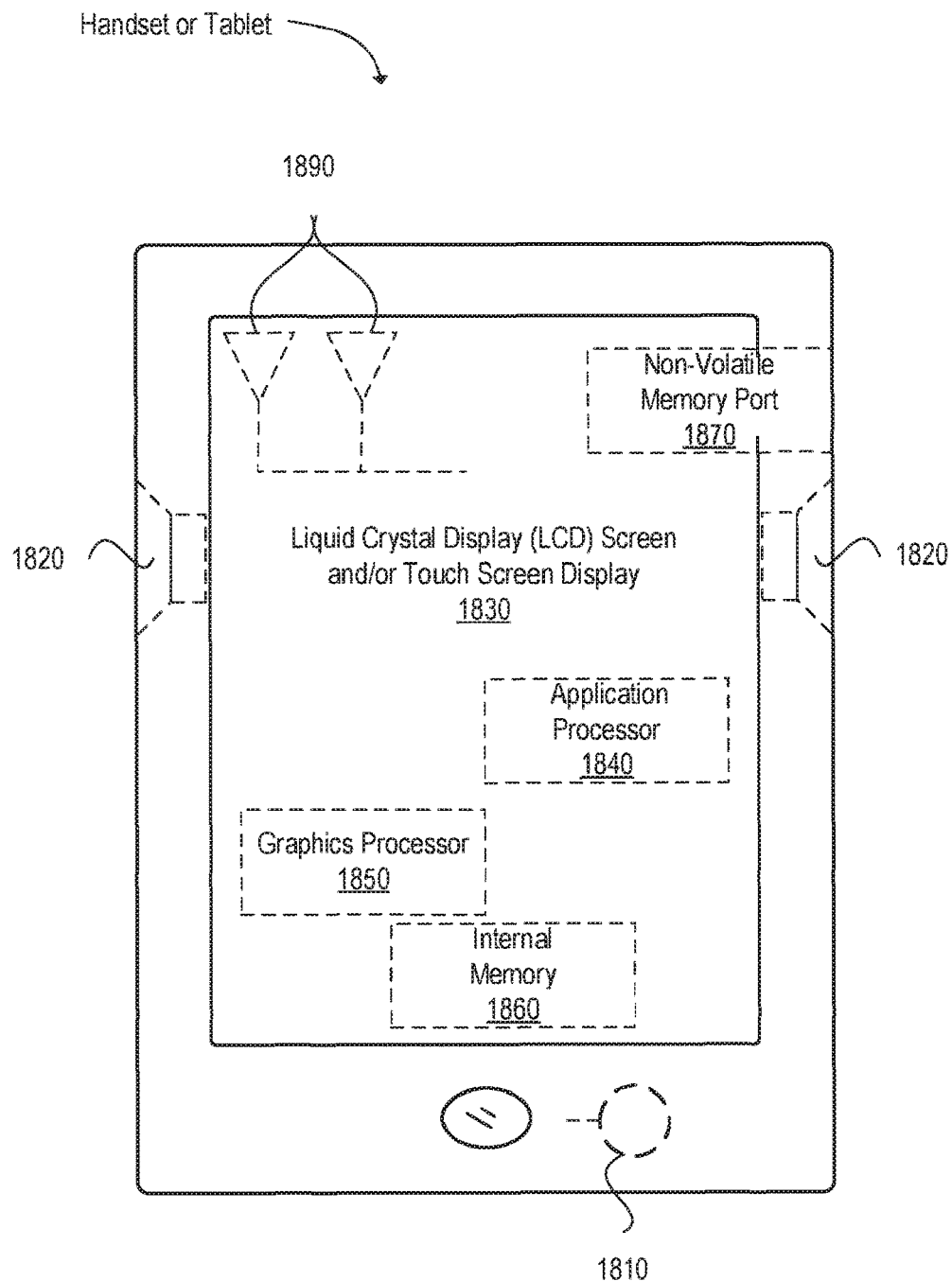
FIG. 18 provides an example illustration of a processing device disclosed herein, such as a user equipment (UE), a base station, an electronic device (UMD), a mobile wireless device, a mobile communication device, a tablet, a handset, or other type of wireless device, according to one embodiment.

FIG. 18 provides an example illustration of a processing device disclosed herein, such as a user equipment (UE), a base station, an electronic device (UMD), a mobile wireless device, a mobile communication device, a tablet, a handset, or other type of wireless device according to one embodiment. The device may include one or more antennas 1890 configured to communicate with a node or transmission station, such as a base station (BS), an evolved Node B (eNode B), a baseband unit (BBU), a remote radio head (RRH), a remote radio equipment (RRE), a relay station (RS), a radio equipment (RE), a remote radio unit (RRU), a central processing module (CPM), or other type of wireless wide area network (WWAN) access point. The device may be configured to communicate using at least one wireless communication standard including 3GPP LTE. WiMAX, High Speed Packet Access (HSPA), Bluetooth, and Wi-Fi. The device may communicate using separate antennas for each wireless communication standard or shared antennas for multiple wireless communication standards. The device may communicate in a wireless local area network (WLAN), a wireless personal area network (WPAN), and/or a WWAN.

FIG. 18 also provides an illustration of a microphone 1810 and one or more speakers 1820 that may be used for audio input and output from the device. The display screen 1830 may be a liquid crystal display (LCD) screen, or other type of display screen such as an organic light emitting diode (OLED) display. The display screen 1830 may be configured as a touch screen. The touch screen may use capacitive, resistive, or another type of touch screen technology. An application processor 1840 and a graphics processor 1850 may be coupled to internal memory 1860 to provide processing and display capabilities. A non-volatile memory port may also be used to provide data input/output options to a user. The non-volatile memory port 1870 may also be used to expand the memory capabilities of the wireless device. A keyboard 1880 may be integrated with the wireless device or wirelessly connected to the wireless device to provide additional user input. A virtual keyboard may also be provided using the touch screen.

Various techniques, or certain aspects or portions thereof, may take the form of program code (i.e., instructions) embodied in tangible media, such as floppy diskettes, CD-ROMs, hard drives, non-transitory computer readable storage medium, or any other machine-readable storage medium where, when the program code is loaded into and executed by a machine, such as a computer, the machine becomes an apparatus for practicing the various techniques. In the case of program code execution on programmable computers, the computing device may include a processor, a storage medium readable by the processor (including volatile and non-volatile memory and/or storage elements), at least one input device, and at least one output device. The volatile and non-volatile memory and/or storage elements may be a RAM, EPROM, flash drive, optical drive, magnetic hard drive, or other medium for storing electronic data. The base station and mobile station may also include a transceiver module, a counter module, a processing module, and/or a clock module or timer module. One or more programs that may implement or utilize the various techniques described herein may use an application programming interface (API), reusable controls, and the like. Such programs may be implemented in a high level procedural or object oriented programming language to communicate with a computer system. However, the program(s) may be implemented in assembly or machine language, if desired. In any case, the language may be a compiled or interpreted language, and combined with hardware implementations.

It should be understood that many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, include one or more physical or logical blocks of computer instructions, which may, for instance, be organized as an object, procedure, or function. Nevertheless, the executables of an identified module need not be physically located together, but may include disparate instructions stored in different locations which, when joined logically together, include the module and achieve the stated purpose for the module.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. The modules may be passive or active, including agents operable to perform desired functions.

Reference throughout this specification to "an example" means that a particular feature, structure, or characteristic described in connection with the example is included in at least one embodiment of the present disclosure. Thus, appearances of the phrases "in an example" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present disclosure may be referred to herein along with alternatives for the various components thereof. It is understood that such embodiments, examples, and alternatives are not to be construed as defacto equivalents of one another, but are to be considered as separate and autonomous representations of the present disclosure.

Furthermore, the described features, structures, or characteristics may be combined in any suitable manner in one or more embodiments. In the foregoing description, numerous specific details are provided, such as examples of layouts, distances, network examples, etc., to provide a thorough understanding of embodiments of the disclosure. One skilled in the relevant art will recognize, however, that the disclosure may be practiced without one or more of the specific details, or with other methods, components, layouts, etc. In other instances, well-known structures, materials, or operations are not shown or described in detail to avoid obscuring aspects of the disclosure.

While the foregoing examples are illustrative of the principles of the present disclosure in one or more particular applications, it will be apparent to those of ordinary skill in the art that numerous modifications in form, usage and details of implementation may be made without the exercise of inventive faculty, and without departing from the principles and concepts of the disclosure. Accordingly, it is not intended that the disclosure be limited, except as by the claims set forth below.

Figure 19:
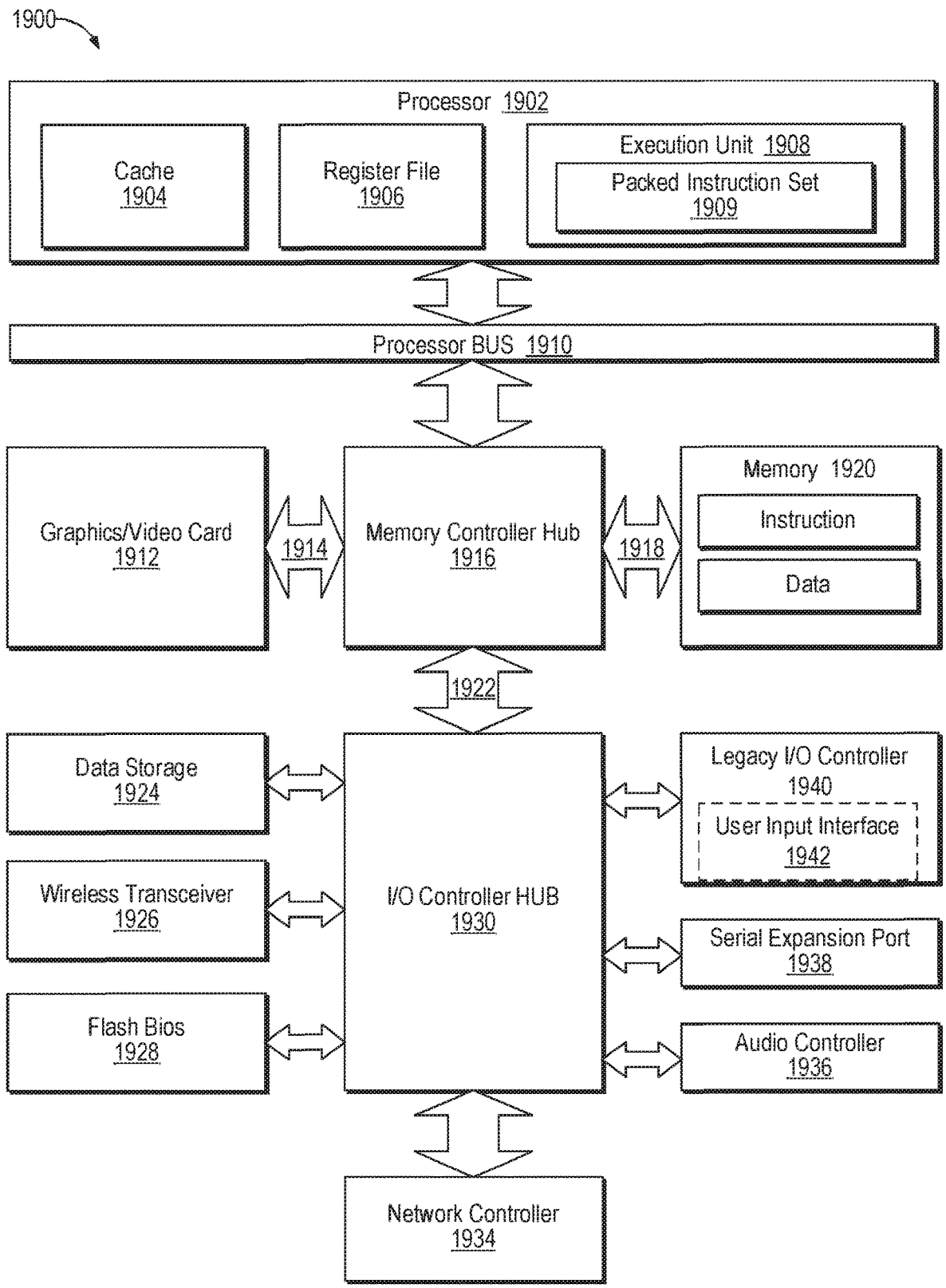
FIG. 19 a block diagram of an exemplary computer system formed with a processor that includes execution units to execute an instruction, where one or more of the interconnects implement one or more features in accordance with one example implementation of the present disclosure is illustrated.

Turning to FIG. 19 a block diagram of an exemplary computer system formed with a processor that includes execution units to execute an instruction, where one or more of the interconnects implement one or more features in accordance with one example implementation of the present disclosure is illustrated. System 1900 includes a component, such as a processor 1902 to employ execution units including logic to perform algorithms for process data, in accordance with the present disclosure, such as in the example implementation described herein. System 1900 is representative of processing systems based on the PENTIUM III™, PENTIUM 4™, XEON™, Itanium, XSCALE™ and/or SRONGARM™ microprocessors available from Intel Corporation of Santa Clara, Calif., although other systems (including PCs having other microprocessors, engineering workstations, set-top boxes and the like) may also be used. In one example implementation, sample system 1900 executes a version of the WINDOWS™ operating system available from Microsoft Corporation of Redmond, Wash., although other operating systems (UNIX and Linux for example), embedded software, and/or graphical user interfaces, may also be used. Thus, example implementations of the present disclosure are not limited to any specific combination of hardware circuitry and software.

Example implementations are not limited to computer systems. Alternative example implementations of the present disclosure can be used in other devices such as handheld devices and embedded applications. Some examples of handheld devices include cellular phones, Internet Protocol devices, digital cameras, personal digital assistants (PDAs), and handheld PCs. Embedded applications can include a micro controller, a digital signal processor (DSP), system on a chip, network computers (NetPC), set-top boxes, network hubs, wide area network (WAN) switches, or any other system that can perform one or more instructions in accordance with at least one example implementation.

Alternative example implementations of the present disclosure can be used in other devices, such as an electronic device. The electronic device may be connected (e.g., networked) to other machines in a LAN, an intranet, an extranet, or the Internet. The electronic device may operate in the capacity of a server or a client device in a client-server network environment, or as a peer device in a peer-to-peer (or distributed) network environment. The electronic device may be a personal computer (PC), a tablet PC, a set-top box (STB), a cellular telephone, a smartphone, a web appliance, a server, a network router, switch or bridge, or any electronic device capable of executing a set of instructions (sequential or otherwise) that specify actions to be taken by that electronic device. Further, while only a single electronic device is illustrated, the term "electronic device" shall also be taken to include any collection of electronic devices that individually or jointly execute a set (or multiple sets) of instructions to perform any one or more of the methodologies discussed herein.

The system 1900 may correspond to the processing device 425 (illustrated in FIG. 4), the controller 1080 (illustrated in FIG. 10), the processing device 804 (illustrated in FIG. 8), or the processor 1703 (illustrated in FIG. 17). The system 1900 may correspond to at least a portion of a cloud-based computer system.

In this illustrated example implementation, processor 1902 includes one or more execution units 1908 to implement an algorithm that is to perform at least one instruction. One example implementation may be described in the context of a single processor desktop or server system, but alternative example implementations may be included in a multiprocessor system. System 1900 is an example of a 'hub' system architecture. The computer system 1900 includes a processor 1902 to process data signals. The processor 1902, as one illustrative example, includes a complex instruction set computer (CISC) microprocessor, a reduced instruction set computing (RISC) microprocessor, a very long instruction word (VLIW) microprocessor, a processor implementing a combination of instruction sets, or any other processor device, such as a digital signal processor, for example. The processor 1902 is coupled to a processor bus 1910 that transmits data signals between the processor 1902 and other components in the system 1900. The elements of system 1900 (e.g. graphics accelerator 1912, memory controller hub 1916, memory 1920, I/O controller hub 1924, wireless transceiver 1926, Flash BIOS 1928, Network controller 1934, Audio controller 1936, Serial expansion port 1938, I/O controller 1940, etc.) perform their conventional functions that are well known to those familiar with the art.

In one example implementation, the processor 1902 includes a Level 1 (L1) internal cache memory 1904. Depending on the architecture, the processor 1902 may have a single internal cache or multiple levels of internal caches. Other example implementations include a combination of both internal and external caches depending on the particular implementation and needs. Register file 1906 is to store different types of data in various registers including integer registers, floating point registers, vector registers, banked registers, shadow registers, checkpoint registers, status registers, and instruction pointer register.

Execution unit 1908, including logic to perform integer and floating point operations, also resides in the processor 1902. The processor 1902, in one example implementation, includes a microcode (ucode) ROM to store microcode, which when executed, is to perform algorithms for certain macroinstructions or handle complex scenarios. Here, microcode is potentially updateable to handle logic bugs/fixes for processor 1902. For one example implementation, execution unit 1908 includes logic to handle a packed instruction set 1909. By including the packed instruction set 1909 in the instruction set of a general-purpose processor 1902, along with associated circuitry to execute the instructions, the operations used by many multimedia applications may be performed using packed data in a general-purpose processor 1902. Thus, many multimedia applications are accelerated and executed more efficiently by using the full width of a processor's data bus for performing operations on packed data. This potentially eliminates the need to transfer smaller units of data across the processor's data bus to perform one or more operations, one data element at a time.

Alternate example implementations of an execution unit 1908 may also be used in micro controllers, embedded processors, graphics devices, DSPs, and other types of logic circuits. System 1900 includes a memory 1920. Memory 1920 includes a dynamic random access memory (DRAM) device, a static random access memory (SRAM) device, flash memory device, or other memory device. Memory 1920 stores instructions and/or data represented by data signals that are to be executed by the processor 1902.

A system logic chip 1916 is coupled to the processor bus 1910 and memory 1920. The system logic chip 1916 in the illustrated example implementation is a memory controller hub (MCH). The processor 1902 can communicate to the MCH 1916 via a processor bus 1910. The MCH 1916 provides a high bandwidth memory path 1918 to memory 1920 for instruction and data storage and for storage of graphics commands, data and textures. The MCH 1916 is to direct data signals between the processor 1902, memory 1920, and other components in the electronic device 1300 and to bridge the data signals between processor bus 1910, memory 1920, and system I/O 1922. In some example implementations, the system logic chip 1916 can provide a graphics port for coupling to a graphics controller 1912. The MCH 1916 is coupled to memory 1920 through a memory interface 1918. The graphics card 1912 is coupled to the MCH 1916 through an Accelerated Graphics Port (AGP) interconnect 1914.

System 1900 uses a proprietary hub interface bus 1922 to couple the MCH 1316 to the I/O controller hub (ICH) 1930. The ICH 1930 provides direct connections to some I/O devices via a local I/O bus. The local I/O bus is a high-speed I/O bus for connecting peripherals to the memory 1920, chipset, and processor 1902. Some examples are the audio controller, firmware hub (flash BIOS) 1928, wireless transceiver 1926, data storage 1924, legacy I/O controller containing user input and keyboard interfaces, a serial expansion port such as Universal Serial Bus (USB), and a network controller 1934. The data storage device 1924 can include a hard disk drive, a floppy disk drive, a CD-ROM device, a flash memory device, or other mass storage device.

For another example implementation of a system, an instruction in accordance with one example implementation can be used with a system on a chip. One example implementation of a system on a chip includes of a processor and a memory. The memory for one such system is a flash memory. The flash memory can be located on the same die as the processor and other system components. Additionally, other logic blocks such as a memory controller or graphics controller can also be located on a system on a chip.

In the following description, numerous specific details are set forth, such as examples of specific types of processors and system configurations, specific hardware structures, specific architectural and micro architectural details, specific register configurations, specific instruction types, specific system components, specific measurements/heights, specific processor pipeline stages and operation etc. in order to provide a thorough understanding of the present disclosure. It will be apparent, however, to one skilled in the art that these specific details need not be employed to practice the present disclosure. In other instances, well known components or methods, such as specific and alternative processor architectures, specific logic circuits/code for described algorithms, specific firmware code, specific interconnect operation, specific logic configurations, specific manufacturing techniques and materials, specific compiler implementations, specific expression of algorithms in code, specific power down and gating techniques/logic and other specific operational details of computer system haven't been described in detail in order to avoid unnecessarily obscuring the present disclosure.

Although the following example implementations may be described with reference to energy conservation and energy efficiency in specific integrated circuits, such as in computing platforms or microprocessors, other example implementations are applicable to other types of integrated circuits and logic devices. Similar techniques and teachings of example implementations described herein may be applied to other types of circuits or semiconductor devices that may also benefit from better energy efficiency and energy conservation. For example, the disclosed example implementations are not limited to desktop computer systems or Ultrabooks™. And may be also used in other devices, such as handheld devices, tablets, other thin notebooks, systems on a chip (SOC) devices, and embedded applications. Some examples of handheld devices include cellular phones, Internet protocol devices, digital cameras, personal digital assistants (PDAs), and handheld PCs. Embedded applications typically include a microcontroller, a digital signal processor (DSP), a system on a chip, network computers (NetPC), set-top boxes, network hubs, wide area network (WAN) switches, or any other system that can perform the functions and operations taught below. Moreover, the apparatus', methods, and systems described herein are not limited to physical computing devices, but may also relate to software optimizations for energy conservation and efficiency. As will become readily apparent in the description below, the example implementations of methods, apparatus', and systems described herein (whether in reference to hardware, firmware, software, or a combination thereof) are vital to a 'green technology' future balanced with performance considerations.

It is described that the system may be any kind of computer or embedded system. The disclosed embodiments may especially be used for electronic device, electronic implants, sensory and control infrastructure devices, controllers, supervisory control and data acquisition (SCADA) systems, or the like. Moreover, the apparatuses, methods, and systems described herein are not limited to physical computing devices, but may also relate to software optimizations for energy conservation and efficiency. As will become readily apparent in the description below, the embodiments of methods, apparatuses, and systems described herein (whether in reference to hardware, firmware, software, or a combination thereof).

Although the following example implementations are described with reference to a processor, other example implementations are applicable to other types of integrated circuits and logic devices. Similar techniques and teachings of example implementations of the present disclosure can be applied to other types of circuits or semiconductor devices that can benefit from higher pipeline throughput and improved performance. The teachings of example implementations of the present disclosure are applicable to any processor or machine that performs data manipulations. However, the present disclosure is not limited to processors or machines that perform 512 bit, 256 bit, 128 bit, 64 bit, 32 bit, or 16 bit data operations and can be applied to any processor and machine in which manipulation or management of data is performed. In addition, the following description provides examples, and the accompanying drawings show various examples for the purposes of illustration. However, these examples should not be construed in a limiting sense as they are merely intended to provide examples of example implementations of the present disclosure rather than to provide an exhaustive list of all possible implementations of example implementations of the present disclosure.

Although the below examples describe instruction handling and distribution in the context of execution units and logic circuits, other example implementations of the present disclosure can be accomplished by way of a data or instructions stored on a machine-readable, tangible medium, which when performed by a machine cause the machine to perform functions consistent with at least one example implementation of the present disclosure. In one example implementation, functions associated with example implementations of the present disclosure are embodied in machine-executable instructions. The instructions can be used to cause a general-purpose or special-purpose processor that is programmed with the instructions to perform the steps of the present disclosure. Example implementations of the present disclosure may be provided as a computer program product or software which may include a machine or computer-readable medium having stored thereon instructions which may be used to program a computer (or other electronic devices) to perform one or more operations according to example implementations of the present disclosure. Alternatively, steps of example implementations of the present disclosure might be performed by specific hardware components that contain fixed-function logic for performing the steps, or by any combination of programmed computer components and fixed-function hardware components.

Instructions used to program logic to perform example implementations of the present disclosure can be stored within a memory in the system, such as DRAM, cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, Compact Disc, Read-Only Memory (CD-ROMs), and magneto-optical disks, Read-Only Memory (ROMs). Random Access Memory (RAM), Erasable Programmable Read-Only Memory (EPROM), Electrically Erasable Programmable Read-Only Memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the computer-readable medium includes any type of tangible machine-readable medium suitable for storing or transmitting electronic instructions or information in a form readable by a machine (e.g., a computer).

The embodiments of methods, hardware, software, firmware or code set forth above may be implemented via instructions or code stored on a machine-accessible, machine readable, computer accessible, or computer readable medium which are executable by a processing element. A non-transitory machine-accessible/readable medium includes any mechanism that provides (i.e., stores and/or transmits) information in a form readable by a machine, such as a computer or electronic system. For example, a non-transitory machine-accessible medium includes random-access memory (RAM), such as static RAM (SRAM) or dynamic RAM (DRAM); ROM; magnetic or optical storage medium; flash memory devices; electrical storage devices; optical storage devices; acoustical storage devices; other form of storage devices for holding information received from transitory (propagated) signals (e.g., carrier waves, infrared signals, digital signals); etc., which are to be distinguished from the non-transitory mediums that may receive information there from.

Instructions used to program logic to perform embodiments of the disclosure may be stored within a memory in the system, such as DRAM, cache, flash memory, or other storage. Furthermore, the instructions may be distributed via a network or by way of other computer readable media. Thus a machine-readable medium may include any mechanism for storing or transmitting information in a form readable by a machine (e.g., a computer), but is not limited to, floppy diskettes, optical disks, Compact Disc, Read-Only Memory (CD-ROMs), and magneto-optical disks, Read-Only Memory (ROMs), Random Access Memory (RAM), Erasable Programmable Read-Only Memory (EPROM), Electrically Erasable Programmable Read-Only Memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the computer-readable medium includes any type of tangible machine-readable medium suitable for storing or transmitting electronic instructions or information in a form readable by a machine (e.g., a computer)

The computer-readable storage medium may also be used to store instructions utilizing logic and/or a software library containing methods that call the above applications. While the computer-readable storage medium can be a single medium, the term "computer-readable storage medium" should be taken to include a single medium or multiple media (e.g., a centralized or distributed database, and/or associated caches and servers) that store the one or more sets of instructions. The term "computer-readable storage medium" shall accordingly be taken to include, but not be limited to, solid-state memories, optical media, and magnetic media.

A design may go through various stages, from creation to simulation to fabrication. Data representing a design may represent the design in a number of manners. First, as is useful in simulations, the hardware may be represented using a hardware description language or another functional description language. Additionally, a circuit level model with logic and/or transistor gates may be produced at some stages of the design process. Furthermore, most designs, at some stage, reach a level of data representing the physical placement of various devices in the hardware model. In the case where conventional semiconductor fabrication techniques are used, the data representing the hardware model may be the data specifying the presence or absence of various features on different mask layers for masks used to produce the integrated circuit. In any representation of the design, the data may be stored in any form of a machine readable medium. A memory or a magnetic or optical storage such as a disc may be the machine readable medium to store information transmitted via optical or electrical wave modulated or otherwise generated to transmit such information. When an electrical carrier wave indicating or carrying the code or design is transmitted, to the extent that copying, buffering, or re-transmission of the electrical signal is performed, a new copy is made. Thus, a communication provider or a network provider may store on a tangible, machine-readable medium, at least temporarily, an article, such as information encoded into a carrier wave, embodying techniques of example implementations of the present disclosure.

In modern processors, a number of different execution units are used to process and execute a variety of code and instructions. Not all instructions are created equal as some are quicker to complete while others can take a number of clock cycles to complete. The faster the throughput of instructions, the better the overall performance of the processor. Thus it would be advantageous to have as many instructions execute as fast as possible. However, there are certain instructions that have greater complexity and require more in terms of execution time and processor resources. For example, there are floating point instructions, load/store operations, data moves, etc.

As more computer systems are used in internet, text, and multimedia applications, additional processor support has been introduced over time. In one example implementation, an instruction set may be associated with one or more computer architectures, including data types, instructions, register architecture, addressing modes, memory architecture, interrupt and exception handling, and external input and output (I/O).

In one example implementation, the instruction set architecture (ISA) may be implemented by one or more micro-architectures, which includes processor logic and circuits used to implement one or more instruction sets. Accordingly, processors with different micro-architectures can share at least a portion of a common instruction set. For example, Intel® Pentium 4 processors. Intel® Core™ processors, and processors from Advanced Micro Devices, Inc. of Sunnyvale Calif. implement nearly identical versions of the x86 instruction set (with some extensions that have been added with newer versions), but have different internal designs. Similarly, processors designed by other processor development companies, such as ARM Holdings, Ltd., MIPS, or their licensees or adopters, may share at least a portion a common instruction set, but may include different processor designs. For example, the same register architecture of the ISA may be implemented in different ways in different micro-architectures using new or well-known techniques, including dedicated physical registers, one or more dynamically allocated physical registers using a register renaming mechanism (e.g., the use of a Register Alias Table (RAT), a Reorder Buffer (ROB) and a retirement register file. In one example implementation, registers may include one or more registers, register architectures, register files, or other register sets that may or may not be addressable by a software programmer.

In one example implementation, an instruction may include one or more instruction formats. In one example implementation, an instruction format may indicate various fields (number of bits, location of bits, etc.) to specify, among other things, the operation to be performed and the operand(s) on which that operation is to be performed. Some instruction formats may be further broken defined by instruction templates (or sub formats). For example, the instruction templates of a given instruction format may be defined to have different subsets of the instruction format's fields and/or defined to have a given field interpreted differently. In one example implementation, an instruction is expressed using an instruction format (and, if defined, in a given one of the instruction templates of that instruction format) and specifies or indicates the operation and the operands upon which the operation will operate.

Scientific, financial, auto-vectorized general purpose, RMS (recognition, mining, and synthesis), and visual and multimedia applications (e.g., 2D/3D graphics, image processing, video compression/decompression, voice recognition algorithms and audio manipulation) may require the same operation to be performed on a large number of data items. In one example implementation, Single Instruction Multiple Data (SIMD) refers to a type of instruction that causes a processor to perform an operation on multiple data elements. SIMD technology may be used in processors that can logically divide the bits in a register into a number of fixed-sized or variable-sized data elements, each of which represents a separate value. For example, in one example implementation, the bits in a 64-bit register may be organized as a source operand containing four separate 16-bit data elements, each of which represents a separate 16-bit value. This type of data may be referred to as 'packed' data type or 'vector' data type, and operands of this data type are referred to as packed data operands or vector operands. In one example implementation, a packed data item or vector may be a sequence of packed data elements stored within a single register, and a packed data operand or a vector operand may a source or destination operand of a SIMD instruction (or 'packed data instruction' or a 'vector instruction'). In one example implementation, a SIMD instruction specifies a single vector operation to be performed on two source vector operands to generate a destination vector operand (also referred to as a result vector operand) of the same or different size, with the same or different number of data elements, and in the same or different data element order.

SIMD technology, such as that employed by the Intel® Core™ processors having an instruction set including x86, MMX™. Streaming SIMD Extensions (SSE), SSE2, SSE3, SSE4.1, and SSE4.2 instructions. ARM processors, such as the ARM Cortex® family of processors having an instruction set including the Vector Floating Point (VFP) and/or NEON instructions, and MIPS processors, such as the Loongson family of processors developed by the Institute of Computing Technology (ICT) of the Chinese Academy of Sciences, has enabled a significant improvement in application performance (Core™ and MMX™ are registered trademarks or trademarks of Intel Corporation of Santa Clara, Calif.).

In one example implementation, destination and source registers/data are generic terms to represent the source and destination of the corresponding data or operation. In some example implementations, they may be implemented by registers, memory, or other storage areas having other names or functions than those depicted. For example, in one example implementation, "DEST1" may be a temporary storage register or other storage area, whereas "SRC1" and "SRC2" may be a first and second source storage register or other storage area, and so forth. In other example implementations, two or more of the SRC and DEST storage areas may correspond to different data storage elements within the same storage area (e.g., a SIMD register). In one example implementation, one of the source registers may also act as a destination register by, for example, writing back the result of an operation performed on the first and second source data to one of the two source registers serving as a destination registers.

A design may go through various stages, from creation to simulation to fabrication. Data representing a design may represent the design in a number of manners. First, as is useful in simulations, the hardware may be represented using a hardware description language or another functional description language. Additionally, a circuit level model with logic and/or transistor gates may be produced at some stages of the design process. Furthermore, most designs, at some stage, reach a level of data representing the physical placement of various devices in the hardware model. In the case where conventional semiconductor fabrication techniques are used, the data representing the hardware model may be the data specifying the presence or absence of various features on different mask layers for masks used to produce the integrated circuit. In any representation of the design, the data may be stored in any form of a machine readable medium. A memory or a magnetic or optical storage such as a disc may be the machine readable medium to store information transmitted via optical or electrical wave modulated or otherwise generated to transmit such information. When an electrical carrier wave indicating or carrying the code or design is transmitted, to the extent that copying, buffering, or re-transmission of the electrical signal is performed, a new copy is made. Thus, a communication provider or a network provider may store on a tangible, machine-readable medium, at least temporarily, an article, such as information encoded into a carrier wave, embodying techniques of embodiments of the present disclosure.

A module as used herein refers to any combination of hardware, software, and/or firmware. As an example, a module includes hardware, such as a micro-controller, associated with a non-transitory medium to store code adapted to be executed by the micro-controller. Therefore, reference to a module, in one embodiment, refers to the hardware, which is specifically configured to recognize and/or execute the code to be held on a non-transitory medium. Furthermore, in another embodiment, use of a module refers to the non-transitory medium including the code, which is specifically adapted to be executed by the microcontroller to perform predetermined operations. And as may be inferred, in yet another embodiment, the term module (in this example) may refer to the combination of the microcontroller and the non-transitory medium. Often module boundaries that are illustrated as separate commonly vary and potentially overlap. For example, a first and a second module may share hardware, software, firmware, or a combination thereof, while potentially retaining some independent hardware, software, or firmware. In one embodiment, use of the term logic includes hardware, such as transistors, registers, or other hardware, such as programmable logic devices.

Use of the phrase 'configured to,' in one embodiment, refers to arranging, putting together, manufacturing, offering to sell, importing and/or designing an apparatus, hardware, logic, or element to perform a designated or determined task. In this example, an apparatus or element thereof that is not operating is still 'configured to' perform a designated task if it is designed, coupled, and/or interconnected to perform said designated task. As a purely illustrative example, a logic gate may provide a 0 or a 1 during operation. But a logic gate 'configured to' provide an enable signal to a clock does not include every potential logic gate that may provide a 1 or 0. Instead, the logic gate is one coupled in some manner that during operation the 1 or 0 output is to enable the clock. Note once again that use of the term 'configured to' does not require operation, but instead focus on the latent state of an apparatus, hardware, and/or element, where in the latent state the apparatus, hardware, and/or element is designed to perform a particular task when the apparatus, hardware, and/or element is operating.

Furthermore, use of the phrases 'to,' 'capable of/to,' and or 'operable to,' in one embodiment, refers to some apparatus, logic, hardware, and/or element designed in such a way to enable use of the apparatus, logic, hardware, and/or element in a specified manner. Note as above that use of to, capable to, or operable to, in one embodiment, refers to the latent state of an apparatus, logic, hardware, and/or element, where the apparatus, logic, hardware, and/or element is not operating but is designed in such a manner to enable use of an apparatus in a specified manner.

A value, as used herein, includes any known representation of a number, a state, a logical state, or a binary logical state. Often, the use of logic levels, logic values, or logical values is also referred to as 1's and 0's, which simply represents binary logic states. For example, a 1 refers to a high logic level and 0 refers to a low logic level. In one embodiment, a storage cell, such as a transistor or flash cell, may be capable of holding a single logical value or multiple logical values. However, other representations of values in computer systems have been used. For example the decimal number ten may also be represented as a binary value of 1010 and a hexadecimal letter A. Therefore, a value includes any representation of information capable of being held in a computer system.

Moreover, states may be represented by values or portions of values. As an example, a first value, such as a logical one, may represent a default or initial state, while a second value, such as a logical zero, may represent a non-default state. In addition, the terms reset and set, in one embodiment, refer to a default and an updated value or state, respectively. For example, a default value potentially includes a high logical value, i.e. reset, while an updated value potentially includes a low logical value, i.e. set. Note that any combination of values may be utilized to represent any number of states.

Reference throughout this specification to "one embodiment" or "an embodiment" means that a particular feature, structure, or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

In the foregoing specification, a detailed description has been given with reference to specific exemplary embodiments. It will, however, be evident that various modifications and changes may be made thereto without departing from the broader spirit and scope of the disclosure as set forth in the appended claims. The specification and drawings are, accordingly, to be regarded in an illustrative sense rather than a restrictive sense. Furthermore, the foregoing use of embodiment and other exemplarily language does not necessarily refer to the same embodiment or the same example, but may refer to different and distinct embodiments, as well as potentially the same embodiment.

Some portions of the detailed description are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared and otherwise manipulated. It has proven convenient at times, principally for reasons of common usage, to refer to these signals as bits, values, elements, symbols, characters, terms, numbers or the like. The blocks described herein may be hardware, software, firmware or a combination thereof.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "defining," "receiving," "determining," "issuing," "linking," "associating," "obtaining," "authenticating," "prohibiting," "executing," "requesting," "communicating," or the like, refer to the actions and processes of a computing system, or similar electronic computing device, that manipulates and transforms data represented as physical (e.g., electronic) quantities within the computing system's registers and memories into other data similarly represented as physical quantities within the computing system memories or registers or other such information storage, transmission or display devices.

The words "example" or "exemplary" are used herein to mean serving as an example, instance or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or." That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Also, the terms "first," "second," "third," "fourth," etc. as used herein are meant as labels to distinguish among different elements and may not necessarily have an ordinal meaning according to their numerical designation.

The invention claimed is:

1. A device comprising:
a housing having an outer surface configured to affix to a body of a user;
a light source embedded within the housing at a first position, wherein the light source is operable to:
emit a first light into the body at a first wavelength of light corresponding to a wavelength absorbed by sodium; and
emit a second light into the body at a second wavelength of light corresponding to a wavelength absorbed by potassium;
an optical sensor embedded within the housing at a second position, wherein the optical sensor is operable to detect a portion of the first light and the second light reflected by interstitial fluid of the body at a depth below an exterior surface of a surface of the body of the user,
a first bio-impedance sensor attached to the housing at a third position such that the first bio-impedance sensor is positioned to transmit an electrical current through the body of the user;
a second bio-impedance sensor attached to the housing at a fourth position such that the second bio-impedance sensor is positioned to receive the electrical current transmitted through the body of the user by the first bio-impedance sensor; and
a processing device configured to:
determine a sodium to potassium ratio of the user based on the reflected A first light and the reflected second light; and
determine a physiological condition of the user based a trend of the sodium to potassium ratio over a period of time and the received electrical current.

2. The device of claim 1, wherein:
the housing comprises a band configured to affix to the body of the user; and the light source and optical sensor are embedded into a bottom portion of the band.

3. The device of claim 1, wherein:
the housing comprises a band configured to affix to a wrist of the user; and
the light source and the optical sensor are embedded into a bottom portion of the band such that the light source and the optical sensor are located adjacent to a bottom surface of the wrist when the device is worn by the user.

4. The device of claim 1, further comprising a sensor interface, coupled to the optical sensor, wherein the sensor interface is to:
take a first measurement of backscatter of the first wavelength of light; and
take a second measurement of backscatter of the second wavelength of light.

5. The device of claim 4, further wherein the processing device is further to:
determine a change in a sodium level of the body when an amount of backscatter of the first wavelength of light changes; and
determine a change in a potassium level of the user when an amount of backscatter of the second wavelength of light changes.

6. The device of claim 5, wherein the physiological condition is a hydration condition.

7. The device of claim 6, wherein the processing device is further operable to:
determine that the hydration condition of the user is in a dehydrated condition when a level of the sodium decreases; or
determine that the hydration condition of the user is in the dehydrated condition when a level of the potassium exceeds the level of the sodium.

8. The device of claim 1, wherein:
the first wavelength of light is between 535 nanometers and 735 nanometers;
or
the second wavelength of light is between 680 nanometers and 880 nanometers.

9. An apparatus comprising:
a housing configured to affix to a wrist of a user, wherein the housing comprises a band to affix the housing to the wrist of the user,
a light source embedded within the housing along an inner surface of the band at a first location at a bottom of the band such that the light source is located adjacent to a bottom surface of the wrist when the apparatus is worn by the user, wherein the light source is operable to emit a light into a body of the user at a wavelength of light corresponding to a wavelength absorbed by blood or sub-epidermis tissue of the user;
an optical sensor embedded within the housing along the inner surface of the band at a second location at the bottom of the band such that the optical sensor is positioned to detect a first portion of the light reflected or backscattered by the blood or the sub-epidermis tissue;
a first bio-impedance sensor embedded within the housing along the inner surface of the band at a third location at the bottom of the band such that the first bio-impedance sensor is positioned to transmit an electrical current through a second portion of the blood or the sub-epidermis tissue of the user;
a second bio-impedance sensor embedded within the housing along the inner surface of the band at a fourth location at the bottom of the band such that the second bio-impedance sensor is positioned to receive the electrical current transmitted through the second portion of the blood or the sub-epidermis tissue of the user by the first bio-impedance sensor; and
a processing device is configured to determine a physiological condition of the user based on the reflected light or the backscatter detected by the optical sensor and the electrical current received by the second bio-impedance sensor.

10. The apparatus of claim 9, wherein the band comprises:
a first cavity disposed along the inner surface of the band, wherein the light source is embedded within the first cavity such that an end of the light source does not extend beyond a plane of the inner surface of the band; and
a second cavity disposed along the inner surface of the band, wherein the optical sensor is embedded within the second cavity such that an end of the optical sensor does not extend beyond the plane of the inner surface of the band.

11. The apparatus of claim 9, wherein the light source or the optical sensor is embedded within the band such that an end of the light source or an end of the optical sensor is flush with the inner surface of the band.

12. The apparatus of claim 9, wherein the band comprises:
a first cavity disposed along the inner surface of the band, wherein the first bio-impedance sensor is embedded within the first cavity such that the first bio-impedance sensor does not extend beyond a plane of the inner surface of the band; and
a second cavity disposed along the inner surface of the band, wherein the second bio-impedance sensor is embedded within the second cavity such that the second bio-impedance sensor does not extend beyond the plane of the inner surface of the band.

13. The apparatus of claim 9, wherein the first bio-impedance sensor or the second bio impedance sensor is embedded within the band such that the first bio-impedance sensor or the second bio-impedance sensor is flush with the inner surface of the band.

14. The apparatus of claim 9, wherein the light source is configured to emit the light at a first wavelength between 535 nanometers and 735 nanometers or a second wavelength between 680 nanometers and 880 nanometers.

15. The apparatus of claim 9, wherein:
the light source is a spectrometer configured to emit light across a defined range of wavelengths of light; and
the optical sensor is configured to detect the reflected or backscattered light within the defined range of wavelengths of light.

16. The apparatus of claim 15, wherein the defined range of wavelengths of light includes a first wavelength corresponding to sodium of the body and a second wavelength corresponding to potassium of the body.

17. The apparatus of claim 9, wherein the processing device is configured to determine a hydration condition of the user based on the reflected light or the back scatter detected by the optical sensor and the electrical current received by the second bio-impedance sensor.

18. A method comprising:
emitting, by a light source affixed to a body at a first position, a first wavelength of light into the body;
receiving, by an optical sensor affixed to the body at a second position, light from a depth below a surface of the body corresponding to blood or sub-epidermis tissue of the body;

receiving, by a bio-impedance sensor affixed to the body at a third position, an electrical current transmitted through the body, wherein:

the first position is at a fixed distance from the second position to detect backscatter from the depth below the surface of the body; and the first position of the light source is at a first side of a muscular walled tube of the body and the second position of the optical sensor is at a second side of the muscular walled tube such that the light source and the optical sensor straddle the muscular walled tube; and determining a physiological condition of the body when a current amount of light reflected or backscattered by blood or the sub-epidermis tissue and received by the optical sensor is different than a previous amount of light reflected or backscattered by the blood or the sub-epidermis tissue and received by the optical sensor and based on the received electrical current.

19. The method of claim 18, wherein:

the light source is embedded within a band affixed to a wrist of the body at a first location at a bottom of the band such that the light source is located adjacent to a bottom surface of the wrist when the band is worn by a user; and the optical sensor is embedded within the band at a second location at the bottom of the band such that the optical sensor is located adjacent to the bottom surface of the wrist when the band is worn by the user.

20. The method of claim 19, further comprising:

transmitting an electrical current through a portion of the blood or the sub-epidermis tissue of the user by a first bio-impedance sensor embedded within the band along the bottom surface of the band at a third location; and receiving the electrical current transmitted through the portion of the blood or the sub-epidermis tissue of the user by a second bio-impedance sensor embedded within the band along the bottom surface of the band at a fourth location.

\* \* \* \* \*